(12) United States Patent
Dashevsky et al.

(10) Patent No.: US 12,343,575 B1
(45) Date of Patent: Jul. 1, 2025

(54) BIOMETRIC AND ENVIRONMENTAL MONITORING AND CONTROL SYSTEM

(71) Applicant: Orbital Research Inc., Cleveland, OH (US)

(72) Inventors: David Dashevsky, Cupertino, CA (US); Matthew Birch, Madison, AL (US); Frederick Lisy, Euclid, OH (US)

(73) Assignee: Orbital Research Inc., Cleveland, OH (US)

( * ) Notice: Subject to any disclaimer, the term of this patent is extended or adjusted under 35 U.S.C. 154(b) by 234 days.

(21) Appl. No.: 17/984,372

(22) Filed: Nov. 10, 2022

Related U.S. Application Data

(63) Continuation of application No. 16/729,550, filed on Dec. 30, 2019, now Pat. No. 11,524,187, which is a
(Continued)

(51) Int. Cl.
*A62B 9/00* (2006.01)
*A61B 5/00* (2006.01)
(Continued)

(52) U.S. Cl.
CPC ............ *A62B 9/006* (2013.01); *A61B 5/0833* (2013.01); *A61B 5/0836* (2013.01); *A61B 5/486* (2013.01);
(Continued)

(58) Field of Classification Search
CPC .............. A61B 5/1455; A61B 5/14551; A61B 5/14552; A61B 5/14553; A61B 5/14555; A61B 5/14556; A61B 5/14557; A61B 5/14558; A61B 5/1459; A61B 5/1464; A61B 5/0826; A61B 5/083; A61B 5/0833;
(Continued)

(56) References Cited

U.S. PATENT DOCUMENTS 3,572,331 A * 3/1971 Kissen .................. B64D 13/04
340/611
5,355,893 A * 10/1994 Mick ...................... A61B 5/087
600/538
(Continued)

*Primary Examiner* — Elliot S Ruddie
(74) *Attorney, Agent, or Firm* — Brian Kolkowsky

(57) ABSTRACT

A wearable device for comprehensive bio-monitoring of physiologic metrics to determine metabolic, pulmonary and cardiac function and oxygen saturation measurements from breathing mask apparatuses. The device non-invasively monitors the physiologic profile of the subject, and is capable of detecting physiologic changes, predicting onset of symptoms, and alerting the wearer or another person or system. In some embodiments, the device comprises both a wearable sensor suite and a portable gas composition and flow analysis system. In preferred embodiments, it comprises a miniaturized non-invasive sensor suite for detecting physiologic changes to detect dangerous breathing or other health conditions. The acquired physiologic profile is used to generate alarms or warnings based on detectable physiological changes, to adjust gas delivery to the subject, alter mission profiles, or to transfer control of the craft or other duties away from a debilitated subject. The device is compact, portable, vehicle independent and non-encumbering to the subject.

20 Claims, 17 Drawing Sheets

Related U.S. Application Data continuation of application No. 14/510,596, filed on Oct. 9, 2014, now Pat. No. 10,561,863, which is a continuation-in-part of application No. 13/441,515, filed on Apr. 6, 2012, now abandoned.

(60) Provisional application No. 61/889,826, filed on Oct. 11, 2013, provisional application No. 62/056,035, filed on Sep. 26, 2014.

(51) Int. Cl.
  *A61B 5/083* (2006.01)
  *A62B 7/14* (2006.01)
  *A62B 18/02* (2006.01)

(52) U.S. Cl.
  CPC .......... *A61B 5/6803* (2013.01); *A61B 5/7225* (2013.01); *A61B 5/7275* (2013.01); *A61B 5/7278* (2013.01); *A62B 7/14* (2013.01); *A62B 18/02* (2013.01)

(58) Field of Classification Search
  CPC ..... A61B 5/0836; A61B 5/087; A61B 5/0873; A61B 5/088; A61B 5/486; A61B 5/0482; A61B 5/6802; A61B 5/6803; A61B 5/6804; A61B 5/6805; A61B 5/7225; A61B 5/7275; A61B 5/7278; A62B 9/006; A62B 7/14; A62B 18/02
  USPC ............ 128/201.27, 204.21, 204.22, 204.23; 600/348, 353
  See application file for complete search history.

(56) References Cited

U.S. PATENT DOCUMENTS

| | | | | |
|---|---|---|---|---|
| 5,503,145 A | * | 4/1996 | Clough | A62B 7/00 128/204.22 |
| 6,186,142 B1 | * | 2/2001 | Schmidt | A61M 16/0051 128/207.18 |
| 9,808,656 B2 | * | 11/2017 | Vinnakota | A62B 9/006 |
| 2001/0029340 A1 | * | 10/2001 | Mault | A61B 5/742 600/531 |

* cited by examiner

CSSAS, Diver Heads Up Display, Underwater Transmitter, and SCUBA Rig monitoring

BIOMETRIC AND ENVIRONMENTAL MONITORING AND CONTROL SYSTEM

CROSS-REFERENCE TO RELATED APPLICATIONS

This application is a continuation of U.S. patent Ser. No. 16/729,550, which was filed on Dec. 30, 2019, and which is a continuation of U.S. patent Ser. No. 14/510,596, which was filed on Oct. 9, 2014, issued as U.S. Pat. No. 10,561,863 on Feb. 18, 2020, and which is each of: 1) a continuation-in-part of U.S. patent application Ser. No. 13/441,515, which was filed on Apr. 6, 2012 and now abandoned, 2) a non-provisional application claiming priority to U.S. Provisional Patent application Ser. No. 61/889,826, which was filed on Oct. 11, 2013, and 2) a non-provisional application claiming priority to U.S. Provisional Patent application Ser. No. 62/056,035, which was filed on Sep. 26, 2014.

STATEMENT REGARDING FEDERALLY-SPONSORED RESEARCH OR DEVELOPMENT

The U.S. Government has a paid-up license in this invention and the right in limited circumstances to require the patent owner to license others on reasonable terms provided for by the terms of the Phase I grant number N68335-09-C0294 awarded by the Department of Defense, and Phase II grant number N68335-10-C0548, also awarded by the Department of Defense.

BACKGROUND OF THE INVENTION

1. Field of the Invention

The present invention relates to monitoring apparatus worn by pilots and other aircrew during flight, divers, first responders, war fighters, climbers, patients and other breathing apparatuses. The present invention further relates to physiologic monitoring systems that monitor and predict changes in physiologic states based on altered respiratory performance and/or gas conditions indicative of dangerous breathing or other health conditions in pilots and aircrew, divers, first responders, and other subjects using breathing apparatuses. The present invention further relates to warning and control transfer systems that can automatically generate alarms or warning signals to the wearer or third parties, monitor and record physiological data of the wearer and transmit such data, and/or transfer duties away from debilitated subjects.

2. Technical Background

Hypoxia, as one example of a physiological condition the present invention may be used to monitor, detect, predict and mitigate, or the deprivation of adequate oxygen supply to the body, and particularly the brain, is a major concern for pilots and aircrew, divers, and other subjects operating in conditions where breathing conditions are impaired by environmental conditions such as altitude, pressure, contamination, or the like. Generalized hypoxia occurs where the person's body, as a whole, is deprived of an adequate oxygen supply, whereas tissue hypoxia is such deprivation to a single organ, tissue, or region of the body. Similarly, other dangerous breathing or other health conditions may occur where the symptoms or outward signs of the dangerous condition appear to be symptomatic of, but not actually be classical hypoxia.

Hypoxia and similar or related dangerous breathing or other health conditions may occur as a result of numerous situations or conditions, or physiologic changes in the subject, but most often occurs at high altitudes, under high gravitational forces (or g-loads) or underwater, or when breathing in a mixture of gases with low oxygen content. More specifically, generalized hypoxia tends to be caused by low partial pressure of oxygen in the person's blood. However, such hypoxia may occur even if the partial pressure of oxygen in the blood is normal. In such cases, the hypoxia may be caused by low partial pressure of atmospheric oxygen (i.e., at high altitude, breathing mixes such as for divers, or when artificial conditions change the atmospheric breathing mix, such as in a fire or in a sewer). Surgical conditions, such as when being taken off inhaled anesthesia and returning to breathing atmospheric air, may cause hypoxia or other health issues in patients. Other medical conditions, such as sleep apnea or hypopnea, chronic obstructive pulmonary disease, or the like, may also cause hypoxia to occur.

Symptoms of hypoxia and similar or related dangerous breathing or other health conditions generally depend on the extent and severity of the deprivation of oxygen to the person's body, or region thereof. Oxygen deficiency in the body will impair the function of the brain and other organs. Loss of physical and mental abilities from hypoxia exposure continues to be a concern at high altitudes or under gravitational forces or g-loads and in recirculated breathing situations. Hypoxia symptoms include headaches, nausea, dizziness, fatigue, shortness of breath, tingling, euphoria, confusion, aggression, visual impairment, and loss of situational awareness. More severe symptoms may also occur, and include loss of consciousness, seizures, priapism, coma, or even death. The skin taking on a blue hue also denotes severe hypoxia.

Clinically, concerns associated with altitude were reported as early as 400 B.C. A cascade of physiologic changes occurs in altitude, none of which are functionally beneficial. For example, pulmonary ventilation increases, causing a hyperventilation state, affecting carbon dioxide clearing which may lead to respiratory alkalosis altering bicarbonate production. Further, ventilation rate and blood pH will increase. Cardiac output (Q) is increased through heart rate compensations. Blood pressure in the pulmonary arteries increases. The oxygen diffusion gradient is reduced by nearly 50% and hemoglobin saturation is reduced by 5-10%. When these physiologic changes are uncontrolled, breathing difficulty, mental confusion, poor judgment, loss of muscle coordination, unconsciousness, lack of useful consciousness, dizziness, light-headedness, fatigue, visual impairment, delayed reaction time, nausea, tingling and numbness, and particularly in vehicular (more particularly aircraft) travel, G-force induced loss-of-consciousness can result. Dangerous breathing or other health conditions can result in loss of situational awareness, may impact mission success, and has led to aircraft mishaps. A complicating factor is that there are wide individual differences in tolerance to acute and chronic exposures to reduced oxygen environments.

Hypoxia and similar or related dangerous breathing or other health conditions including fatigue induced by long missions, high altitudes or g-loads has become an especially critical issue with the growth and development of aircraft and human flight. Hypoxia and fatigue are notoriously important issue for military fighter pilots. The extreme conditions under which these aircraft and pilots operate give rise to a much higher than average onset of hypoxic conditions or fatigue which greatly endanger the pilot's health and safety. The symptoms of hypoxia or fatigue are devastating to such a pilot, operating under such extreme conditions. Hypoxia or fatigue under such flight conditions often goes undetected and unrecognized, and has been determined as a significant factor, or the ultimate cause, of numerous fatal accidents involving military pilots. Additionally, such accidents cost the government millions to billions of dollars in losses when these aircraft are lost. It clearly becomes important to change the current systems and allow for detection and early prediction of hypoxic conditions or fatigue to protect the lives of pilots and aircrew from the highly deadly effects of hypoxia or fatigue under such circumstances. The risk of aircrew members developing dangerous breathing or other health conditions, one example being hypoxia or fatigue, is present with exposure to high altitude flight, acceleration stress, mountain operations (helicopter crew), and the like. Its effects can impair the mission and lead to injury or death of the pilot. While many of the above-mentioned symptoms of hypoxia or fatigue are observable, the exact condition of generalized hypoxia or fatigue has historically been difficult to quantify and there is not a gold standard measure or quantitative metric against which hypoxia can be conclusively verified.

The reduction in barometric pressure that occurs at altitude reduces the partial pressure of oxygen. The lower partial pressure of oxygen limits pulmonary diffusion and oxygen transport to tissue. As result, less oxygen is delivered to tissue and hypoxia (oxygen deficiency) or fatigue sets in. Pilots and other aircrew members utilize an on-board oxygen generation system (OBOGS) to rectify this issue. Alternatively, and particularly with respect to rotorcraft, an OBOGS system referred to as a personal helicopter oxygen delivery system (PHODS) may be employed. However, aviators have been concerned with the potential malfunctions of these systems. Alternatively, and particularly with respect to divers and patients utilize bottled gasses to rectify breathing challenges that would benefit from the proposed system.

For the purposes of combating dangerous breathing or other health conditions, the typical high-performance or high-altitude aircraft is outfitted with one or more on-board oxygen generation system (OBOGS) of the type described, for example, by U.S. Pat. Nos. 4,499,914, 4,651,728, 4,783, 205, 4,858,606, 4,919,124, 4,928,682, 6,923,183, and 6,997, 970, all of which are herein incorporated by reference. A typical OBOGS comprises an apparatus for generating breathable oxygen in elevated concentration and an oronasal mask worn by the aircrew member, the mask adapted to sealably fit on the face surrounding the aircrew member's nose and mouth. Together, the OBOGS and the pressurized cabin function to limit hypoxic conditions. Current protocol for military aircrew/pilots is described as "mask on, always"; however, hypoxia remains the most frequent hazard in aviation medicine. Several factors have been associated with hypoxia, some of which are physiologic, and others being associated with equipment failure. It is important in the context of the present invention to identify and understand many of those geneses. Mechanical causes may include a contaminated OBOGS (smoke/fumes), a leaking or clogged breathing hose, a poor seal around the face of the oronasal mask, OBOGS malfunction (which could be caused by improper maintenance or battle damage), and altered cabin pressure (which again could result from battle damage). Physiological causes may include anemia, medications, blood loss, dehydration, fever, and sleep deprivation. Environment causes may include temperature extremes and anxiety/stress. Other known contributing causes of hypoxia include alcohol use, drug use, and disease.

Cases of dangerous breathing or other health conditions, in pilots are often unreported. Currently, the only warning a pilot typically receives is an OBOGS failure light or their own recognition of the symptoms from training. In both of these cases, the pilot's faculties are on their way to being impaired if they are not already impaired. Due to the insidious nature of hypoxia and other such dangerous breathing or other health conditions, the use of OBOGS instead of gaseous supplies, and the potential for oxygen mask leakage or improper mask use, there is a need for a personal physiologic monitoring system and status monitor that can detect physiologic changes, predict the onset of symptoms, alert the subject, and ideally rectify the problem. It is an object of the present invention to provide these features and advantages. It is thus an object of the present invention to address these issues in pilot and aircrew physiological monitoring and to provide a system capable of detecting or predicting dangerous breathing or other health conditions and in some cases making adjustments to remove the conditions.

Another major area of interest for identifying and predicting dangerous breathing or other health conditions is that of divers, particularly military and combat divers. Such divers generally utilize closed-circulation systems which recirculate breathing gas mixes in order to avoid expiration of gases into the water, which would cause bubbles and thus might give away a diver's location. In many circumstances, a group of divers are deployed in various locations, being deposited by a diver delivery vehicle, and using such a recirculated breathing system to sustain their breathing. However, the symptoms of various dangerous breathing or other health conditions may prevent a diver from being able to perform or respond to conditions, to communicate with other divers or the dive master, or to be found by the delivery vehicle when the mission is over. Dangerous breathing or other health conditions may so disorient a diver that he or she is unable to ascertain the circumstances or to swim, thus leading to greatly increased risks of injury, being lost, or death. Much like pilots above, changing the current diver monitoring systems will help save the lives of numerous divers from the deadly effects of many dangerous breathing or other health conditions. It is thus an object of the present invention to address these issues in physiological monitoring of divers, and to provide a system capable of detecting or predicting dangerous breathing or other health conditions for use with many types of underwater breathing apparatuses including, but not limited to military and combat diver breathing systems, commercial diver breathing systems, recreational and personal diver breathing systems, and the like.

These same concerns arise for other critical response personnel, for example, firefighters and emergency first responders. Firefighters in particular are often subjected to harsh conditions where breathing conditions are harsh and hypoxic. Sensor systems for detection and prediction of dangerous breathing or other health conditions will similarly benefit firefighters and other such first responders who are asked to enter such harsh conditions at their own peril and who may be subjected to great danger if dangerous breathing or other health conditions were to set in, rendering the responder unconscious or incapacitated in some way. It is thus an object of the present invention to address these issues in physiological monitoring of other critical and first response teams, and to provide a system capable of detecting or predicting dangerous breathing or other health conditions.

Additionally, it is envisioned that other breathing mask, and non-breathing mask environments can benefit from a sensor system such as the present invention. Other military and similar scenarios include helicopter pilots, such as those operating in mountain terrain, and soldiers operating at high altitudes. Further, the present invention is envisioned as being usable with systems such as sleep masks, anesthesia delivery systems, oxygen masks and the like. All systems utilizing a breathing mask wherein additional measurements and metrics provided by the present invention can help detect or predict the onset of dangerous health conditions.

In identifying or predicting dangerous breathing or other health conditions, the problem arises in that many dangerous breathing or other health conditions, for example hypoxia, are highly personalized responses to breathing conditions. There are no bright line markers or levels, which indicate at what point a person will become hypoxic. Each person responds differently to breathing conditions, and each person will thus experience various dangerous breathing or other health conditions at a different rate and under different conditions. Traditional methods of monitoring and identifying hypoxia and other conditions have many shortfalls. The most common and generally utilized method of such monitoring is measuring oxygen saturation ($SpO_2$) of the blood by means of a pulse oximeter measurement. Research and trials have shown that oxygen saturation, though useful, is not accurate in identifying individual measures of hypoxia, and is virtually useless in predicting the onset of hypoxia. Because the onset of hypoxia may only be detectable or predictable from a combination of a wide variety of factors, it is important that a physiological monitoring system be capable of detecting and measuring multiple types and varieties of conditions, and combinations thereof, and in using those measurements to determine the individualized response to the given conditions. It is thus an object of the present invention to be able to detect and measure a wide variety of factors, which contribute to hypoxia and other dangerous breathing or other health conditions, and to calculate still others, allowing the system to accurately identify and predict the onset of such conditions.

It is a main object of the present invention to provide a system for use in a variety of applications where OBOGS or PHODS are employed to deliver oxygen or a breathing mix of gases to the subject. It is further, generally an object of the present invention to provide such a system for monitoring the subject's physiological condition and breathing conditions, detecting or predicting dangerous physiological and breathing conditions, for example to detect or predict the onset of hypoxic conditions, to mitigate the onset of such dangerous breathing or other health conditions, and further to provide an alert or warning system to help the subject or a third party take further precautionary or counter measures to prevent, mitigate, or treat such dangerous breathing or other health conditions. Similarly, other dangerous breathing or other health conditions may occur where the symptoms or outward signs of the dangerous condition appear to be symptomatic of classical hypoxia, but may not be. For the purposes of this application, the system is designed to be used for detecting, predicting, mitigating, warning, and/or preventing the onset of dangerous breathing or other health conditions. In other words, most generally, the present invention is intended to provide a system and method for monitoring physiological changes and/or status of the user or subject. More specifically, the system is intended to use the physiologic changes or status changes to detect predict, mitigate, warn and or prevent of the onset of dangerous breathing or other health conditions.

No sensor suite is presently available to detect and preemptively warn the subject of such dangerous breathing or other health conditions. Therefore, it is further an object of the present invention to provide a sensor suite capable of providing an easy-to-interpret warning signal indicating a physiologic change that occurs prior to the potential onset of dangerous breathing or other health conditions, and to non-invasively monitor the physiologic profile of the pilot, diver, or other subject. The physiologic profile will be used to generate alarms or warnings for other members of the team, such as other pilots or divers, a central hub such as a home base, or a dive master, or another remote monitoring station, based on detectable physiological changes.

It is further an object of the present invention to provide a miniaturized non-invasive sensor suite for collecting physiologic measurements to detect hypoxic state. Miniaturization of the sensors is an important feature because it allows for the sensors to be placed in a greater range of devices and places in those devices. Additionally, miniaturization allows for an increased number of sensors to be included in a single system, thus greatly increasing the number of individual and combinations of measurements that can be obtained from the use.

It is further an object of the present invention to provide a compact, portable, vehicle independent system that is non-encumbering to the subject. The system should be able to be retrofitted onto existing breathing mask systems with minimal adaptation or additional equipment. The system should be relatively self-contained, in that the sensors and processor of the system should be located in close proximity to each other, and preferably all contained within the wearable system placed on the subject.

It is further an object of the present invention to provide a physiologic monitoring platform that employs both diagnostic and prognostic capabilities. The system should be able to not only detect or identify when dangerous breathing or other health conditions are presently occurring, but should also be able to substantially predict the onset of such conditions in time to provide an adequate warning to the subject or an exterior monitoring station or team member to try and initialize preventative or corrective procedures.

Potential applications of the present invention include use by Navy, Air Force, and Marine aircrew members, use by Special Forces and other personnel, in mountainous terrain operations, use in performance evaluations and training exercises where the effects of oxygen deprivation are a potential issue, use by military divers, especially those who use rebreather apparatus, potentially exposing them to the dangers of dangerous breathing or other health conditions, mountaineering and high altitude sports, search and rescue personnel and other first responders (especially fire fighters), mining operations, and clinical applications where breathing masks as utilized such as anesthesia, oxygen or sleep masks, and other underwater applications such as underwater construction or farming, recreational or commercial diving, and the like using either rebreathing or non-rebreather systems.

BRIEF SUMMARY OF THE INVENTION

The present invention relates to monitoring apparatus worn by pilots and other aircrew during air flight, underwater divers, first responders such as firemen and rescue personnel, and other breathing mask apparatuses. The system of the present invention is wearable, versatile, small, low-power, minimally invasive, and able to address the monitoring requirements of numerous conditions, scenarios, and settings. The system is capable of conveniently acquiring physiologic metrics and biometric data of a subject that will detect and preferably mitigate the risks and hazards associated with for example high-altitude operations, high g-forces, underwater diving, self-contained breathing apparatuses, high-pressure, low-oxygen, and contaminated air environments among its many applications. The system is capable of acquiring physiological data and/or ambient metrics from subjects that will mitigate the risks and hazards associated with for example hypoxic conditions, hypothermic conditions, hyperventilation, and other conditions that may put the subject physically at risk. The present invention also includes a method of monitoring the physiological condition of aircrew, divers, first responders, patients and others who might benefit from such a monitoring systems ("subjects") as well as a method of adjusting the delivery of gases, medications, chemicals and other physical treatment or stimulation to the subjects. Further, the present invention includes a system for alerting the subject/wearer of the device or a third party of such dangerous breathing or other health conditions, and/or implementing an automated or semi-automated system for closed-loop or semi-closed loop control of the breathing mix of gases.

The systems, devices, and methods of the present invention are designed for use in operations of many varieties. Preferably, the system may be used, or adapted for use, with any vehicle, suit or clothing or wearable apparatus, or other such environments where breathing masks are, or may be used. For example, the system is designed for use in vehicles where the pilot, driver, and/or other crew members or passengers may use breathing masks, such as in fixed wing aircraft, rotorcraft, underwater vehicles, land or ground vehicles, spacecraft, and the like. Further, the system is designed to be used with man-mounted or wearable suits or apparatuses utilizing breathing masks, such as firefighters, combat, recreational, salvage, and all varieties of divers, first responders, and the like. Additionally, the system may be used with non-breathing mask apparatuses such as those breathing systems utilizing nasal cannula or other such breathing gas delivery systems.

The systems, devices, and methods of the present invention are generally designed to be used with systems that utilize on board oxygen generation systems (OBOGS) and personal helicopter oxygen delivery systems (PHODS) or bottled gasses to generate and deliver oxygen and/or a breathing mix of gases to the subject. PHODS are typically man-mounted systems employed specifically in rotorcraft that the helicopter pilot, flight crew, and or passengers wear while the rotorcraft is in flight, but remains with the subject when he or she departs the rotorcraft. Typically, the main difference between OBOGS and PHODS is that OBOGS are generally used with systems that employ breathing mask apparatuses that typically cover and enclose the subject's mouth and nose, whereas PHODS tend to work with systems that employ a partial mask, or no mask, and nasal cannula for delivering oxygen or breathing mix of gases to the subject. Nasal cannula are not exclusive to oxygen or breathing mix delivery systems for rotorcraft, but are also used in various ground applications such as in hospitals, medical transport, and field deployment. For purposes of this application, both OBOGS and PHODS are used interchangeably, and both represent the oxygen delivery system used in conjunction with devices and sensors of the present invention. Thus, the systems, devices, and methods, and particularly the sensors, of the present invention are designed to be either interchangeable between breathing mask and nasal cannula breathing systems, or are adapted to be used with one or the other.

The system collects ambient, environmental, system and physiological data and respiratory gas profiles to track the overall condition of the subject. Ambient, environmental, and system data may include, but is not limited to, pressures, temperatures, g-force, altitude, depth, and the like. Physiological data such as the subject's ventilation, fractional concentration of expired oxygen ($FEO_2$), fractional concentration of expired carbon dioxide ($FECO_2$), breath-by-breath volume (BV), breath frequency (BF), electrocardiogram (ECG), heart rate, axillary skin temperature, galvanic skin response, and blood oxygen saturation ($SpO_2$) are among the many types of data, profiles and metrics that can be acquired alone or in combination by the various embodiments of the present invention. When complete, the data acquired from the system will provide warnings to the subject or others about the onset of hypoxic, hypothermic or other at risk conditions—or can be used in combination with a controller or processor to adjust some condition of the subject including but not limited to the delivery of gases such as oxygen to the subject, or to a separate oxygen or breathing as mix delivery system. Additionally, the data may be used for recording, tracking and identifying events for post hoc review Various embodiments of the system of the present invention use a small or portable sensor unit or units (sometimes referred to as Portable Digital Analysis Unit(s) or PDAUs) capable of providing time based measurements of a subject's ventilation, inhaled breath (e.g., flow, gas concentrations, and the like), oxygen uptake ($O_2$), carbon dioxide ($CO_2$) output, oxygen remaining in expired breath—at rest, during exercise, under various field environments and conditions—particularly extreme environments and conditions. Various embodiments of this system are differentiated from traditional systems such as for example spirometers which are bulky and cumbersome, and which are typically hard-wired to a data acquisition system, and much too finicky and fragile for use outside a controlled laboratory setting. Preferably, the electronic components of the present invention are sufficiently minimized so as to decrease the size and weight of the PDA so that it easier to carry and less cumbersome to the subject or user. Various embodiments further include a breathing mask or system with one or more of the sensors mentioned herein such as gas sensors, organic compound (volatile or non-volatile) sensors, flow sensors, temperature sensors, heat flux sensors, respiration sensors, pressure sensors, physiological electrodes such as ECG, EMG, EOG, and EEG, a pulse oximeter, body conductance sensors, body resistance sensors, accelerometers, gyroscopes, body potential sensors, blood pressure sensors, impedance sensors, microphones, body and blood chemistry sensors, galvanic skin sensor and the like, which can be incorporated for example into or on a mask, a gas intake port or tube, the subject's clothing or equipment, or expired air port or tube as well depending on the function of the sensor and the data needs. The sensors in the mask or system can be tethered wirelessly or by electrical connection. The wireless tethering can be through radio frequency, optical link, acoustics and the like. The sensor signals are transmitted through an appropriate link to an electronic data acquisition or controls box or other subsystem that might in certain embodiments contain either a small on-board processor and/or other electronic components for not only receiving the sensor(s) signal, but also for possibly filtering, digitizing, converting, calculating and the like of the signal and data into information related to the subject's physiological condition and in certain embodiments using that information or data to control the delivery of gases, medication, and/or other physical stimulation to the subject.

The monitoring apparatus is preferably a small, wearable system containing at least one sensor for detecting and measuring particular conditions of the subject's breathing. The sensors are preferably integrated into a breathing mask or nasal cannula breathing system and are therefore external to the subject's body, thus making the present invention a non-invasive, or minimally invasive system. The sensors are preferably miniaturized so as to fit into breathing mask or nasal cannula systems. Also preferably, the system may be designed to be easily retrofitted or attached onto existing breathing mask systems by attachment means such as threads, clamps, snaps, pressfit connectors, lock rings, set screws, and the like, thus minimizing the amount of hardware and equipment actually necessary to implement the present invention, while maximizing the utility of the system across multiple platforms. Alternatively, some embodiments may utilize sensors that are implanted directly into a breathing mask system. For example, a sensor, or sensor wires or contacts, may be inserted directly through the breathing mask system (e.g., by punching a hole through the mask system, then sealing the whole around the sensor, or sensor leads or contacts to maintain an airtight seal). Other embodiments, particularly ground applications such as stationary medical care facilities (e.g., hospitals, forward/field care units, and the like) and medical transport (e.g., ambulance, helicopter), may include sensors that are attached, integrated, or otherwise installed directly into medical hoses and tubing. The majority of embodiments of the present invention are specifically designed to include sensors that are modular in nature and can be easily attached, detached, added, and replaced in the event of failure. The sensors may further be able to be added in series with each other. The present invention is designed to be used or adapted to be used un any of these environments to help monitor, detect, predict, mitigate and or prevent dangerous breathing or other health conditions of any type of user, including both children and adults.

In order to measure the breathing conditions and to identify and predict the onset or presence of various physical conditions of the subject including but not limited to hypoxia, hypothermia, hypo- and hyperventilation, G-LOC, atelectasis, and the like, sensors are required which have the capability to measure and detect numerous conditions surrounding the subject. Such conditions include physiological signals from the person wearing the device, as well as environmental and ambient conditions, and status or conditions of the system, and signals related to those conditions. For example, sensors for detection and measurement of all ambient air gases may be used to determine the conditions of both inhaled and exhaled breaths of the subject. Most importantly, sensors for detection and measurement of oxygen and carbon dioxide are useful for dangerous breathing or other health conditions determination, but sensors for many other gases may be included. Sensors for detection of other surrounding conditions may be included as well, such as for temperature of the inhaled and/or exhaled breaths, ambient temperature, pressure sensors for measuring for ambient (cabin) pressure, ambient pressure (non-enclosed environments such as divers, man-mounted systems, ground applications, and the like), in-mask pressure, vest pressure, and the like, flow sensors for measuring gas flow either pre- or post-inhalation, g-force sensors, or sensors for detection of volatile organic compounds (e.g., jet fuel), hydrocarbons, and other such contaminants which may be present and have an adverse effect on a person's breathing and oxygen levels. Further embodiments include monitoring the gasses and its flow rates, pressures and temperatures being delivered to the subject. This embodiment may include an integrated PDAU to aid in the integration onto various life support platforms.

Various embodiments of the present invention may also include a third party monitoring system of the subject's physiological condition and/or various control and actuations systems including algorithms, which are used to change the subject's environment to improve the subject's physiological condition, to actively warn the subject, to reposition the subject's environment, or to adjust the subject's hardware.

Measurements and signals from the sensors described herein are further used to calculate other environmental and physiological conditions of and surrounding the subject. The sensor measurements and subsequent algorithmic calculations are used to monitor the subject's overall condition, to detect or predict the onset of dangerous breathing or other health conditions, to mitigate the onset or severity of those dangerous breathing or other health conditions and their symptoms, and to activate an alert or warning system which notifies the subject or a third party who may then initiate action to further prevent, mitigate, or treat the dangerous conditions and symptoms.

Various features of the present invention are described within this patent application. It is understood that the present invention can be considered to embody many of these features in various combinations without departing from the spirit of the present invention. A small number of examples of the present invention are described in the following embodiments. One embodiment of the present invention includes a breathing mask sensor system for identifying or predicting dangerous health conditions comprising at least one sensor having a signal related to an in-breath partial pressure of oxygen from exhaled breath of a subject, and a processor for receiving the signal, the processor further comprising an algorithm, wherein the algorithm is for substantially identifying or predicting a mass of oxygen absorbed per breath based at least in part on the signal related to the partial pressure of oxygen from exhaled breath of the subject.

Another embodiment of the present invention includes a breathing mask sensor system for identifying or predicting dangerous health conditions comprising at least one sensor having a signal related to an in-breath partial pressure of carbon dioxide from exhaled breath of a subject, and a processor for receiving the signal, the processor further comprising an algorithm, wherein the algorithm is for substantially identifying or predicting a mass of oxygen absorbed per breath based at least in part on the signal related to the partial pressure of carbon dioxide from exhaled breath of the subject.

Yet another embodiment of the present invention includes a breathing mask sensor system for identifying or predicting dangerous health conditions comprising at least one sensor having a signal related to an in-breath partial pressure of oxygen from inhaled breath of a subject, air flow, and rest rate, at least one sensor having a signal related to an in-breath partial pressure of oxygen from exhaled breath of a subject, and a processor for receiving the signals, the processor further comprising an algorithm, wherein the algorithm is for substantially identifying or predicting a mass of oxygen absorbed per breath based at least in part on the signal related to the partial pressure of oxygen from inhaled and exhaled breath of the subject.

Still another embodiment of the present invention includes a breathing mask sensor system for identifying or predicting dangerous health conditions comprising at least one sensor having a signal related to an in-breath partial pressure of oxygen from inhaled or exhaled breath of a subject, and a processor for receiving the signal, the processor further comprising an algorithm, wherein the algorithm is for substantially identifying or predicting oxygen saturation in blood based at least in part on the signal related to the partial pressure of oxygen from exhaled breath of the subject.

Another embodiment of the present invention includes a breathing mask sensor system for identifying or predicting dangerous health conditions comprising at least one sensor having a signal related to temperature of exhaled breath of a subject, and a processor for receiving the signal, the processor further comprising an algorithm, wherein the algorithm is for substantially identifying or predicting the subject's core body temperature based at least in part on the signal related to temperature of exhaled breath of the subject.

Yet another embodiment of the present invention includes a breathing mask sensor system for identifying or predicting dangerous health conditions comprising at least one sensor having a signal related to an in-breath partial pressure of carbon dioxide from exhaled breath of a subject, and a processor for receiving the signal, the processor further comprising an algorithm, wherein the algorithm is for substantially identifying or predicting oxygen saturation in blood based at least in part on the signal related to the partial pressure of carbon dioxide from exhaled breath of the subject.

Still another embodiment of the present invention includes a breathing mask sensor system for identifying or predicting dangerous health conditions comprising at least one sensor having a signal relating to a measure of volatile organic compounds contained in an air flow, and a processor for receiving the signal, the processor further comprising an algorithm, wherein the algorithm is for substantially identifying or predicting a toxicity or danger level of said volatile organic compounds.

Still yet another embodiment of the present invention includes a breathing mask sensor system for identifying or predicting dangerous health conditions comprising at least one sensor having a signal related to an in-breath partial pressure of oxygen from exhaled breath of a subject, at least one sensor having a signal related to an in-breath partial pressure of carbon dioxide from exhaled breath of a subject, and a processor for receiving the signal, the processor further comprising an algorithm, wherein the algorithm is for substantially identifying predicting oxygen saturation in blood based at least in part on the signals related to the partial pressure of oxygen, and partial pressure of carbon dioxide from exhaled breath of the subject.

Even still another embodiment of the present invention includes a breathing mask sensor system for identifying or predicting dangerous health conditions comprising at least three sensors having signals, and a processor for receiving the signals, the processor further comprising an algorithm, wherein the signal from at least one of the at least three sensors relates to an in-breath partial pressure of oxygen from exhaled breath of a subject, the signal from at least one of the at least three sensors relates to an in-breath partial pressure of carbon dioxide from exhaled breath of a subject, and the signal from at least one of the at least three sensors relates to temperature of exhaled breath of a subject, and wherein the algorithm is for substantially identifying or predicting oxygen saturation in blood based at least in part on the signals related to the partial pressure of oxygen, and partial pressure of carbon dioxide from exhaled breath of the subject, and for substantially identifying or predicting the subject's core body temperature based at least in part on signal related to temperature of exhaled breath of the subject.

Yet another embodiment of the present invention includes a breathing mask sensor system for identifying or predicting dangerous health conditions comprising at least one sensor having a signal related to an in-breath partial pressure of oxygen from inhaled breath of a subject, air flow, and rest rate, at least one sensor having a signal related to an in-breath partial pressure of oxygen from exhaled breath of a subject, and a processor for receiving the signals, the processor further comprising an algorithm, wherein the algorithm is for substantially identifying or predicting oxygen saturation in blood based at least in part on the signal related to the partial pressure of oxygen from exhaled breath of the subject.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description are merely exemplary of the invention, and are intended to provide an overview or framework for understanding the nature and character of the invention as it is claimed. The accompanying drawings are included to provide a further understanding of the invention, and are incorporated in and constitute a part of this specification. The drawings illustrate various embodiments of the invention and together with the description serve to explain the principles and operation of the invention.

BRIEF DESCRIPTION OF THE DRAWINGS

FIG. 9A depicts the change in partial pressure of oxygen and 9B depicts the change in oxygen saturation.

DETAILED DESCRIPTION OF THE INVENTION

Figure 1:
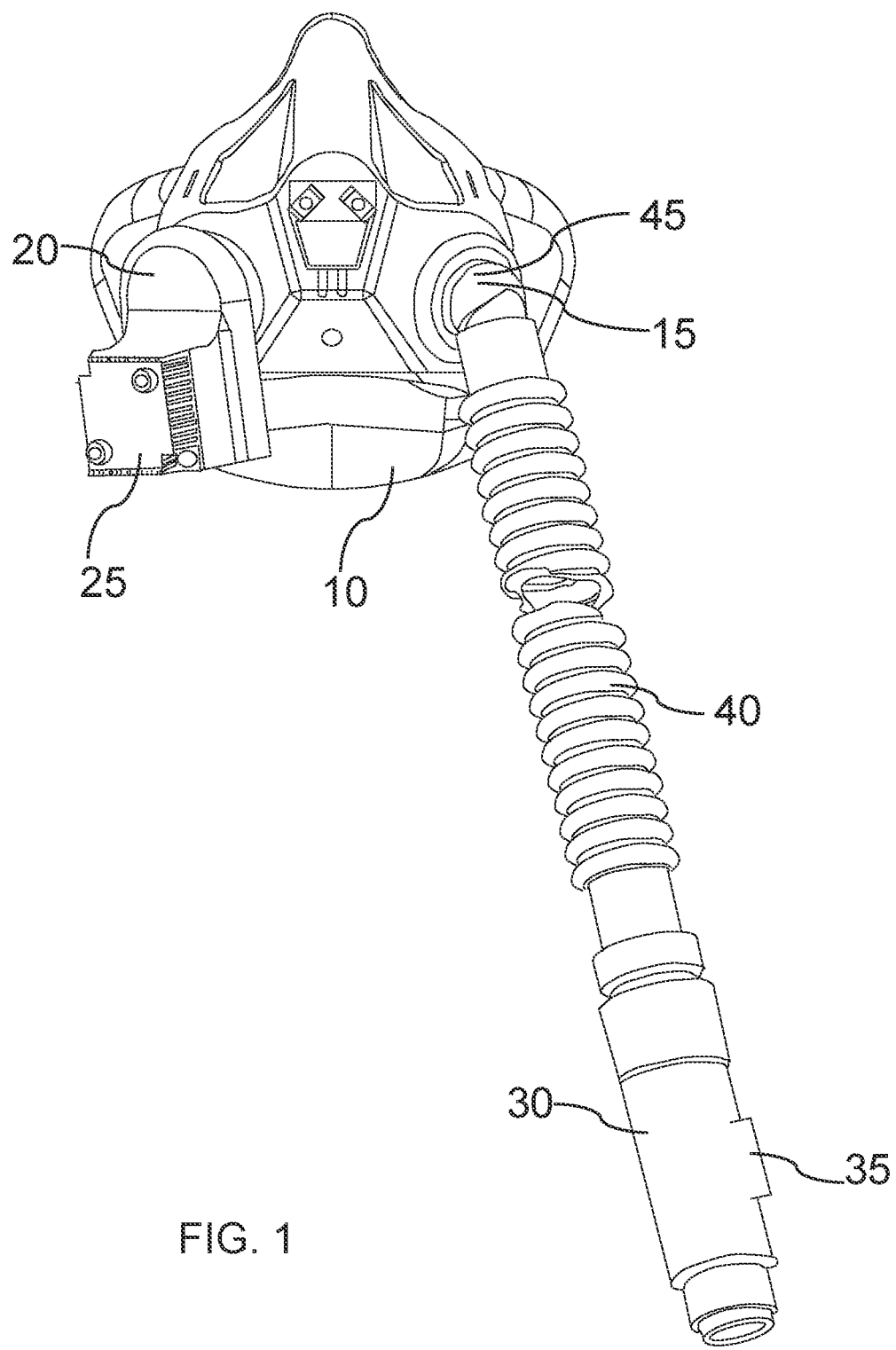
FIG. 1. Perspective view of one embodiment of the present invention of a pilot or aircrew flight mask with multiple sensors used for identification or prediction of dangerous breathing or other health conditions.

The present invention relates to a monitoring apparatus worn by pilots and other aircrew during air flight, divers, first responders such as firemen and rescue personnel, and others who wear breathing mask apparatuses. The system of the present invention is wearable, versatile, small, low-power, minimally invasive, and able to address the monitoring requirements of numerous conditions, scenarios, and settings. As such, this sensor system, which can be incorporated or attached to a breathing mask is capable of conveniently acquiring physiological metrics and biometric data of a subject that will mitigate the risks and hazards associated with for example high-altitude operations, underwater diving, high-pressure, low-oxygen, and contaminated air environments among its many applications. The sensor system is preferably a small, wearable system containing at least one sensor for detecting and measuring particular conditions of the subject's breathing. The system can, however, incorporate other sensors or can be based on sensors other than those for directly detecting and measuring particular conditions of the subject's breath. Further, the sensor system preferably contains at least one processor comprising algorithms, for identifying or predicting dangerous breathing or other health conditions, that compute breathing metrics based at least in part on the signals received from the sensors of the sensor system. In addition, preferably the sensor system may be designed to be retrofitted onto existing breathing mask systems, thus minimizing the amount of hardware and equipment actually necessary to implement the present invention, while maximizing the utility of the system across multiple platforms.

The sensors of the breathing mask sensor system are preferably integrated into a breathing mask system and are therefore external to the subject's body, thus making the present invention a non-invasive, or minimally invasive one. The sensors are preferably miniaturized so as to fit into breathing mask systems. In order to measure the breathing conditions and to identify and predict the onset or presence of dangerous breathing or other health conditions, sensors are required which have the capability to measure and detect numerous conditions surrounding the subject. Sensors for detection and measurement of all ambient air gases may be used to determine the conditions of both inhaled and exhaled breaths of the subject. Most importantly, sensors for detection and measurement of oxygen and carbon dioxide are useful for dangerous breathing condition determinations, but sensors for measuring many other physiological changes in the subject or for measuring changes in the subject's environment may be included. These sensors include but are not limited to temperature sensors, pulse oximeters, physiological electrodes such as ECG, EOG, EEG, EMG and the like, accelerometers, gyroscopes, microphones, flow meters, pressure sensors, galvanic skin sensors, respiratory effort belts, oxygen sensors, carbon dioxide sensors, organic compound (volatile) sensors and the like. Such sensors may be optic, pressure transducers, strain gauges, dry electrodes, chemical transducers, or of other forms of sensors known to those skilled in the art.

The subject's respirations can be measured by measurement of airflow, respiratory effort, oxygenation and ventilation, and the like. Measurement of airflow is preferably measured using sensors or devices such as a pneumotachometer, strain gauges, thermal sensors, transducers, piezo sensors, magnetometers, pressure sensors, static charge-sensitive beds, and the like. These sensors or devices, also preferably measure nasal pressure, respiratory inductance plethysmography, thoracic impedance, expired carbon dioxide, tracheal sound, snore sound, blood pressure and the like. Measurement of respiratory effort is preferably measured by esophageal pressure, surface diaphragmatic EMG, and the like. Measurement of oxygenation and ventilation is preferably measured by pulse oximetry, transcutaneous oxygen and expired oxygen partial pressure monitoring, transcutaneous carbon dioxide monitoring, expired carbon dioxide monitoring, and the like. The sensors are preferably applied to the subject, his or her equipment or clothing, of the system in a manner known to those skilled in the art. Preferably, the sensors are attached or affixed in a non-invasive manner, and preferably to an external housing, wearable, or some other deployment method or device.

One example of such a sensor housing, wearable or deployment method or device for measuring respirations either directly or indirectly is a respiration belt. Respiration belts can be used to measure a subject's abdominal and/or thoracic expansion over a measurement time period. The respiration belts may contain a strain gauge, a pressure transducer or other sensors, which can indirectly measure a subject's respirations and the variability of respirations by providing a signal, which correlates to the thoracic/abdominal expansion/contractions of the subject's abdominal cavity. Respiration belts may be placed at one or several locations on the subject's torso or in any other manner known to those skilled in the art. Preferably, the respiration belts are positioned below the axilla and/or at the level of the umbilicus in order to measure rib cage and abdominal excursions. More preferably, if respiration belts are used then at least two belts are used one being positioned at the axilla and the other at the umbilicus.

Another example of such a sensor housing, wearable or deployment method or device for measuring respirations either directly or indirectly is a nasal cannula or a facemask. The sensors integrated with, attached to, or otherwise used in conjunction with a nasal cannula or facemask can be used to measure the subject's respiratory airflow. Nasal or oral airflow can be measured quantitatively and directly with a pneumotachograph consisting of a standard oxygen nasal cannula or facemask respectively connected to a pressure transducer and placed in the nose or over the subject's mouth and below the nose respectively. Airflow can be estimated by measuring nasal or oral airway pressure that decreases during inspiration and increases during expiration. Inspiration and expiration produce fluctuations on the pressure transducer's signal that is proportional to airflow. The oral and nasal components of these measurements can be acquired through the use of at least two pressure transducers, one transducer for each component. Preferably the two pressure transducers are internal to the interface box and have separate air ports for nasal and oral measurements. Through the use of software filtering, "snore signals" can also be obtained from a sole pressure transducer signal. The software filtering extracts the high frequency portion of the transducer signal to obtain the "snore signal." Thereby eliminating the need for a separate sensor, such as a microphone or another transducer, and also lessening the system resources needed to detect both snore and airflow. A modified nasal cannula or facemask may also be used which is connected to a carbon dioxide or oxygen sensor to measure respective concentrations of these gases. In addition, a variety of other sensors can be connected with either a nasal cannula or facemask to either directly or indirectly measure a subject's respirations.

Still another example of such a sensor or method of either directly or indirectly measuring respirations of the subject is the use of a pulse oximeter. Pulse oximeters of any type known to those skilled in the art may be used. Generally, depending on the location of attachment to the subject's body, pulse oximeters tend to be either transmission or back scatter (a.k.a., reflection) sensors. Transmission sensors operate by generating a source of light at a known frequency and wavelength, passing said light through the subject's body, and measuring the amount of light that exits the subject's body on the other side. Transmission sensors, and particularly pulse oximeters, are typically applied to finger tips or the nose, generally due to the thin nature of those parts of the body as well as the ease in applying a sensor to both sides thus enabling the transmission measurement. Other areas of the body do not lend themselves as well to applying such sensors, and thus back scatter or reflection sensors may be used. Back scatter sensors operate by generating a source of light at a known frequency and wavelength, and then measuring the amount of light that bounces or reflects back to the measurement sensor which is on the same side as the light generator. These sensors are less accurate than transmission sensors due to the loss of light as it scatters once it enters the subject's body—100% reflection is generally unachievable. In spite of the decreased accuracy, these sensors, particularly in pulse oximeters, are useful for application to the subject's ear to which would be uncomfortable and difficult to apply a transmission sensor. More specifically, with regard to the preferred sensor, the pulse oximeter can measure the oxygenation of the subject's blood by producing a source of light originating from the oximeter at two wavelengths (650 nm and 805 nm). The light is partly absorbed by hemoglobin, by amounts which differ depending on whether it is saturated or desaturated with oxygen. By calculating the absorption at the two wavelengths the proportion of hemoglobin which is oxygenated can be estimated. Some embodiments, where the optional pulse oximeter is attached to or incorporated into a helmet, may be referred to as helmet-mounted pulse oximeter (HMPO_) embodiments. In some embodiments, a pulse oximeter may be placed on a subject's fingertip. In other embodiments, a pulse oximeter may be placed directly on a subject's earlobe or forehead. In yet other embodiments, a pulse oximeter may be incorporated into a mask, helmet, or some other wearable, and then placed on the subject's forehead or earlobe when the mask, helmet or wearable is donned. In still yet other embodiments, a pulse oximeter may be attached in the subject's ear cup. In yet other embodiments, a pulse oximeter may be incorporated into a mask, helmet, or some other wearable, and is then placed in the subject's ear cup. In even other embodiments, a pulse oximeter may be applied to the bridge of the subject's nose, and is preferably incorporated into a mask, helmet, or other wearable.

Sensor components are preferably miniaturized to accommodate the various mask types and other systems with which the present invention may be utilized. Sensors of many types and variety may be utilized, but preferably optical sensors are used—for measuring oxygen and carbon dioxide. Optical sensors are those known in the art, which preferably utilize an emitter, preferably light-emitting diodes (LEDs) which is a semi-conductor light source, and a detector to receive the light from the emitter. The detector measures the incoming light and uses that measure to provide a signal which is used to calculate a plethora of metrics based on the change in the light as it passes through the gas (in the present invention either the breathing mix, the inhaled breath, or the exhaled breath).

Preferably, the optical sensors used in the present invention utilize direct coupling between the various components of the sensors, particularly the light source and sensing components. Direct coupling allows the present invention to avoid other forms of coupling presently known in the art which require somewhat remote or relatively distant placement of light source, sensing and measurement components, such as through fiber-optic cable coupling.

This remote placement and distance-coupling can have a negative effect on sensor measurements, particularly requiring extensive and repeated calibration, as well as increased difficulty and time required for maintenance. The separation between the sensor components for such systems greatly increases the number and complexity of steps required for such maintenance, and the decoupling of the components can lead to errors in the calibration that require recalibration to ensure accurate sensor operation. To counteract these issues, the present invention uses direct coupling whereby all sensor components are located together and directly coupled to each other creating a single, localized unit. More specifically, the present invention maintains all sensor components localized to the sensor unit that is part of or attached to the mask, in most embodiments. This localized system ensures that the sensor remains calibrated more accurately and with less chance of decalibration, increases the efficiency of the sensor by minimizing the loss of light in the transmission thereof for sensor operation, and minimizes the steps and difficulty of cleaning and maintaining the sensor while thereby further minimizing the risk of calibration errors.

With further respect to calibration of not only the oxygen sensor, but of the sensor suite as a whole, the sensor suite of the present invention preferably is capable of performing a self-calibration step with respect to ambient or room air. This calibration step is important to ensure accurate and consistent measurement of each of the individual sensors in the sensor suite. Typical systems known in the art require the subject and vehicle to be grounded and stationary so that the sensor(s) may be removed and this room-air-calibration step be performed outside of the subject-mounted and/or vehicle/mounted breathing system. This process is time intensive and sensitive, and leaves the sensors vulnerable to potential damage while exposed, and further limits the amount of useful time of the vehicle and subject-mounted systems. The present invention, however, is able to perform a self-calibration, while remaining mounted into the vehicle- and/or subject-mounted systems. Preferably, the system automatically performs this calibration step upon startup, and thus calibrates the sensor(s) to the ambient air each time the vehicle and breathing system or prepared for use by the subject. This eliminates the need to keep the vehicle grounded and stationary, and efficiently allows the system to take accurate, calibrated measurements each time the system is in use. For example, in one embodiment, on startup, the $O_2$ calibration is adjusted by measuring the ambient pressure and assuming that the ambient air is composed of 20.9% oxygen expressed as a mole fraction. This partial pressure is used in the calibration curve, computed in reverse, to calculate the expected raw sensor value at that oxygen level. If the calibration has drifted due to mechanical shifts, slight thermal shifts, or slight wear or the dye, the calibration curve has been experimentally understood to preserve its shape but otherwise translate linearly. The fresh-air calibration snaps the calibration curve to the known point.

The preferred $CO_2$ sensor consists of an array of infrared (IR) light emitting diodes (LEDs) mounted on one side of the sensor, whether that sensor is designed for measuring the partial pressure of $CO_2$ in an inhaled or exhaled breath. The carbon dioxide ($CO_2$) sensor preferably utilizes an infrared absorption technique that uses several infrared (IR) Light Emitting Diodes (LED) focused on a detector. Preferably, the detector is a thermo-electrically cooled detector approximately 1 cm away. The LEDs emit light, preferably at a known input pulse in the range of 4.3 μm, exactly the wavelength where carbon dioxide has an extremely strong and unique absorption cross-section. The light passes through the breath or air in the sensor, and strikes a sensor which records and measures the output form of the light. Where the input was preferably a square waveform impulse, the output will be a sinusoidal shaped curve as a result of the loss of light attributable to the light absorbed by the carbon dioxide in the air or breath in the sensor. The amplitude of the output waveform corresponds to the percentage of carbon dioxide contained in the air or breath. Preferably, a thermo-electric cooler sits behind the IR detector and maintains a constant temperature at the detector.

Further preferably, the present invention is capable of preventing pressure drift in the carbon dioxide sensor measurements which can lead to inaccurate gas concentration measurements. The present invention preferably utilizes a bivariate calibration technique that takes into account the barometric pressure at the time of each measurement. This calibration technique thus allows the system to account for changes in pressure based on the use and operation of the system and rapid changes in pressure, for example during intense flight of a military aircraft. This system provides a drastic improvement over typical capnography calibration methods which typically assume either close-to-ground ambient barometric pressure conditions or which acquire a single barometric pressure measurement or data point upon startup of the system, and then perform all subsequent measurements based on that baseline value. The present system, however, continuously takes new barometric pressure readings during each NDIR reading, and then calibrates the carbon dioxide sensor based on both the barometric pressure reading and the NDIR reading, in order to obtain the most accurate partial pressure of $CO_2$ measurement possible for accurate prediction, detection and possibly prevention or treatment of dangerous conditions.

The preferred oxygen sensor is sinusoidally modulated, with blue light from a laser diode that excites an orange ruthenium-based dye. The $O_2$ sensor is preferably used to measure the partial pressure of oxygen of the subject's breath. The partial pressure of oxygen is preferably measured using the principle of collisional fluorescence quenching. A ruthenium-based dye is excited by light in the visible blue spectrum and emits light in the orange spectrum. Oxygen interferes with the excitation of the ruthenium-based dye, quenching the intensity of the emission and increasing the fluorescence lifetime. Intensity and fluorescence lifetime are a function of the collisional rate of oxygen molecules with the dye, which is a function of partial pressure of oxygen and the temperature. In order to isolate partial pressure, which is the quantity of interest, temperature compensation is employed, and the dye fluoresces orange light that is phase-shifted relative to the excitation light, and the degree of phase shift is proportional to the oxygen concentration.

More preferably, the sensor is a 465 nm LED (or a 405 nm or 445 nm Laser Diode(LD)) driven by a constant-current driver (in case of laser diode—this becomes a photocurrent-feedback automatic power control driver). The light source is driven by a 40 kHz square wave, preferably operating at a 50% duty cycle. The square wave is gated at 10 Hz, and preferably operating at a 10% duty cycle, resulting in a total on time of 10 ms per duty cycle. The modulated light is preferably turned off during the remaining 90 ms of the duty cycle to reduce photo bleaching, reduce calibration drift, and to save power. The LED or LD is positioned across from an optical dielectric or colored glass longpass filter (550 nm) with a high optical density (at least 4). The LED or LD is separated from the colored glass filter by a distance that allows the divergent beam to fully illuminate the exposed surface of the filter. The side of the filter proximal to the flow channel is coated with a thin layer of ruthenium-based dye. As a result, the dye is exposed to the exhaled air and excited by the LED or LD. Preferably, the emitted light that scatters toward the filter passes through the filter and is detected by a photodiode. A trans impedance amplifier amplifies the photocurrent from the photodiode. Since the photodiode is unbiased, the amplifier requires careful lag compensation. The amplifier output voltage is conditioned by a second-order low-pass filter (45 kHz) and sampled by an analog-to-digital converter at 500 kHz preferably ten times a second, 10 ms at a time.

Preferably, the sampled photocurrent waveform is processed on board a microprocessor or processor with a fast Fourier transform. The magnitude spectrum yields the average intensity, and the phase spectrum yields the phase shift at 40 kHz. The fluorescence lifetime is computed from the tangent of the phase shift at 40 kHz. The average intensity, fluorescence lifetime, and temperature are plugged into a polynomial computed using the method of least squares. This polynomial is computed by calibrating the sensor's outputs to gases with a known and controlled temperature and oxygen partial pressure.

Preferably a small thermistor may be thermally coupled to the dye-coated long pass filter and interfaced to a measurement circuit. The measurement circuit includes a bridge and a timer that samples the thermistor resistance for a short time at a rate of 10 Hz, reducing self-heating effects.

In some embodiments, the oxygen sensor may be a pulse-oximeter modified or adapted to be applied someone on the subject's body of one of the varieties described herein. In other embodiments a pulse-oximeter may be employed separately from the above described oxygen sensors. Traditional pulse-oximeters are clipped onto the subject's finger; however, such configuration would be likely to interfere with the subject's dexterity and use of his or her hands, which is entirely undesirable in applications for which the present invention is designed. Therefore, the optional pulse-oximeter is preferably designed to be attached to the subject's body to measure oxygen saturation in some other area, for example, somewhere on the subject's head, such as in the cup of the subject's ear. A pulse oximeter may be used in place of the above described oxygen sensors, or may be used in addition thereto.

The preferred oxygen sensor is further preferably modular in nature, using a beam focusing assembly used to concentrate and focus the beam of blue light, and with a predetermined optimal distance required between the focusing assembly and the dyed disk. Historically, optical $O_2$ sensors have utilized fiber optic coupling of the blue laser diode and the ruthenium-coated disc. This has caused such typical $O_2$ sensors to be somewhat bulky. The present invention, however, preferably miniaturizes the $O_2$ sensor by removing the fiber optic coupling and thus removing a typical large component of $O_2$ sensors, which are the 90° mirror used for directing the light, along with the fiber optic cable. Removing these components allows the sensor to be constructed much smaller, and thus be better able to fit into a wearable system. Like the LED for the $CO_2$ sensor, blue laser technology has come a long way since the original build. A blue laser diode is now commonly available thanks to Blu-ray players. The result is a much cheaper and smaller technology.

Preferably, the oxygen sensor has a response time of less than 30 seconds. More preferably, the oxygen sensor has a response time of less than 15 seconds. Still more preferably, the oxygen sensor has a response time of less than 5 seconds. Even still more preferably, the oxygen sensor has a response time of less than 1 second. Even more preferably, the oxygen sensor has a response time of less than 500 milliseconds. Still more preferably, the oxygen sensor has a response time of less than 250 milliseconds. Yet more preferably, the oxygen sensor has a response time of less than 100 milliseconds. Still yet more preferably, the oxygen sensor has a response time of less than 50 milliseconds. Even yet more preferably, the oxygen sensor has a response time of less than 30 milliseconds.

Preferably, the oxygen sensor has a sampling rate of at least 10 Hz. More preferably, the oxygen sensor has a sampling rate of at least 15 Hz. Even more preferably, the oxygen sensor has a sampling rate of at least 20 Hz. Still more preferably, the oxygen sensor has a sampling rate of at least 25 Hz. Even still more preferably, the oxygen sensor has a sampling rate of at least 30 Hz.

Preferably, the oxygen sensor has an effective measurement range for partial pressure of oxygen of at least 0.0001 mmHg to 25 mmHg. More preferably, the oxygen sensor has an effective measurement range for partial pressure of oxygen of at least 0.0001 mmHg to 50 mmHg. Even more preferably, the oxygen sensor has an effective measurement range for partial pressure of oxygen of at least 0.0001 mmHg to 100 mmHg. Yet more preferably, the oxygen sensor has an effective measurement range for partial pressure of oxygen of at least 0.0001 mmHg to 250 mmHg. Even yet more preferably, the oxygen sensor has an effective measurement range for partial pressure of oxygen of at least 0.0001 mmHg to 500 mmHg. Still even more preferably, the oxygen sensor has an effective measurement range for partial pressure of oxygen of at least 0.0001 mmHg to 750 mmHg. Even still more preferably, the oxygen sensor has an effective measurement range for partial pressure of oxygen of at least 0.0001 mmHg to 1000 mmHg.

The preferred temperature sensor for measuring temperature of the breathing mix, inhaled breath, or exhaled breath is a typical thermistor known to those skilled in the art. However, an innovative housing and deployment assembly allows the temperature to be placed directly in the flow of the breathing mix along with a flow meter, alone in the flow of the breathing mix, or also in the flow of inhaled or exhaled breath. The housing for the temperature sensor is preferably adaptable to attach in-line with the breathing tube for airflow applications. In other words, when the temperature sensor is used to measure the temperature of the breathing mix as it travels through the breathing tube towards the subject's breathing mask, the housing connects in-line with that breathing tube, thus placing the temperature sensor in the direct flow of the breathing mix. Such a breathing mix temperature sensor may be placed at the distal end of the breathing tube, or at the proximal end, thus effectively attaching to both the breathing tube and mask, or in series with the proximal end of the tube and other modular sensors. The housing may also be attached to the breathing mask on the exhaled breath side, thus measuring the temperature of the exhaled breath. Alternatively, temperature sensors may be placed in any combination of these locations, thus measuring the temperature of the breathing mix, inhaled breath, and/or exhaled breath in any combination. Additionally, temperature sensors of any variety known to those of skill in the art may be included to measure ambient temperature of the environment surrounding the subject. Ambient temperature sensors are particularly useful and important for underwater, and more particularly diver, applications where the temperature of the surrounding water may have a significant and immediate impact on the subject's core body temperature, metabolic rate, and overall health condition.

The temperature sensor housing, while being adaptable to all varieties of breathing tube and mask systems, preferably employs a system of at least one airflow separator. More preferably, the temperature sensor housing employs at list two airflow separator discs with a space in between. The thermistor is then attached to the outside of the housing, with the resistor extending into the center of the housing, preferably on the proximal side of the preferably one air flow separator disc, or between the preferably two air flow separator discs. Thus, the housing deploys the resistor, the temperature measurement portion of the thermistor, into the direct flow of the air or breathing mix to measure the temperature of that particular gas flow.

Additional temperature sensors as described, or other varieties of temperature sensors known to those skilled in the art, may be included to measure various other temperatures related to the subject and the surrounding environment. Thus, in addition to inhaled and exhaled breath temperatures, other temperatures may be measured as well. A direct measurement of the subject's core body temperature may be taken, or may be calculated based on the inhaled and/or exhaled breath temperatures. Interior ambient temperatures may be measured in cabin, cockpit, or other such vehicle-employed systems, as well as exterior ambient temperatures, or those outside of the cabin, cockpit, or the like. For diving applications, temperature sensors may be included to measure ambient water temperature. In other words, temperature sensors may be included to measure the temperature of all gases inhaled or exhaled by the subject, as well as any environmental or ambient temperatures surrounding the subject, such that the conditions surrounding the subject may be known and used to help monitor the subject's and system's statuses, as well as to detect or predict and mitigate or treat dangerous breathing or other health conditions, and to help alert the subject or third party.

Many embodiments of the present invention further employ at least one pressure sensor. Pressure sensors may be included inside a breathing mask to measure in-mask pressure. Measuring in-mask pressure allows the system to obtain various measurements and metrics that help determine the subject's condition, such as work of breathing which becomes very important during high pressure (e.g., high g-force or deep water) environments. Preferably, in-mask pressure sensors are punctureless sensors in that they can be mounted in the mask without the need to punch holes or otherwise permanently modify the mask unit. This punctureless sensor allows the mask to be returned to service in other areas where the in-mask sensor may not be required. One example of an in-mask pressure sensor that can be installed in such a manner is where the pressure sensor is coupled with or installed in the same opening as a microphone that is already installed, or able to be installed, into the mask. Thus, the pressure sensor is able to measure the differential in-mask pressure without requiring its own port or any modification to the mask itself. Pressure sensors may also be included in the subject's gear or clothing, for example a dive suit or a flight vest. Vest or gear or clothing pressure becomes particularly important with regard high altitude, low pressure environments, such as pilots, aircrew, spacecraft crew, and the like. Many embodiments of the present invention are designed to be used in very low pressure environments, such as those just listed. In such environments, pressurized gas is often delivered to the subject through such a facemask. In order to actually breathe said gas, the subject often requires clothing or gear (e.g., flight vest) to provide counterpressure against the lung pressure created by the pressurized gas delivery. Such counterpressure is absolutely necessary in environments above what is known as the Armstrong Line, which is approximately located an altitude of 12 miles above sea level (between 18,900 to 19,350 meters), and which represents the altitude above which atmospheric pressure is so low that humans absolutely require a pressurized environment to survive. The pressure gradient created by the pressurized environment is what allows the human lungs to perform their function and for breathing to occur. In other words, the required pressure gradient, which is the difference between lung pressure and absolute pressure around the subject, is supplemented or created by the clothing or gear in some embodiments. Thus, pressure sensors in the subject's gear or clothing in such environments allows the system to monitor the subject's breathing conditions and detect or predict if the pressure gradient is sufficient to allow healthy breathing. If an insufficient pressure gradient is detected, the system may then prevent or mitigate the onset of dangerous breathing or other health conditions by adjusting the in-mask pressure, vest pressure, or ambient temperature accordingly.

Other pressure sensors may also be included to measure ambient pressure surrounding the subject. Preferably, pressure sensors used for measuring mask and/or vest or clothing pressure are gauge pressure sensors. Gauge pressure sensors, as known to those skilled in the art, are those in which the pressure of the desired space or area is referenced against ambient pressure, and the differential between the two spaces is measured. Thus, in the case of a pilot in flight, the sensor for measuring either mask pressure or vest pressure is preferably a gauge pressure sensor comprising at least two channels for air intake, one open to the pilot's mask or flight vest, and the other channel open to the ambient, in-cabin pressure surrounding the pilot. The differential between the mask or flight vest pressure and the ambient in-cabin pressure is measured to determine the mask or vest pressure. The same or similar sensors might be used to measure mask or clothing/gear pressure for other subjects as well, firefighters, first-responders, rotorcraft pilots and crew, other fixed wing aircraft crew, or any other subject utilizing such clothing, equipment or gear. Breath-by-breath calculations require accurate start and end points for each inhalation and exhalation. While inhalation and exhalation traces, as well as gas partial pressure traces, can be used to estimate these fiducial points, the low flows that occur at the start and end of a breath inherently blur these boundaries. Measuring mask pressure allows for the most accurate estimation of breath timing. The pressure signal is inherently very low-noise, and the valve cracking pressures are stark signal features that indicate breath start and stop times. The present invention preferably utilizes a mask tap device that interfaces a manifold with the communications microphone through vented screws. This retrofit allows for a puncture-less mask pressure tap. In addition to breath timing, the mask pressure signal can indicate valve blockages or insufficient compensation pressure. For example, the mask pressure signal can indicate that the user is attempting to exhale but is prevented from doing so due to a blocked valve, or that the user is attempting to inhale, but the supply is providing insufficient pressure to meet the demand, resulting in additional work of breathing that is not accounted for in other systems.

Still other pressure sensors may also be included. Many embodiments may comprise at least one pressure sensor for measuring ambient pressure separately from any user-related pressure. Such ambient pressure sensors may be used to separately measure cabin pressure for aircraft and vehicles), ambient air pressure (for man-mounted systems utilized by subjects on the ground or in non-pressurized vehicle cabins), ambient water pressure for divers, and the like. Typically, such sensors are absolute pressure sensors. Absolute pressure sensors are known to those skilled in the art to measure the differential between the measured atmospheric pressure and a sealed atmospheric channel within the sensor. Preferably, the sealed channel, or internal vacuum reference chamber, in the sensor is substantially set to about 1 atmosphere (atm), which is equal to about 1013.25 millibar (mbar). 1000 mbar is approximately the standard air pressure at sea level. Thus, the measured ambient pressure is compared against the sealed channel's set pressure, and the measured differential between the two is the absolute pressure surrounding the subject. In many embodiments, gauge pressure sensors and absolute pressure sensors may be used in conjunction with each other to create a more complete pressure profile for the user and his or her environment. Such pressure measurements can then be used, either alone or in conjunction with the measurements and recordings of the other sensors described herein, to help monitor the subject's status, to help detect and predict the onset of dangerous breathing or other health conditions, to mitigate or prevent the onset of such conditions and their symptoms by triggering a warning or alarm to the user or a third party, or triggering automated or semi-automated measures such as initiating backup oxygen or breathing mix supplies, and the like.

Pressure sensors used with the present invention preferably require low power, and are capable of operating accurately and repeatably in extreme conditions (e.g., high pressure, high temperature, low temperature, etc.). The preferred pressure sensors are piezoresistive in nature. Pressure sensors used in the present invention may be of virtually any type known to those skilled in the art (e.g., Honeywell TruStability® series pressure sensors). If such commercially available sensors are used, they are either altered or repackaged in a housing as described herein to become modular, and readily adaptable for use in the various breathing systems and environments for which the present invention is intended to be used. Such housings containing the sensors are then able to be attached to, combined with, or integrated into breathing systems either as part of the construction of said system, or as a retrofit onto an existing system. With regard to the environments in which such sensors are used, as is known to those skilled in the art, pressure decreases as altitude increases. Preferably, for ground or air applications, the pressure sensors used have an effective measurement range of at least +/−1000 mbar. More preferably, for ground or air applications, the pressure sensors used have an effective measurement range of at least +/−900 mbar. Still more preferably, for ground or air applications, the pressure sensors used have an effective measurement range of at least +/−800 mbar. Yet more preferably, for ground or air applications, the pressure sensors used have an effective measurement range of least +/−700 mbar. Even more preferably, for ground or air applications, the pressure sensors used have an effective measurement range of least +/−600 mbar. Still yet more preferably, for ground or air applications, the pressure sensors used have an effective measurement range of least +/−500 mbar. Even yet more preferably, for ground or air applications, the pressure sensors used have an effective measurement range of least +/−400 mbar. Yet still more preferably, for ground or air applications, the pressure sensors used have an effective measurement range of least +/−300 mbar. Even still more preferably, for ground or air applications, the pressure sensors used have an effective measurement range of least +/−200 mbar. Most preferably, for ground or air applications, the pressure sensors used have an effective measurement range of at least +/−100 mbar.

Conversely, for underwater applications, pressure increases as the subject increases his or her depth, and thus pressure is measured differently than for air applications; however, these sensors still operate on the same principles. Preferably, for underwater applications, the pressure sensors used have an effective measurement range of least +/−1000 mbar. More preferably, for underwater applications, the pressure sensors used have an effective measurement range of least +/−2000 mbar. Still more preferably, for underwater applications, the pressure sensors used have an effective measurement range of least +/−4,000 mbar. Yet more preferably, for underwater applications, the pressure sensors used have an effective measurement range of least +/−8,000 mbar. Even more preferably, for underwater applications, the pressure sensors used have an effective measurement range of least +/−12,000 mbar. Still yet more preferably, for underwater applications, the pressure sensors used have an effective measurement range of least +/−16,000 mbar. Even yet more preferably, for underwater applications, the pressure sensors used have an effective measurement range of least +/−20,000 mbar. Yet still more preferably, for underwater applications, the pressure sensors used have an effective measurement range of least +/−25,000 mbar. Even still more preferably, for underwater applications, the pressure sensors used have an effective measurement range of least +/−30,000 mbar. Still even more preferably, for underwater applications, the pressure sensors used have an effective measurement range of least +/−35,000 mbar. Yet even more preferably, for underwater applications, the pressure sensors used have an effective measurement range of least +/−40,000 mbar. Still even yet more preferably, for underwater applications, the pressure sensors used have an effective measurement range of least +/−45,000 mbar. Even still yet more preferably, for underwater applications, the pressure sensors used have an effective measurement range of least +/−50,000 mbar. Yet still even more preferably, for underwater applications, the pressure sensors used have an effective measurement range of least +/−55,000 mbar. Even yet still more preferably, for underwater applications, the pressure sensors used have an effective measurement range of least +/−60,000 mbar. Most preferably, for underwater applications, the pressure sensors used have an effective measurement range of least +/−65,000 mbar.

Many of the sensors included or used with the present invention benefit from or require temperature control of the sensor itself in order to perform properly, in particular the preferred oxygen sensor described herein. Controlling the temperature of the optical sensors allows the system to achieve higher efficiency and more accurate and sensitive measurements while simultaneously preventing environmental problems that arise during use, for example condensation on the optical surfaces and thermal drift of the sensor readings. Issues such as these arise in applications where a particularly high concentration of a gas is present and in environments where extreme temperatures exist, and lead to inaccurate, and potentially dangerous sensor measurements. As an example of the effect such conditions have on optical sensors, ruthenium-based oxygen sensors, such as described herein, tend to lose sensitivity at high concentrations of oxygen or at high temperatures. Therefore, in environments such as those the present invention is concerned with, where a gas source or generator (e.g., oxygen tank, OBOGS, or the like) provides a high concentration of oxygen, and thus decreases the sensitivity of the sensor. However, by chilling or cooling a ruthenium-based (or other similar fluorophore-based) sensor, the measurement sensitivity curve of the sensor shifts and allows the sensor to more accurately measure the higher concentrations of oxygen. Conversely, if the sensor is warmed or heated, then the measurement sensitivity curves shifts in the opposite direction. Thus, warming such a sensor would allow for more accurate measurements at exceedingly low oxygen concentrations. Although the individual sensor temperature control is described in terms of a ruthenium-based oxygen sensor, the same concept may be applicable to oxygen sensors using other similar fluorophores as well, or for other sensors such as carbon dioxide sensors. The goal of the temperature control system is to balance the temperature with the concentration of the gas being measured in order to maintain the highest sensitivity of the sensor possible so that the sensors are able to measure smaller changes in the gas concentration and provide more robust measurements and predictions of dangerous breathing or other health conditions.

As noted above, gas concentration is not the only factor that affects the sensor measurements or readings that may be dealt with by controlling the temperature of the sensors. Often, condensation can build up on the optical surfaces and cause errors, artifacts, or other generally inaccurate measurements. However, controlling the temperature of the optical sensors, and particularly the optical surfaces thereof, allows the system to reduce, eliminate and even prevent condensation from building up on those surfaces, and thus maintain the most efficient and accurate measurements possible. This system allows the present invention to operate in very humid (thus highly likely to allow atmospheric moisture to condense on the optical surfaces) environments, where no other existing system can presently operate with the same accuracy. Thus, by controlling the temperature of the optical sensors, preferably the optical sensors are capable of operating and accurately measuring in environments of 25% humidity or greater. More preferably, the optical sensors are capable of operating and accurately measuring in environments of 50% humidity or greater. Still more preferably, the optical sensors are capable of operating and accurately measuring in environments of 60% humidity or greater. Yet more preferably, the optical sensors are capable of operating and accurately measuring in environments of 75% humidity or greater. Even more preferably, the optical sensors are capable of operating and accurately measuring in environments of 85% humidity or greater. Still yet more preferably, the optical sensors are capable of operating and accurately measuring in environments of 90% humidity or greater. Yet still more preferably, the optical sensors are capable of operating and accurately measuring in environments of 92% humidity or greater. Even still more preferably, the optical sensors are capable of operating and accurately measuring in environments of 94% humidity or greater. Still even more preferably, the optical sensors are capable of operating and accurately measuring in environments of 96% humidity or greater. Yet even more preferably, the optical sensors are capable of operating and accurately measuring in environments of 98% humidity or greater. Most preferably, the optical sensors are capable of operating and accurately measuring in environments of 100% humidity.

In order to provide such temperature control for sensors, such embodiments preferably include a temperature controller for adjusting and maintaining the temperature of the various optical sensors. Various embodiments may utilize a single temperature controller, or there may be multiple, individual controllers for the various components of the system. Preferably, multiple temperature controllers are used to give more accurate and specific control of the temperature of the various components. The temperature controllers may take any form that is able to change the temperature of the various components with a high degree of accuracy and consistency to avoid temperature drifting, for example a highly efficient thermoelectric cooler or heater. By way of non-limiting example, one embodiment of the present invention may include three such temperature controllers in a breathing-mask system. In this example, the mask comprises an inhaled-side oxygen sensor, and both a second oxygen sensor and a carbon dioxide sensor on the exhaled-side, as well as three temperature controllers. One temperature controller is used to control the temperature of the Ruthenium dye of the inhaled-side oxygen sensor. Controlling the temperature of the dye allows the system to shift the sensitivity of the sensor based on the concentration of oxygen present in order to maintain the balance between oxygen and temperature and ensure that the sensor is operating at a highly sensitive level. On the exhaled-side oxygen sensor, one temperature controller is used to control the temperature of not only the Ruthenium dye of the sensor, which is performed in much the same manner as the inhaled-side oxygen sensor, but also the photodiode. The photodiode of the exhaled-side oxygen sensor is preferably temperature controlled because it can tend to exhibit shifting wavelengths of light based on the temperature, which can lean to inconsistent or inaccurate measurement of the various signals (described in greater detail below) that are measured on the exhaled-side but not the inhaled side. The wavelength shift on the inhaled side can be accounted for with a basic temperature measurement and calibration without requiring control of the temperature of the diode. For the exhaled-side oxygen sensor, the actual temperature of the photodiode is relatively irrelevant, so long as it remains constant. Therefore, this exemplary embodiment uses a single temperature controller for both the dye and the diode of the exhaled-side oxygen sensor so that both are maintained at the same temperature that allows the sensor to be as sensitive as possible while merely maintaining a steady temperature for the diode to ensure a constant emission wavelength. Thus, the entire sensor can be maintained at the highest sensitivity and accuracy as possible. Lastly for this exemplary embodiment, a third temperature controller is used to control the temperature of the photodiode for the exhaled-side carbon dioxide sensor, also in order to maintain a constant emission wavelength for consistency, accuracy and sensitivity of the sensor.

As noted above, the exhaled-side sensors of various embodiments of the present invention may perform a more complex set of functions beyond merely taking a measurement of the respective gas concentration. Effectively, these sensors may obtain a series of three or more separate signals or measurements in order to provide a single gas concentration measurement value that is accurate and accounts for the various environmental and controlling effects (e.g., temperature control as described above) being placed on the exhaled-side sensors. A gas concentration measurement is taken, and is then effectively calibrated or adjusted based on the adjustments to the sensors by a set of two other signals or measurements that can be referred to as a background signal and a reference signal. By way of non-limiting example, using the exhaled-side oxygen sensor of one embodiment of the present invention, a basic oxygen measurement with the oxygen sensor is obtained using a blue diode to excite the ruthenium dye, then a second measurement is obtained with no light being shined, and then a third measurement is obtained where a red light of known wavelength that may be situated near the ruthenium dye is shone back through the gas flow. The blue light measurement is just as described above with regard to normal oxygen sensor function and provides an oxygen measurement ($O_2$ Sig) of the gas being exhaled. The second measurement with no light emission is the background signal (Bkg) which represents the background or ambient light present in the sensor, and the third measurement with the red light is the reference signal (Ref) which represents a specifically known value that is not affected by the gas in the gas flow chamber. Thus, with these three measurements, the system can provide an oxygen concentration value that is calibrated for background light and condensation by calculating the ratio shown in equation 4:

$$\frac{O_2 \text{ Sig} - Bkg}{Ref - Bkg} \qquad 4)$$

Thus, in this example, the calibrated oxygen concentration value is more accurate and takes into account the environmental factors (e.g., ambient light) and controlling factors (e.g., wavelength of excitation light and dye from temperature control) to provide a more accurate and precise measure.

The optical sensor components are preferably placed in mechanical attachment housings for each of the different sensors, or combinations thereof. These sensor housings are used to secure the oxygen, carbon dioxide, and other sensors to the facemask or in-line with the breathing tube, and are preferably optimized for size and weight and are machined and fabricated of performance materials capable of withstanding conditions of extremely high pressure, extremely low pressure, torque, g-forces, high and low temperature, and the like. The sensors are all preferably man-mounted, that is, in some way attached or affixed to the user or his or her gear or clothing, as opposed to being vehicle- or otherwise externally-mounted. Further preferably, the sensors are each g-force-insensitive in that they are not affected, nor is their function, by high g-force environments. Many embodiments of the present invention utilize a strain relief system whereby any mechanical connections between sensors and the system or interior to the sensors themselves are reinforced so that under high g-forces the mechanical connections will not pull apart and separate. Another way to ensure accuracy is to use solid state sensors with no moving parts that would be affected by such environments. The housings are preferably flexible though rigid. Such materials may include, but are not limited to plastics (list types of plastics), rubber (types of rubber), or the like. The sensor housings are preferably designed to be modular and adaptable to be retrofitted onto virtually all existing and later developed breathing masks and breathing tube systems. The housings and sensors may also be deployed in a self-contained system without being adapted to or attached to an existing system. In many embodiments, the various sensors of the present invention may be combined, packaged or enclosed in such attachment housings together to minimize the number of housings, modules, and/or attachments that might be required to perform the necessary measurements. By way of non-limiting example, in one preferred embodiment, an oxygen sensor and a carbon dioxide sensor are housed together in a single enclosure or attachment housing, this creating a single sensor unit, which is then attached to the exhalation side of the mask. Thus, the single exhaled-side sensor unit comprises both the oxygen and carbon dioxide sensors which measure their respective gas concentrations as the user exhales without requiring multiple enclosures which would be more bulky and cumbersome. A person having ordinary skill in the art will understand which sensors may realistically and conveniently be housed together while neither impeding the function of the individual sensors or the system as a whole. Further, the sensors and sensor housing are all preferably miniaturized in order to decrease the weight of the system as a whole and to make it easier for the subject to wear for longer periods of time with minimal discomfort and draining of energy.

The flow sensor is preferably a micro-electromechanical systems (MEMS) hot-film anemometer. The flow sensor may be of a type readily available and known to those in the art, for example, a commercial off-the-shelf flow sensor from Honeywell (e.g., Honeywell AWM700 series Airflow sensors). Such a commercial flow sensor is repackaged into an innovative housing to fit into the breathing mask hose, in a manner similar to the temperature sensor housing described above. The flow sensor may also be of other varieties known to those in the art, such as turbine sensors, other MEMS-based sensors, ultrasonic sensors, and the like. As such, the flow sensor is preferably placed at the distal end of the breathing tube. For example, in a typical flight system, such as a combat pilot breathing mask, the flow sensor would be situated between the distal end of the breathing tube and the typical CRU94 or other inhaled regulator fitting which provides pressure breathing to the aircrew wearing the mask. Alternatively, the flow sensor may be adapted to fit inside the breathing tube. Optionally, the repackaged housing contains flow dividers that create a small pressure drop across the sensor, separating the flow into two separate channels: one a bypass channel with no sensor, and the other being a measurement channel whereby the gas flows over the flow sensor. By way of non-limiting example, in one embodiment utilizing a flow sensor (such as the Honeywell model #AWM720P1 flow sensor) rated for an effective measurement range of 0-200 ALPM (actual liters per minute) or SLPM (standard liters per minute), and where the gas flow rate is about 400 liters per minute (LPM), the sensor would be unable to effectively record measurements at such a high flow rate. However, the flow sensor divider separates the flow such that approximately 200 LPM flows through each of the bypass channel and the measurement channel, whereby measurements are taken at 200 LPM and the data is then extrapolated back to a 400 LPM flow rate. The sensor outputs an analog voltage of preferably 0-5V which is a nonlinear function of the mass flow rate of air, calibrated in standard liters per minute. Preferably, the sampling rate of the flow sensor greater than about 10 Hz. More preferably, the sampling rate of the flow sensor greater than about 25 Hz. Still more preferably, the sampling rate of the flow sensor greater than about 35 Hz. Yet more preferably, the sampling rate of the flow sensor greater than about 50 Hz. Even more preferably, the sampling rate of the flow sensor greater than about 65 Hz. Still yet more preferably, the sampling rate of the flow sensor greater than about 75 Hz. Even yet more preferably, the sampling rate of the flow sensor greater than about 90 Hz. Yet still more preferably, the sampling rate of the flow sensor greater than about 100 Hz. Even still more preferably, the sampling rate of the flow sensor greater than about 115 Hz. Yet even more preferably, the sampling rate of the flow sensor greater than about 125 Hz. Still even more preferably, the sampling rate of the flow sensor greater than about 140 Hz. Yet even still more preferably, the sampling rate of the flow sensor greater than about 150 Hz. Most preferably, the sampling rate of the flow sensor greater than about 175 Hz. The true effective upper frequency range of the flow sensor is, in practice, limited by the frequencies of the other sensors employed in a particular embodiment. Also, with regard to the effective measurement range, preferably the flow sensor has an operating range of 0-50 SLPM or ALPM. More preferably, the flow sensor has an operating range of 0-100 SLPM or ALPM. Yet more preferably, the flow sensor has an operating range of 0-150 SLPM or ALPM. Even more preferably, the flow sensor has an operating range of 0-200 SLPM or ALPM. Still even more preferably, the flow sensor has an operating range of 0-250 SLPM or ALPM. Even yet more preferably, the flow sensor has an operating range of 0-300 SLPM or ALPM. Yet still more preferably, the flow sensor has an operating range of 0-350 SLPM or ALPM. Most preferably, the flow sensor has an operating range of 0-400 SLPM or ALPM.

Different types of sensors for measuring physiological signals from the subject can be used preferably when these sensors can be incorporated into a facemask. These sensors include electrodes for measuring electro-physiological signals such as EEG, ECG, EMG, ENG, ERG, EOG and the like. These electro-physiological signals can be obtained by any method known in the art, and are envisioned to cover those sensors subsequently developed by those skilled in the art to detect these types of signals.

For example, the sensors can be magnetic sensors. Since electro-physiological signals are, in general, electrical currents which produce associated magnetic fields, the present invention further anticipates methods of sensing those magnetic fields to acquire brain wave signals similar to those which can be obtained through, for example, an electrode applied to the subject's scalp. The subject(s) referred to in the present invention can be any form of animal. Preferably the subject(s) are mammal, and most preferably human.

If electrodes are used to pick up the electro-physiological signals, these electrodes for example when measuring brain wave or EEG signals may be placed at one or several locations on the subject(s)' scalp or body—preferably on the forehead or around the face so they can be incorporated into the facemask. The electrode(s) can be placed at various locations on the subject(s) scalp and preferably the forehead in order to detect EEG or brain wave signals. In order to obtain a good EEG or brain wave signal it is desirable to have low impedances for the electrodes. Typical EEG electrodes connections may have an impedance in the range of from 5 to 10 K ohms. It is in generally desirable to reduce such impedance levels to below 2 K ohms. Therefore, a conductive paste or gel may be applied to the electrode to create a connection with an impedance below 2 K ohms. Alternatively or in conjunction with the conductive gel, the subject(s)' skin may be mechanically abraded, the electrode may be amplified or a dry electrode may be used. Dry physiological recording electrodes of the type described in U.S. Pat. No. 7,032,301 are herein incorporated by reference. Dry electrodes provide the advantage that there is no gel to dry out, no skin to abrade or clean, and that the electrode can be applied in hairy areas such as the scalp. Additionally if electrodes are used as the sensor(s), preferably at least two electrodes are used—one signal electrode and one reference electrode; and if further EEG or brain wave signal channels are desired, the number of electrodes required will depend on whether separate reference electrodes or a single reference electrode is used. For the various embodiments of the present invention, preferably an electrode is used and the placement of at least one of the electrodes is at or near the occipital lobe of the subject's scalp. Preferably, in various embodiments these dry electrode sensors are connected to or embedded in the facemask.

If electrodes are used to pick up the electro-physiological signals, these electrodes for example when measuring cardiac signals using an ECG, may be placed at specific points on the subject's body. The ECG is used to measure the rate and regularity of heartbeats as well as the size and position of the chambers, any damage to the heart and in diagnosing sleeping disorders. As the heart undergoes depolarization and repolarization, electrical currents spread throughout the body because the body acts as a volume conductor. An ECG is important as a tool to detect the cardiac abnormalities that can be associated with respiratory-related disorders. The electrical currents generated by the heart are commonly measured by an array of preferably not more than 10 electrodes, placed on the body surface. Preferably electrodes are placed on each arm and leg, and six electrodes are placed at defined locations on the chest. The specific location of each electrode on a subject's body is well known to those skilled in the art and varies amongst individual and different types of subjects. Although a full ECG test usually involves ten electrodes, only two are required for many tests such as a sleep study. These may be placed on the subject's left-hand ribcage, under the armpit and on the right-hand shoulder, near the clavicle bone, or in other convenient locations on either side of the subject's body. These electrode leads are connected to a device contained in the signal-processing module of the present invention that measures potential differences between selected electrodes to produce electro-cardiographic tracings.

There are two basic types of ECG leads: bipolar and unipolar. Bipolar leads (standard limb leads) utilize a single positive and a single negative electrode between which electrical potentials are measured. Unipolar leads (augmented leads and chest leads) have a single positive recording electrode and utilize a combination of the other electrodes to serve as a composite negative electrode.

Other sensors can be used to measure various parameters of a subject's physiological condition. These other parameters are preferably measured using sensors or devices such as a photodetectors, accelerometers, pneumotachometers, strain gauges, thermal sensors, transducers, piezo sensors, magnetometers, pressure sensors, static charge-sensitive beds, audio monitors, video monitors and the like. Since the system is programmable potentially any transducer type sensor, that is any sensor that outputs an electrical signal, can be used with the system.

Accelerometers may be used to measure determine the subject's body position and orientation, g-forces, and provide other functions such as providing time synchronization with the subject's vehicle (e.g., aircraft). Such accelerometers may be of any type known to those skilled in the art, including magnitude accelerometers and 3-axis accelerometers. Accelerometers are often included to detect high g-force conditions, and thus to help monitor, predict, mitigate and alert the user or a third party as to the onset or occurrence of dangerous breathing or other health conditions as a result of such high g-force condition or maneuver. The time synchronization feature primarily allows for post-mission, or post-application review of data in which the subject's position and orientation, as well as g-forces experienced are compared via time signature to known events or occurrences, such as detected dangerous breathing or other health conditions. This helps to align data points in order to allow and facilitate analysis of what circumstances may lead to or cause the onset of dangerous breathing or other health conditions in order to help develop new preventative, mitigating, or treatment systems and methods.

The sensor system of the invention preferably is in communication with a local processor or other electrical components for receiving signals from the sensors and for calculating a number of measures and metrics based at least in part on the signals from the sensors. The processor may be in direct, wired communication with the sensor or sensors. However, communication between the sensors and the processor may be through wireless means. Preferably, the processor is also sufficiently miniaturized to be optimally placed in a contained pocket, sleeve, or the like located on the subject's clothing or in a self-contained system or module. The processor preferably contains and employs an algorithm for the specific purpose of identifying and predicting dangerous health conditions including, but not limited to hypoxia, hypothermia, hypo- and hyperventilation, G-LOC, atelectasis and other dangerous breathing and physical conditions. Preferably, the algorithm in many embodiments identifies or predicts a mass of oxygen absorbed by the subject based at least in part on the signal or signals from the various sensors which may be included with the system. Further preferably, the algorithm then uses the identified or predicted mass of oxygen absorbed to identify or predict the onset of a dangerous health condition in the subject. The processor preferably includes an electronics board and housing, and the processor as a whole is preferably not larger than the volume of a typical flight suit pocket. The processor is further preferably able to relay a signal or warning to the subject, a third party, such as a dive master, team member, or the like, when dangerous conditions, and more preferably dangerous breathing or other health conditions are detected or predicted. Also, in some embodiments involving a closed-loop breathing system, the processor is able to calculate an optimal breathing mix of gases, and to recalibrate the system to provide that breathing mix and thus correct or avoid potentially hazardous breathing conditions, for example by automatically increasing the amount of oxygen provided by the system. Such systems may utilize the in-place OBOGS system and simply increase its output, or may utilize secondary oxygen supply reserve systems, such as bottled gaseous oxygen or liquid oxygen, both of which preferably include a humidification system to avoid drying out of the subject's breathing passageways. The processor, in many other embodiments, further controls oxygen or breathing mix dosing, which is a method of control gas delivery based on perceived, measured, or calculated need and which helps to extend the life of gas supplies. Oxygen or breathing mix dosing is particularly useful for systems comprising reserve or backup gas supplies such that in the event of main or primary gas supply failure, the reserve or backup supply is preserved and extended for as long as possible to maximize the likelihood that the subject is able to return to safety.

The processor of the current system also preferably contains at least one algorithm for substantially identifying or predicting dangerous health conditions, more preferably dangerous breathing or other health conditions based at least in part on the signals received from the connected sensors of the sensor system. Preferably, the algorithm(s) are adaptive in that they are robust, and can monitor numerous physiological and system conditions simultaneously and substantially in real time, and further able to react to changes in the numerous conditions in order to monitor, predict, mitigate, and/or alert the subject or a third party regarding dangerous breathing or other health conditions. Using these algorithms, the processor preferably calculates inhaled and exhaled volumes of oxygen and carbon dioxide, respiratory periods, oxygen saturation, and other related respiratory metrics. Furthermore, the processor may also use these calculated values to determine, identify or predict a dangerous health or breathing condition such as hypoxia, anoxia, hypo/hyperthermia, hypo/hyperventilation, G-LOC, atelectasis and other similar conditions. Preferably once the breathing sensor system identifies or predicts a dangerous breathing condition, the breathing mask sensor system can alert the wearer and/or transmits the biometric information to an external monitoring system. One exemplary embodiment of the dangerous condition prediction algorithm that particularly focuses on hypoxia, in its simplest form, compares the estimated oxygen demand based on demographic factors and workload to the calculated oxygen consumption. These quantities are reduced to an estimate of arterial blood gases, which are thresholded to determine hypoxia risk and alert. However, the algorithms are not a non-invasive replacement for arterial blood gas measurements. Instead, the algorithm estimates, given previous and current conditions, what the blood gas values will trend toward in the future. This is accomplished using a physiological lung model in combination with machine learning models. Specifically, raw signal traces are sliced to represent individual breaths, and each breath is reduced, via numerical integration and multiplication, to the gases produced and consumed. These breath-by-breath values are read into the buffer of a classifier algorithm, which is trained on these data and directly measured blood gas data at the end of a 5-minute epoch at a given altitude. The classifier then uses the respiratory gas calculations to predict subsequent blood gas values. Respiratory and gas exchange patterns that are reflective of healthy or dangerous conditions may be analyzed and classified via a linear lung model or, more preferably, via a machine learning classifier. The machine learning classifier may be based off of a "strong learning" method, such as an artificial neural network, a support vector machine, or a Bayes classifier, which may apply training data from a multitude of individuals to any user. Alternatively, the classifier may be a "lazy learner" that continuously compares a user's respiratory and gas exchange patterns with the measured blood oxygenation levels, creating a unique algorithm for that particular user that improves classification accuracy with continued use. The classifier may rely on a feature space selected by known metabolic metrics. Features for a given breath may include the inspiratory volume, the expiratory volume, the $CO_2$ produced (by mass or analog), the $O_2$ consumed (by mass or analog), the respiration rate, the breath duration, and the peak negative and positive mask pressures. Ambient pressure and peak G loads, as well as G-Load integrals under the appropriate time window can also be considered for the feature vector. Finally, samples of $SpO_2$ and heart rate may be included in the feature vector as well. The breath-by-breath metrics of the feature space most intuitively come from a single breath. However, it may be advantageous to consider multiple breaths at once. These "breath-tuples" may include the features from any discrete number of breaths, for example from 1 breath to 10 breaths. A certain count of breath-tuples can be considered the optimal tradeoff between classification accuracy and time delay. The classifier is preferably trained to $SpO_2$ bins, which are sampled from a time-offset $SpO_2$ trace. The time offset, meant to reflect $SpO_2$ levels in the future, can range from 30 seconds to 3 minutes.

By way of example of this process, the system may predict the onset of G-force induced loss of consciousness (G-LOC) based on a series of measurements of ventilation or flow rate of the subject's breath and carbon dioxide output which allow the system to determine the subject's breath rate and type of breathing the subject is performing. The system can then differentiate between G-LOC and hyperventilation, both of which may exhibit very similar signs and breathing conditions. If the system determines that the subject is about to experience G-LOC, then it can instruct the user to initiate a pre-determined breathing protocol designed to mitigate or prevent G-LOC, specifically where the subject decreases the duty-cycle of his or her breathing and uses very short, high flow breaths that counteract the breathing conditions that lead to G-LOC. In another example, the system may monitor and detect the occurrence of atelectasis, or the collapse, either complete or partial, of the lung or individual alveoli in the lunch, and instruct the user to cough or otherwise alter his or her breathing to force the alveoli back open.

The algorithm(s) utilized by the present invention are designed to provide real-time calculations based at least in part on the signals received from the sensor(s) of the system. In many embodiments of the present invention, the algorithm(s) utilized employ a series of equations developed for prediction of Acute Mountain Sickness (AMS) by Burtscher et al., and adapted to operate in real-time. See Burtscher et al., PREDICTION OF THE SUSCEPTIBILITY TO AMS IN SIMULATED ALTITUDE, 12 Sleep Breath 103 (2008). AMS is also commonly known as Altitude Sickness, and occurs at high altitudes, typically above 8,000 feet, as a result of reduced air pressure and decreased oxygen levels at those altitudes. AMS is essentially similar to and interchangeable with hypoxia in that they both have the same causes and symptoms. The equations developed by Burtscher were designed to first evaluate a subject at low altitude, and then subsequently again high altitude, and for a static comparison to be made between the two measurements or evaluations. However, these equations have been adapted to perform real-time, continued analysis of a subject for the present invention, by converting them from static equations into time dependent equations for measuring oxygen saturation response ($SPO_2$ Response), Hypoxic Cardiac Response (HCR), and Hypoxic Ventilatory Response (HVR). These equations are as follows:

$$SPO_2 \text{ Response}(t) = SPO_{2_{HIGH\ ALT}}(t) - \overline{SPO_{2_{LOW\ ALT}}} \quad 1)$$

$$HCR(t) = \frac{(HR_{HIGH\ ALT}(t) - \overline{HR_{LOW\ ALT}})}{\left(SPO_{2_{HIGH\ ALT}}(t) - \overline{SPO_{2_{LOW\ ALT}}}\right)} \quad 2)$$

$$HVR(t) = \frac{\left(VE_{HIGH\ ALT}(t) - \overline{VE_{LOW\ ALT}}\right)}{\left(SPO_{2_{HIGH\ ALT}}(t) - SPO_{2_{LOW\ ALT}}\right)} \quad 3)$$
(Body Mass)

Blood Oxygen Concentration Response ($SPO_2$ Response) is the most basic of the metrics used to determine and predict the onset of altitude-related dangerous breathing or other health conditions such as hypoxia, AMS<, and the like. $SPO_2$ Response is essentially the real-time measurement of a subject's change in blood oxygen concentration. In equation 1, the oxygen saturation response ($SPO_2$ Response) as a function of time is calculated by first measuring the average constant blood oxygen saturation of the subject at low altitude (ground level), and then subtracting that value from the measured blood oxygen concentration of the subject at high altitudes for any given time point. This measurement and comparison can be made repeatedly and substantially continuously to provide a moment-by-moment profile of the subject's blood oxygen saturation under varying conditions, such as increased altitude, over time. Hypoxic Cardiac Response (HCR) is a metric which is used to determine the effect that a decreased level of blood oxygen concentration has on a subject's heart rate. Equation 2 shows that hypoxic cardiac response is calculated by similarly measuring the average constant heart rate and blood oxygen concentration at low altitudes (ground level), subtracting those values from their respective measured counterpart values at high altitudes, and then dividing the difference in heart rate value by the difference in blood oxygen concentration value. This measurement and comparison can be made repeatedly and substantially continuously to provide a moment-by-moment profile of the subject's hypoxic cardiac response at any given point in time, and thus correlated to the altitude at that time. Hypoxic Ventilatory Response (HVR) is another metric used which relates to the effect that a decrease in blood oxygen concentration has on a subject's ventilation, or the volume of air moved into and out of the subject's lungs in a given amount of time. Equation 3 depicts the calculation of hypoxic ventilator response as a function of time. First, average constant ventilation (VE—volume of air moved in and out of the lungs over time—typically measured in L/min) and average constant blood oxygen concentration are measured at low altitudes (ground level). Then, ventilation and blood oxygen concentration are measured repeatedly and essentially continuously at high altitudes, and the average constant low altitude measurements are subtracted from their respective high altitude counterparts. The difference between the ventilation rates is then divided by the difference between the blood oxygen concentration values, and that product is divided by the subject's body mass. Again, this calculation can be performed repeatedly and essentially continuously, thus providing a moment-by-moment profile of the subject's hypoxic ventilator response at any given point in time, and correlated to the altitude at that given time point. Each of these three equations were adapted to provide a real-time, continuous analysis of the various effects and responses the subject's body experiences by measuring the respective values and performing continuous calculations as above. This is a significant improvement over the typical method of performing separate static measurements and comparing the results at a later time to determine the effect on the subject. The adapted formulas allow for real-time monitoring, detection, prediction, and mitigation of dangerous breathing or other health conditions such as hypoxia and AMS.

Alternatively, instead of including a separate processor, the system may contain electronic components that can perform many of the functions of the processor described above. Preferably, these electronic components can be miniaturized and/or adapted to fit into a single enclosure or housing, which can also, in turn, preferably a miniaturized data acquisition unit. The processor or electronics optionally can comprise one or more electronic components for detecting the physiological signal from the sensor(s). While some of the electronic components such as the battery or antenna may be separate from the other electronic components, and in the case of the antenna may be printed right onto a base or board, which the electronics optionally are mounted onto. The one or more electronic components for detecting the physiological signal from the at least two electrodes is a wireless device, which most preferably transmits the physiological signals to a remote receiving unit. Preferably, the one or more electronic components also filter (and possibly amplify) the detected signal and more preferably convert this detected physiological signal, which is in an analog form into a digital signal for transmission to the remote receiving unit. The one or more electronic components and/or process optionally may be incorporated onto the facemask or in close proximity to the subject. Further preferably, the one or more electronic components can receive a signal from the remote receiving unit or other remote transmitters. The one or more electronic components may include circuitry for but are not limited to for example electrode amplifiers, signal filters, analog to digital converter, RF output antenna, RF input antenna, RF output/input antenna, optical output antenna, optical input antenna, optical output/input antenna, acoustic output antenna, acoustic input antenna, acoustic output/input antenna, subcarrier voltage controlled oscillator (VCO), transmitter VCO, tuning crystal, phase-locked loop, frequency select switches, a DC power source and combinations thereof. The one or more electronic components may comprise one processing integrated circuit, multiple integrated circuits, single function components or combinations thereof, which can perform all of the necessary functions of detecting the sensor or physiological signal(s), transmitting a signal corresponding to the sensor signal(s) to a receiving unit and optionally receiving a signal from a remote transmitter. These one or more electronic components can be assembled on a printed circuit board or by any other means known to those skilled in the art. Preferably, the one or more electronic components can be assembled on a printed circuit board or by other means so its imprint covers an area less than 4 in$^2$, more preferably less than 2 in$^2$, even more preferably less than 1 in$^2$, still even more preferably less than 0.5 in$^2$, and most preferably less than 0.25 in$^2$. The one or more electronic components can be further reduced into discrete components for inclusion into an integrated circuit (IC), or more preferably, an application specific integrated circuit. These integrated circuits may be of any of the type including, but not limited to, analog to digital converters, processors, and other components necessary to lower the cost, reduce the size, weight, and/or power of the present invention. The present invention preferably utilizes switched-mode power supplies where possible to increase the efficiency of the system. In particular, the 2.5V and 10V rails are accomplished via a switched mode power supply and a stacked capacitor configuration respectively. These are important to achieve battery operation and may not be employed by commercial devices meant to draw power from a mains outlet.

Preferably, the circuitry of the one or more electronic components is appropriately modified so as to function with any suitable miniature DC power source. More preferably, the DC power source is a battery. The most preferred battery of the present invention are zinc-air hearing aid batteries. Zinc-air hearing aid batteries offer a high energy density and nearly constant output voltage during discharge, which is preferable. Additionally, these commercially available batteries are readily available and inexpensive. Preferably, a three-cell stack of zinc-air batteries are used, each cell offering a steady 1.2 V, and producing a stable and reliable 3.6 V. Other types of batteries include but are not limited to lithium-polymer and lithium-ion batteries, zinc-air batteries, and the like.

Preferably, the circuitry of the one or more electronic components comprises data acquisition circuitry further including an electrode amplifier which detects the sensor signal(s) and integrates the detected signal(s) into a single signal and amplifies it to some power level. The data acquisition circuitry is designed with the goal of reducing size, lowering (or filtering) the noise, increasing the DC offset rejection and reducing the system's offset voltages. The data acquisition circuitry may be constrained by the requirements for extremely high input impedance, very low noise and rejection of very large DC offset and common-mode voltages, while measuring a very small signal of interest. Additional constraints arise from the need for a "brick-wall" style input protection against ESD and EMI. The exact parameters of the design, such as input impedance, gain and passband, can be adjusted at the time of manufacture to suit a specific application via a table of component values to achieve a specific full-scale range and passband.

More preferably, a low-noise, low power instrumentation amplifier is used. The inputs for this circuitry is guarded with preferably, external ESD/EMI protection, and very high-impedance passive filters to reject DC common-mode and normal-mode voltages. Still preferably, the instrumentation amplifier gain can be adjusted from unity to approximately 100 to suit the requirements of a specific application. If additional gain is required, it preferably is provided in a second-order anti-alias filter, whose cutoff frequency can be adjusted to suit a specific application, with due regard to the sampling rate. Still preferably, the reference input of the instrumentation amplifier is tightly controlled by a DC cancellation integrator servo that uses closed-loop control to cancel all DC offsets in the components in the analog signal chain to within a few analog-to digital converter (ADC) counts of perfection, to ensure long term stability of the zero reference.

Preferably, the physiological signal is converted to a digital form. This can be achieved with an electronic component or processing integrated circuit through the use of an ADC. More preferably, the ADC restricts resolution to 12-bits due to the ambient noise environment in such integrated circuits. Despite this constraint, the ADC remains the preferable method of choice for size-constrained applications such as with the present invention unless a custom data acquisition integrated circuit is used because the integration reduces the total component integrated circuit count and significantly reduces the number of interconnects required on the printed circuit board, which results in smaller size, weight, and power.

Preferably, the circuitry of the one or more electronic components comprises a digital section. Part of this circuitry may include one or more integrated circuits preconfigured to perform some or all of the digital processing for use with existing wireless protocols including but not limited to wireless local area networks (IEEE 802.11 including Wi-Fi), wireless personal area networks (IEEE 802.15 including Bluetooth and ZigBee), wireless metropolitan area networks (IEEE 802.16) or others known to those skilled in the art. More preferably, the heart of the digital section is the MicroChip™ PIC microcontroller or other comparable microcontroller including microcontrollers from competing companies including Atmel and Texas Instruments. One such alternative is the STM32F4 series ARM Cortex-M4 microcontroller from STMicroelectronics which includes a floating point math core, Digital Signal Processing (DSP) library, and integrates peripherals such as SDIO (SD cards), USB, high speed 12 bit Analog/Digital Converters (ADC), and a large amount of RAM memory (192 KB). The preferable MicroChip™ PIC 16LC771 microcontroller or other comparable microcontroller would contain sufficient data and program memory, as well as peripherals, which allow the entire digital section as well as the ADCs to be neatly bundled into a single carefully programmed processing integrated circuit, and more preferably an application specific integrated circuit. Still preferably, the onboard counter/timer sections are used to produce the data acquisition timer, and can further be used to measure the VCO frequency and to confirm synthesizer lock. Still preferably, an onboard synchronous serial port (SSP) is used to control the synthesizer, to generate a RF data stream, and to communicate with external test equipment. Also preferably, an onboard main oscillator generates not only the microcontroller clock, but also the reference clock for the synthesizer. Additional digital outputs are used to control specific functions. Still preferably, one ADC input is dedicated to measurement of the VCO tune voltage to allow for automation of the final testing, and a separate function multiplexed onto this same pin allows limited direct control of the VCO tune voltage during automated final testing.

The synthesizer can induce distortion in the transmitted digital data when the data does not contain exactly equal numbers of ones and zeroes over a prolonged interval. This distortion arises because the synthesizer sees the modulation as error to be servoed out, and fights the modulation as it attempts to steer the VCO back to the nominal frequency. Preferably, the reference oscillator has the ability to modulate the reference frequency with any low-frequency content of the final transmitted digital data, with one of the results being that the reference and the VCO move in concert during modulation and therefore do not distort the data, and the low-frequency content of the designed data packet format should result in only minimal distortion. Optionally, this capability can be removed to reduce the imprint of the printed circuit board holding the one or more electronic components.

Preferably, the circuitry for the one or more electronic components comprises nonvolatile, rewriteable memory. Alternatively, if the circuitry for the one or more electronic components doesn't comprise nonvolatile, rewriteable memory then an approach should be used to allow for reprogramming of the final parameters such as radio channelization and data acquisition and scaling. Alternatively, other memory formats may be used, including, but not limited to external flash memory or a removable SD card (removable flash storage) to store a configuration parameter file editable as a text file. The entire device can be connected via USB Mass Storage Device standards to a PC. Without nonvolatile, rewriteable memory, the program memory can be programmed only once. Therefore, one embodiment of the present invention involves selective programming of a specific area of the program memory without programming the entire memory in one operation. Preferably, this is accomplished by setting aside a specific area of program memory large enough to store several copies of the required parameters. Procedurally, this is accomplished by initially programming the circuitry for the one or more electronic components with default parameters appropriate for the testing and calibration of the biometric monitoring system. When the final parameters have been determined, the next area is programmed with these parameters. If the final testing and calibration reveals problems, or some other need arises to change the values, additional variations of the parameters may be programmed.

Preferably the circuitry of the one or more electronic components includes an RF, optical and/or acoustic transmitter. Also, preferably, the circuitry includes a custom voltage controlled oscillator (VCO) made up of discrete electronic components, and a phase-locked loop (PLL) synthesizer built around commercially available electronic components. Additionally, preferably, the whole radio section of the circuitry can be powered down independently of the digital section components. Still further preferably, the synthesizer is controlled by the firmware via the SPI bus, and uses a crystal oscillator to derive a precision clock.

In these embodiments, the VCO design is unique in several ways. A buffer is preferably required between the core VCO active element and the antenna, to minimize pulling of the VCO frequency by physical movement at or near the antenna. Still preferably, the VCO itself uses a negative-resistance oscillator configuration. Still preferably, this is a stacked configuration to allow sharing between the VCO and the buffer. Still preferably, this configuration allows for two or more different configurations of the buffer with negligible size impact on the imprint of the circuitry of the one or more electronic components. This type of design can be laid out to allow for two different configurations of the buffer with a negligible impact on size. In one configuration, the VCO and buffer are in a cascade configuration (common base amplifier), such that the buffer provides voltage gain and buffering. In another configuration, the configuration becomes a common-emitter buffer, with the potential to allow firmware control of the transmitted power during PLL lock by reducing the gain of the buffer during lock. Preferably, this capability is provided with no size or power impact in the common-emitter configuration and reduces the potential for interference with other units during unit startup. On the other hand, the cascade configuration preferably is more resistant to antenna pulling, so precharge of the tune voltage and careful sequencing and timing of the startup are required to prevent interference.

Preferably, tuning of the VCO is performed by using a unique architecture that minimizes power consumption while significantly reducing noise compared to more conventional approaches such as using a varactor to perform tuning in response to an applied voltage. Preferably, in various embodiments of the present invention, the PLL applies a tuning voltage to the top side of a varactor, reversing biasing of the varactor to the level required to achieve a desired oscillation frequency. Conventional designs mix the modulation with this tune voltage to modulate the carrier produced by the VCO. However, this mixing normally requires a summing junction plus a buffer, and the buffer generates significant 1/F noise, seriously degrading the phase noise performance of the VCO. In addition, the required swing of the modulation voltage is orders of magnitude smaller than that of the tune voltage. Preferably in various embodiments of the present invention, only the PLL tune voltage is injected at the top of the varactor, and the modulation voltage is injected at the bottom of the varactor. By pre-inverting the modulation voltage, a bias voltage is achieved across the varactor that is the arithmetic sum of the tune voltage and the modulation voltage without the undesirable interactions of the conventional approaches. Because the required swing of the modulation voltage is very small, a resistive divider can be used as the last step in applying the modulation voltage, thus keeping the signal amplitude very large right up until the final division, forcing any accompanying noise to also be divided down before application to the varactor. This enhances the signal-to-noise ratio in the modulation voltage. Additionally because the required swing is very small, the division ratio in the final divider is large, allowing for very low current draw while still providing extremely low Thevenin equivalent resistance and very low thermal noise at this sensitive node.

Another feature of the circuitry of the one or more electronic components preferably is an antenna. The antenna, when RF, preferably, is designed onto the upper surface of the base of the biometric monitoring system and is integrated into the rest of the circuitry. The antenna can be configured in a number of ways, for example as a single loop, dipole, dipole with termination impedance, logarithmic-periodic, dielectric, strip conduction or reflector antenna. The antenna is designed to include but not be limited to the best combination of usable range, production efficiency and end-system usability. Preferably, the antenna consists of one or more conductive wires or strips, which are arranged in a pattern to maximize surface area. The large surface area will allow for lower transmission outputs for the data transmission. The large surface area will also be helpful in receiving high frequency energy from an external power source for storage. Optionally, the radio transmissions of the present invention may use frequency-selective antennas for separating the transmission and receiving bands, if an RF transmitter and receiver are used on the biometric monitoring system, and polarization-sensitive antennas are used in connection with directional transmission. Polarization-sensitive antennas consist of, for example, thin metal strips arranged in parallel on an insulating carrier material. Such a structure is insensitive to or permeable to electromagnetic waves with vertical polarization; waves with parallel polarization are reflected or absorbed depending on the design. It is possible to obtain in this way, for example good cross polarization decoupling in connection with linear polarization. It is further possible to integrate the antenna into the frame of a processing integrated circuit or into one or more of the other electronic components, whereby the antenna is preferably realized by means of thin film technology. The antenna can serve to just transfer biometric monitoring system data or for both transferring data to and for receiving control data received from a remote communication station which can include but is not limited to a wireless relay, a computer or a processor system. Optionally, the antenna can also serve to receive high-frequency energy (for energy supply or supplement). In any scenario, only one antenna is required for transmitting data, receiving data and optionally receiving energy. Optionally, directional couples can be arranged on the transmitter outputs of the biometric monitoring system and/or the remote communication station.

In many embodiments, particularly where the electronic components described above are enclosed in a single housing or enclosure creating a data acquisition unit, sensors may be included in the circuitry of the unit, particularly at least one accelerometer. Accelerometers and other sensors included in the electronics unit provide several benefits to the present invention. First, the sensor measurements can be used to provide co-registration between the man-mounted (subject-worn) data measurement system and any systems that may be vehicle-based or remotely-based. For example, accelerometer measurements may indicate a particularly high level of g-forces, and the two separate accelerometer measurements—at least one in the subject's data acquisition electronics enclosure and at least one for the aircraft—can be used to register the separate data streams so that they are in-line and synchronized. This synchronization of data streams can further be aided by inclusion of a real-time clock in the data acquisition circuitry enclosure which can provide a secondary data point to be matched and synchronized with the data files of other systems such as on the vehicle or remote systems. Such synchronization allows for accuracy of measurement both in real-time to help detect, prevent and mitigate dangerous conditions, and post-hoc analysis of the subject's condition in order to learn and understand what factors might lead to such dangerous conditions. For example, an accelerometer in the electronic component/data acquisition enclosure further can provide a measure of exertional hypoxemia where the system detects high g-force conditions and can use that information to help predict or determine if the subject soon thereafter experiences exertional hypoxemia based on the increased likelihood of such onset because as a subject experiences such forces and conditions, his or her tolerance to them decreases until given time to completely recover. Therefore, the sensor in the data acquisition electronics can help provide the system with data, especially when registered and synchronized with other sensors, to help predict, detect, mitigate or prevent dangerous breathing or other health conditions.

An additional feature of the present invention is an optional identification unit. By allocating identification codes—a subject code (for each subject being monitored), the remote communication station is capable of receiving and transmitting data to several subjects, and for evaluating the data if the remote communication station is capable of doing so. This is realized in a way such that the identification unit has control logic, as well as a memory for storing the identification codes. The identification unit of the biometric monitoring system is preferably programmed by radio transmission of the control characters and of the respective identification code from the programming unit of the remote communication station to the biometric monitoring system. More preferably, biometric monitoring system comprises switches as programming lockouts, particularly for preventing unintentional reprogramming of the biometric monitoring system.

In any RF link, errors are an unfortunate and unavoidable problem. Analog systems can often tolerate a certain level of error. Digital systems, however, while being inherently much more resistant to errors, also suffer a much greater impact when errors occur. Thus the present invention, when used as a digital system, preferably includes error control subarchitecture. Preferably, the RF link of the present invention is digital. RF links can be one-way or two-way. One-way links are used to just transmit data. Two-way links are used for both sending and receiving data.

If the RF link is one-way error control, then this is preferably accomplished at two distinct levels, above and beyond the effort to establish a reliable radio link to minimize errors from the beginning. At the first level, there is the redundancy in the transmitted data. This redundancy is performed by adding extra data that can be used at the remote communication station or at some station to detect and correct any errors that occurred during transit across the airwaves or transmitted through water. This mechanism known as Forward Error Correction (FEC) because the errors are corrected actively as the signal continues forward through the chain, rather than by going back to the transmitter and asking for retransmission. FEC systems include but are not limited to Hamming Code, Reed-Solomon and Golay codes. Preferably, a Hamming Code scheme is used. While the Hamming Code scheme is sometimes maligned as being outdated and underpowered, the implementation in certain embodiments of the present invention provides considerable robustness and extremely low computation and power burden for the error correction mechanism. FEC alone is sufficient to ensure that the vast majority of the data is transferred correctly across the radio link. Certain parts of the packet must be received correctly for the receiver to even begin accepting the packet, and the error correction mechanism in the remote communication station reports various signal quality parameters including the number of bit errors which are being corrected, so suspicious data packets can be readily identified and removed from the data stream.

Preferably, at a second, optional level, an additional line of defense is provided by residual error detection through the use of a cyclic redundancy check (CRC). The algorithm for this error detection is similar to that used for many years in disk drives, tape drives, and even deep-space communications, and is implemented by highly optimized firmware within the biometric monitoring system processing circuitry. During transmission, the CRC is first applied to a data packet, and then the FEC data is added covering the data packet and CRC as well. During reception, the FEC data is first used to apply corrections to the data and/or CRC as needed, and the CRC is checked against the message. If no errors occurred, or the FEC mechanism was able to properly correct such errors as did occur, the CRC will check correctly against the message and the data will be accepted. If the data contains residual errors (which can only occur if the FEC mechanism was overwhelmed by the number of errors), the CRC will not match the packet and the data will be rejected. Because the radio link in this implementation is strictly one-way, rejected data is simply lost and there is no possibility of retransmission.

More preferably, the RF link utilizes a two-way (bi-directional) data transmission. By using a two-way data transmission the data safety is significantly increased. By transmitting redundant information in the data from the sensors and electronics, the remote communication station is capable of recognizing errors and request a renewed transmission of the data. In the presence of excessive transmission problems such as, for example, transmission over excessively great distances or due to obstacles or media that absorbs the signals, the remote communication station is capable of controlling the data transmission, or to manipulate on its own the data emitted by the biometric monitoring system. With control of data transmission, it is also possible to control or re-set the parameters of the biometric monitoring system, e.g., changing the transmission channel. This would be applicable for example if the signal transmitted by the biometric monitoring system is superimposed by other sources of interference then by changing the channel the remote communication station could secure a flawless and interference free transmission. Another example would be if the signal transmitted by the biometric monitoring system is too weak, the remote communication station can transmit a command to the biometric monitoring system increasing its transmitting power. Still another example would be the remote communication station causing the biometric monitoring system to change the data format for the transmission, e.g., in order to increase the redundant information in the data flow. Increased redundancy allows transmission errors to be detected and corrected more easily. In this way, safe data transmissions are possible even with the poorest transmission qualities. This technique opens in a simple way the possibility of reducing the transmission power requirements of the biometric monitoring system. This also reduces the energy requirements of the biometric monitoring system, thereby providing longer battery life. Another advantage of a two-way, bi-directional digital data transmission is the possibility of transmitting test codes in order to filter out external interferences such as, for example, refraction or scatter from the transmission current. In this way, it is possible to reconstruct falsely transmitted data. Due to the safe and effective one-way and two-way transmission of the various embodiments of the present invention between the biometric monitoring system and the remote communication station, the present invention is particularly suitable for use other locations, such as in a nursing home, for example in monitoring many patients with respiratory problems.

The remote communication station of various embodiments of the present invention can be any device known to receive RF, optical or acoustical transmissions used by those skilled in the art to receive transmissions of sensor data from the monitoring system. The remote communication station by way of example but not limitation can include a communications device for relaying the transmission, a communications device for re-processing the transmission, a communications device for re-processing the transmission then relaying it to another remote communication station, a computer with wireless capabilities, a PDA with wireless capabilities, an IPad, a processor, a processor with display capabilities, and combinations of these devices. Optionally, the remote communication station can further transmit data both to another device and/or back to the monitoring system. Further optionally, two different remote communication stations can be used, one for receiving transmitted physiological data from the biometric monitoring system and another for sending data to the biometric monitoring system. For example, with the wireless physiological monitoring system of the present invention, the remote communication system of the present invention can be a wireless router, which establishes a broadband internet connection with the monitoring system and transmits the physiological signal to a remote internet site for analysis, preferably by the subject's physician. Another example is where the remote communication system is a PDA, computer or cell phone, which receives the physiological data transmission from the biometric monitoring system, optionally re-processes the information, and re-transmits the information via cell towers, land phone lines, transmitters or cable to a remote site for analysis. Another example is where the remote communication system is a computer or processor, which receives the physiological data transmission from the biometric monitoring system and displays the data or records it on some recording medium, which can be displayed or transferred for analysis at a later time.

Preferably, the remote communication station can pick up and transmit signals from distances of greater than about 5 feet from the subject, more preferably greater than about 10 feet from the subject, even more preferably greater than about 20 feet from the subject, still even more preferably greater than about 50 feet from the subject, still even more preferably greater than about 200 feet from the subject, and most preferably greater than about 500 feet from the subject. The remote communication station is used to re-transmit the signal based in part from the physiological signal from the biometric monitoring system wirelessly or via the internet to another monitor, computer or processor system. This allows for a third party to review the subjects biometric data and environmental conditions and if necessary to make a determination, which could include dispatching help.

Moving now to a description of the figures, FIG. 1 is an illustration of one embodiment of a breathing mask sensor system for pilots and aircrew. This particular embodiment comprises a breathing mask 10, breathing tube 40, inhaled gas sensor housing 15, an inhaled gas sensor 45, flow sensor housing 30, an exhaled gas sensor housing 20, and an exhaled gas sensor 25. Additionally, in this particular embodiment, the flow rate sensor housing 30 has an embedded temperature sensor housing 35 for a gas flow temperature sensor (not shown) which may be inserted into the flow sensor housing 30.

The breathing mask 10 in this embodiment is envisioned to be any flight mask commonly used in the art today, whether it be military, combat, commercial, freight, recreational, personal flight, or otherwise. The present invention is intended to operate as a sensor suite and processor system which may be adapted easily and readily to fit onto virtually any existing or later developed breathing mask. Alternatively, the system is also envisioned as providing a stand-alone breathing mask containing the sensor suite and processor, which can be integrated into any existing system. Although FIG. 1 depicts a flight mask embodiment, the sensors (exhaled gas sensor 25, inhaled gas sensor 45, temperature and flow sensors not shown) and processor (not shown) are designed to be adaptable with other breathing mask systems as well, such as for divers, firefighters and other first responders, medical breathing masks (e.g., anesthesia, CPAP), and the like. The breathing mask 10 is constructed of flexible, non-irritant materials commonly known to those of skill in the art for producing such masks.

The breathing tube 40 is similarly intended to be of any type presently known to those skilled in the art or later developed for use with such breathing mask systems. The breathing tube 40 is constructed of resilient yet flexible materials capable of bending, flexing and stretching while remaining able to return to its original shape, and without breaking, cracking, or otherwise becoming damaged. Typical hoses known in the art today are made of materials such as rubber, silicone, soft plastics, or the like. The breathing tube may be modified to contain any wires within its structure or inside the tube itself to prevent such wires from getting tangled. The breathing tube extends from the on board oxygen generation system (OBOGS) or other similar breathing mix generator (not shown) to the breathing mask 10, and provides a pathway for the breathing mix to reach the pilot or other aircrew wearing the mask.

Many embodiments employ not only a primary OBOGS, but also a backup oxygen supply or delivery system (BASS) (not shown). Preferably, the backup oxygen supply or delivery system operates in an automated or semi-automated manner. With respect to the BASS, automated means that if the primary OBOGS fails, or the system detects a dangerous breathing condition that the OBOGS cannot mitigate or counteract, the BASS would automatically initiate its function to supply additional or supplemental oxygen or breathing mix of gases to the subject. Semi-automated operation of the BASS means that when the primary OBOGS fails or the system detects a dangerous breathing condition that cannot be mitigated or counteracted, a warning or alert is sent or communicated to the subject or a third party who initiates operation of the BASS to deliver additional or supplemental oxygen or breathing mix of gases to the subject.

The present embodiment depicts a flow sensor housing 30 at the distal end of the breathing tube 10. The flow sensor housing 30 is designed to connect or be adaptable to all breathing tubes presently known to those skilled in the art or later developed for use with such breathing mask systems. The flow sensor housing 30 contains a central chamber (not shown), extending through the length of the flow chamber housing, through which the breathing mix flows from the breathing mix generator (not shown), through the breathing tube 40, to the breathing mask 10, for the subject to breathe. The central chamber of the flow sensor housing 30 is adaptable to include one or more sensors. Preferably, in embodiments where the flow sensor chamber is included, at least one flow sensor is contained within the central chamber of the flow sensor housing 30. Flow sensors may be used to measure the rate at which gas is flowing, volume of gas, and the like.

Additionally, several embodiments include a temperature sensor (not shown) within the flow sensor housing 30. The temperature sensor is typically a thermistor, mounted in the temperature sensor housing 35. The thermistor temperature sensor is mounted into the temperature sensor housing 35 with the resistive, measurement end of the thermistor extending through ports in the side of the flow sensor housing 30 and into the central chamber of the flow sensor housing. In these embodiments, there is preferably at least one flow separator disc (not shown) positioned perpendicular to the flow of the breathing mix of gases (and thus perpendicular to the central chamber of the flow sensor housing). More preferably there are at least two flow separator discs with a predetermined amount of space between them. The measurement end of the thermistor, when placed into the central chamber of the flow sensor housing 30 is either on the proximal side of the preferably one flow separator disc, or in between the preferably two flow separator discs. The flow separator disc(s) operate to cause disturbances in the flow of the breathing mix gases traveling toward the subject, and to cause the mix to separate into various streams of gas. This separation allows the thermistor to register and measure a more accurate temperature reading of the gas mixture as a whole, and prevents false readings based on a condensed or unmixed burst of a particular gas.

Once the breathing mix passes through the flow sensor, and into and through the breathing tube 40, it travels toward the mask 10 where it will be breathed in by the subject. To get to the subject, in some embodiments, the breathing mix of gas mast pass through an inhaled gas sensor 45 which is contained in an inhaled gas sensor housing 15. Much like the flow sensor housing 30, the inhaled gas sensor housing 15 is designed to be resilient and adaptable to fit virtually all presently known breathing tube and breathing mask systems, as well as those later developed. The inhaled gas sensor housing 15, attaches at one end to the breathing tube 40, and to the breathing mask 10 at the other end. Thus, as the breathing mix exits the breathing tube 40, it passes through the inhaled gas sensor housing 15 and then into the breathing mask 10. Again, much like the flow sensor housing 30, the inhaled gas sensor housing may contain any type or combination of sensors. The most common types of sensors which may be used here are oxygen sensors, carbon dioxide sensors, and temperature sensors. However, many other types of sensors are contemplated for use in the inhaled gas sensor housing, including, but not limited to, sensors for measuring volatile organic compounds, hydrocarbons, pressure, flow rates, and the like. The sensors may be miniaturized to fit into a single inhaled gas sensor housing 15, or multiple such housings may be attached in series, whereby the gas flows through each of them in turn en route to the breathing mask 10. Each sensor that is used records its particular signal as the breathing mix flows through or over the sensor and into the breathing mask 10.

Once the breathing mix enters the breathing mask 10, it is inhaled by the subject. At least one check valve (not shown) is placed in the air flow pathway which prevents additional gas from entering the mask until after the subject has exhaled his or her breath. Alternatively, at least two check valves are placed in or on the inhaled breath mechanism, possibly attached to the inhaled gas sensor housing 15, and in or on the exhaled breath mechanism, possibly attached to the exhaled gas sensor housing 20, and operate to cause the exhaled air to leave the breathing mask only through the exhaled breath housing and sensor. The check valve prevents the inhaled and exhaled gases from mixing, and thus providing skewed measurements from the exhaled gas sensor 25.

Internal to the breathing mask, many other sensors are contemplated for use. For example, a microphone(s) may be included which, in combination with the check valve, are used to provide a noise canceling function when the subject is talking or communicating. At least one electrode, preferably a dry surface electrode, may be included, either in the mask or otherwise on the subjects body. Dry surface electrodes may be used to detect and measure electroencephalography (EEG), electrocardiography (ECG), electromyography (EMG), electrooculography (EOG), heart rate, or other physiological signals which may be used to help determine the subject's physiological state.

Once the subject exhales, the expired breath passes through at least one exhaled gas sensor 25, which is seated in an exhaled gas sensor housing 20. Similar to the inhaled gas sensor housing 15, the exhaled gas sensor housing 20 is designed to be resilient and adaptable to fit virtually all presently known breathing tube and breathing mask systems, as well as those later developed. The exhaled gas sensor housing 20 may contain any type or combination of sensors. The most common types of sensors which may be used here are oxygen sensors, carbon dioxide sensors, and temperature sensors. In this particular embodiment, the exhaled gas sensor is a carbon dioxide sensor. The carbon dioxide sensor is placed into a specially adapted and innovative carbon dioxide sensor housing 20, to be adapted to the exhaled breath side of any such breathing mask presently known to those skilled in the art, or later developed. Other embodiments may include other types of sensors for use in the exhaled gas sensor housing 20, including, but not limited to, sensors for measuring volatile organic compounds, hydrocarbons, pressure, flow rates, and the like. The sensors may be miniaturized to fit into a single exhaled gas sensor housing 20, or multiple such housing may be attached in series, whereby the gas flows through each of as it is exhaled and exits the breathing mask 10. Each sensor that is used records its particular signal as the breathing mix flows through or over the sensor and into the ambient air.

The sensor or sensors used in the above system, measure their particular object as the gas flows through or over the sensor. These measurements are recorded substantially in real-time per each breath. By real time, it is intended that the sensor preferably records the measurement and transmits the signal to the processor (not shown) within 10 seconds of the gas passing through or over the sensor. More preferably, the sensor records the measurement and transmits the signal to the processor within 5 seconds of the gas passing through or over the sensor. Even more preferably, the sensor records the measurement and transmits the signal to the processor within 3 seconds of the gas passing through or over the sensor. Still more preferably, the sensor records the measurement and transmits the signal to the processor within 1 seconds of the gas passing through or over the sensor. Yet more preferably, the sensor records the measurement and transmits the signal to the processor within 500 milliseconds of the gas passing through or over the sensor. Even yet more preferably, the sensor records the measurement and transmits the signal to the processor within 100 milliseconds of the gas passing through or over the sensor. Even still more preferably, the sensor records the measurement and transmits the signal to the processor within 50 milliseconds of the gas passing through or over the sensor. Most preferably, the sensor records the measurement and transmits the signal to the processor simultaneously as the gas passes through or over the sensor.

The processor (not shown) collects and correlates the signals received from the sensors. The processor contains and employs an algorithm (not shown) which uses the signals received from the sensors to calculate various measurements and metrics based on the signals from the sensors (see FIG. 7). Those measurements and metrics are then parsed to identify a dangerous physiological condition that is presently occurring, or more preferably to predict the onset of such a condition. When the processor and algorithm calculate that such a dangerous condition is occurring, or soon will occur, a warning or alert is sent out. The warning or alert may be sent to the subject or wearer of the mask, to a third person, such as a remote monitoring system (e.g., aircraft carrier flight deck monitor, dive master, another pilot or team member), or to an internal or external system, such as a closed-loop control system for regulating the breathing mix delivered to the subject. The warning or alert serves to put the receiver of the alert on notice that the subject is experiencing, or is about to experience a dangerous breathing condition, and allows that person to either come to the subjects aid, or to help prevent the onset of more serious conditions.

Some embodiments comprise a closed-loop breathing mix delivery system (not shown). Such embodiments take the measured and calculated values based at least in part on the signals received from the sensor or sensors contained in the particular embodiment, and determine the appropriate mix of gases for the subject that would either help said subject recover from a presently occurring dangerous breathing condition, or prevent an oncoming predicted dangerous breathing condition. Such embodiments would take the measured and calculated values and automatically adjust the breathing mix to the optimum volumes of each mixed gas and provide this new mix through the system described above to the subject. The sensor measurements would each occur again, and the closed-loop system would continue to adjust the breathing mix accordingly to those continuously measured and calculated values.

Still other embodiments may employ an oxygen or breathing mix dosing system (not shown). The dosing system is primarily used for systems comprising a reserve or backup oxygen or breathing mix gas supply. In the event of the primary or main oxygen or breathing mix supply system failing (e.g., failure of the OBOGS in a fighter jet), a reserve or backup system would then begin to supply the required gases for the subject to maintain a healthy breathing condition or status. Such a system may be automated (e.g., ABOS—automated backup oxygen system) and kick in automatically upon failure of the primary delivery system or loss of ambient or cabin pressure, or may be semi-automated where the subject or a third party triggers the system to operate based on perceived or measured need of additional oxygen or breathing mix. Most often, such reserve or backup systems comprise a reserve gas tank with a finite amount of gas, though they may comprise a backup OBOGS or other generation system. The oxygen or breathing mix dosing system helps to extend the life of the reserve gas supply and thus maximize the likelihood that the subject has enough oxygen or breathing mix to return to safety, and mitigates or prevents the onset of dangerous breathing or other health conditions. Preferably, the system uses the sensors and components described herein to measure and monitor the subject's metabolic rate. The metabolic rate is then used to determine the required dose of oxygen or breathing mix necessary to sustain the subject's healthy breathing status. This system automatically increases or decreases the amount of the reserve or backup gas supply that is delivered to the subject based at least in part on the sensor measurements and the measured or calculated metabolic rate. AS the subject's metabolic rate increases and demand for oxygen or breathing mix increases, the system increases the amount of the reserve gas supplied, and vice versa. Thus, by providing only the amount of oxygen or breathing mix necessary to maintain safe status of the subject, the amount of the reserve gas supply utilized is minimized, and the life of the reserve is extended. This system allows for extended missions when necessary, as well as maximizes the likelihood that the subject will be able to return to safety upon failure of the primary gas supply system.

Figure 2:
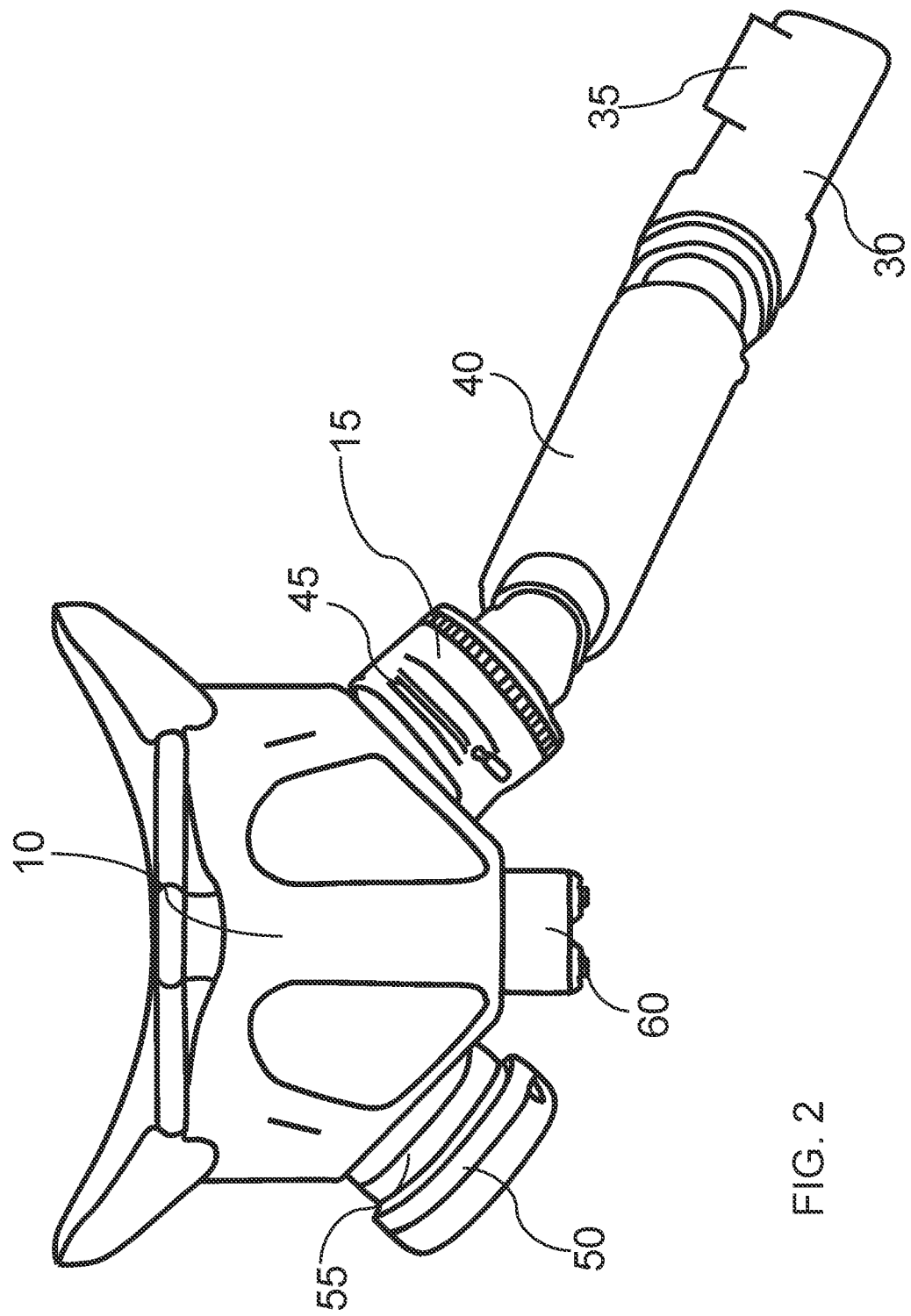
FIG. 2. Overhead perspective view of an alternative embodiment of the present invention of a pilot or aircrew flight mask with multiple, alternative sensors used for identification or prediction of dangerous breathing or other health conditions.

FIG. 2 depicts an alternative embodiment whereby the exhaled gas sensor housing with dust cover 50 and the exhaled gas sensor 55 are particularly adapted for oxygen sensors, as opposed to carbon dioxide sensors as in FIG. 1. Again, the same process and alternative configurations may be applied to the embodiment in FIG. 2 allowing for the system to measure only exhaled partial pressure of oxygen, inhaled partial pressure of oxygen, or any combination of other gases and measurements based on the sensors chosen.

One additional feature depicted here is a microphone 60. This figure depicts the external portion of the microphone 60, which has the actual audio sensor (not shown) on the interior of the breathing mask 10. One or more microphones may be incorporated into the breathing mask 10. The primary microphone allows the subject to communicate with other team members or remote monitoring stations and personnel. However, at least one additional microphone may be included for noise cancellation purposes. Traditionally, when the subject of such a breathing mask system speaks, the inspired and expired air inherent to speaking causes disruptions, or noise, in the inhaled and exhaled gas sensor measurements. Providing at least one additional microphone allows the system to calibrate the measurements along with the check valve (not shown) to differentiate between true inhaled or exhaled breaths, and inspired or expired air resulting from speech. This allows the system to perform a noise canceling function and minimize speech related artifacts from the sensor measurements.

Figure 3:
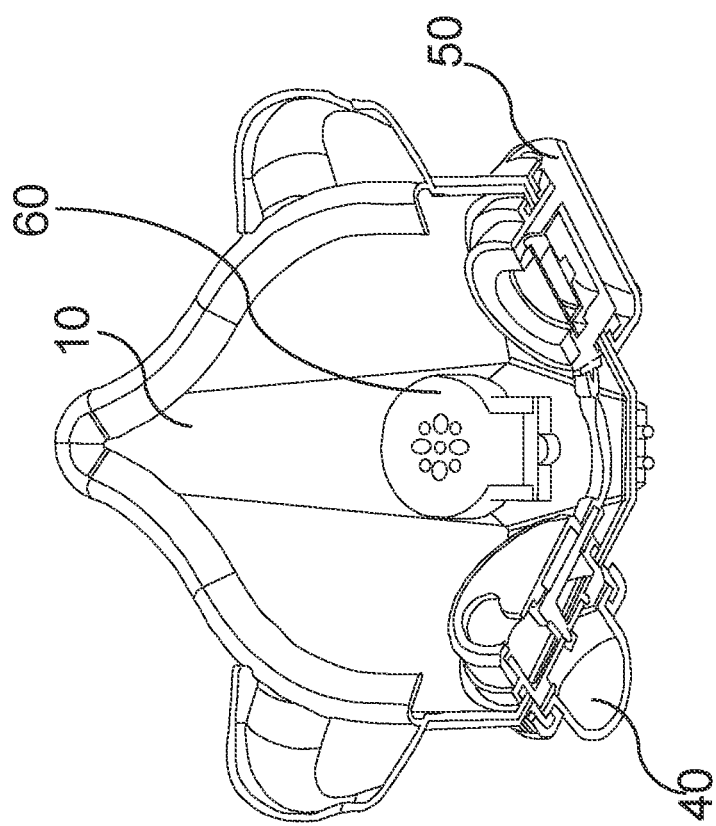
FIG. 3. Reverse view, cross-sectional depiction of a pilot or aircrew flight mask containing multiple sensors used for identification or prediction of dangerous breathing or other health conditions.

FIG. 3 depicts an alternative view of the mask embodiment in FIG. 2 from the reverse side of the breathing mask 10. Here, the subject places his or her mouth and nose into the breathing mask 10, situating the mask into its natural position. The interior of the mask may contain a microphone, thermistor, and/or pressure transducer 60 is situated immediately near the subject's mouth. If a microphone is included, it may be used for communication purposes, and/or for providing a noise canceling function to prevent noise in the sensor recordings resulting when the subject speaks. Additional microphones may be provided inside the breathing mask 10 to allow one for communication, and at least one for noise canceling functions. If a thermistor is included, it may be used to measure in-mask temperature, inhaled breath temperature, exhaled breath temperature, or the like. Similarly, if a pressure transducer is included, it may be used to measure in-mask pressure.

The breathing tube 40 connects into the inhaled gas sensor housing (not shown). Here, the breathing mix of gases crosses over the inhaled gas sensor (not shown) which is situated inside or attached to the inhaled gas sensor housing (not shown). The sensor, again, may be any one of a variety of sensors, including but not limited to oxygen sensors, temperature sensors, carbon dioxide sensors, volatile organic compound sensors, hydrocarbon sensors, pressure sensors, flow sensors, accelerometers, gyroscopes, microphones, electrodes, and the like, or any combination thereof. Also, the sensors may be sufficiently miniaturized to fit into a single housing, or may be attached in series allowing the gas to flow over or through each sensor in turn as it passes from the breathing tube 40 into the breathing mask 10.

As the breathing mix of gases passes over the inhaled gas sensor(s) (not shown), it enters the mask 10 where it is inhaled by the subject. A check valve (not shown) stops the flow of air and prevents the subject's exhaled breath from returning through the inhaled gas sensor (not shown) and into the breathing tube 40 against the pressurized flow. Instead, the subject's exhaled breath passes through the exhaled gas sensor (not shown) which is situated inside or attached to the exhaled gas sensor housing 50. As the exhaled breath passes through the exhaled gas sensor (not shown), the sensor records its measurements and transmits them to the processor for analysis.

Figure 4:
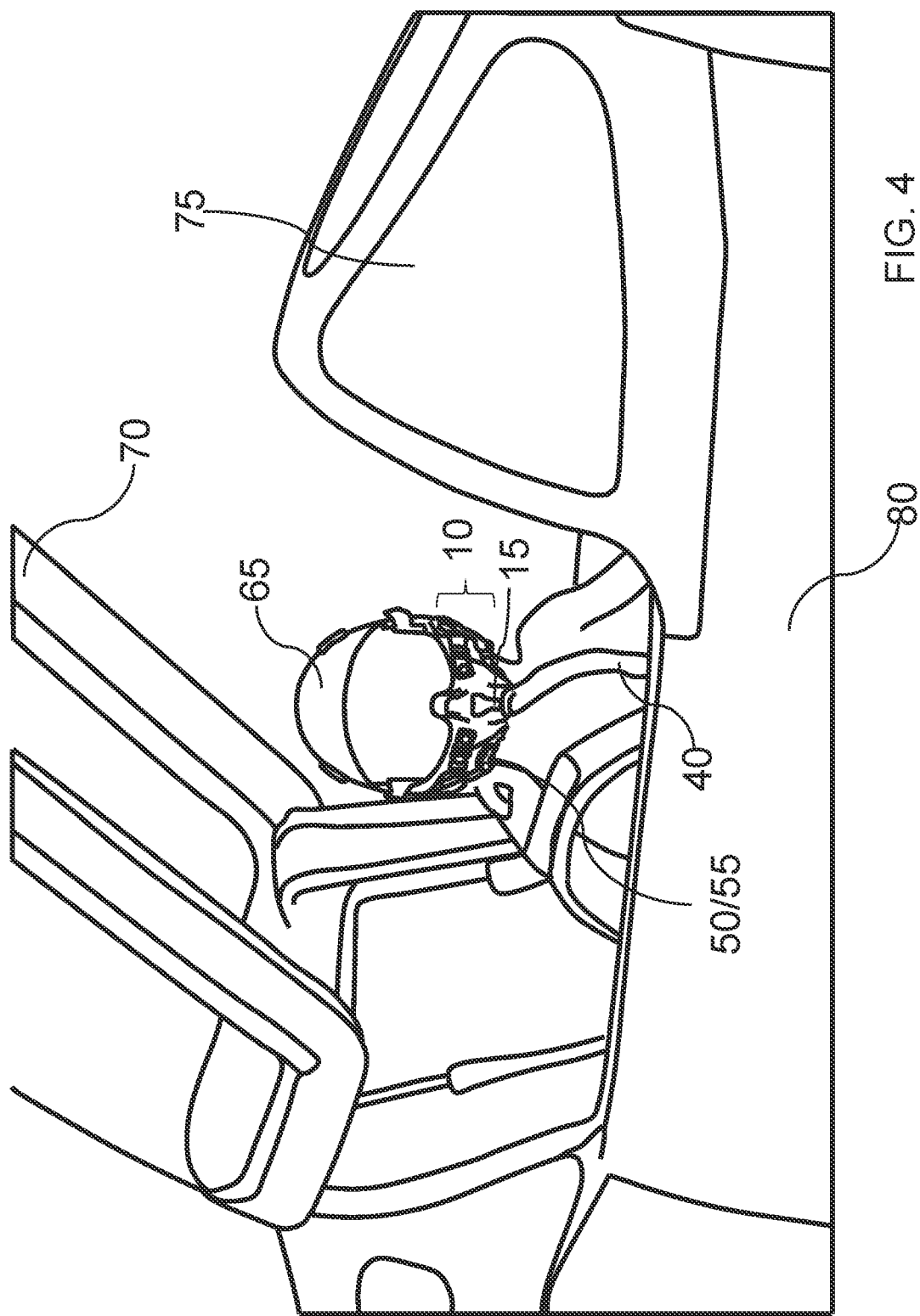
FIG. 4. Schematic depiction of a military pilot in the cockpit of a fighter plane, wearing a mask containing sensors used for identification or prediction of dangerous breathing or other health conditions.

FIG. 4 depicts a particular embodiment of the present invention for pilots and aircrew, and more particularly military and fighter pilots. The subject or pilot 65 dons the breathing mask 10 which typically is attached to a helmet. The subject 65 enters the aircraft 80 and situates him or herself into the cockpit. In this figure, a representative fighter jet is depicted, with the cockpit door 70 opened above the subject 65, and the cockpit windshield 75 in front. On board such an aircraft, an OBOGS or other breathing mix generator (not shown) is included which provides a pressurized gas flow of breathable gases for the subject to breathe when operating the aircraft. That breathing mix of gases travels through the breathing tube 40 and into the breathing mask 10 as previously described. In many embodiments, before the breathing mix enters the breathing mask 10 for the subject to breathe, it passes through an inhaled gas sensor (45, not depicted in the present figure) which is situated inside of or attached to an inhaled gas sensor housing 15. The inhaled gas sensor records its measurements and transmits those measurements via a signal to the processor (not shown). As the subject breathes in the breathing mix and then exhales his or her breath, a check valve or valves, as described above, direct the exhaled breath to exit through the exhaled gas sensor 55 which is situated inside of or attached to the exhaled gas sensor housing 50, and which is attached to the breathing mask 10. Again, both the inhaled and exhaled gas sensors may be of any type previously described, or any combination thereof, and may be sufficiently miniaturized to fit into a single housing, or may be attached in series or in separate housings.

Preferably, the sensor housings for both inhaled and exhaled gas sensors are designed to be easily adaptable to be fitted or retrofitted onto virtually all existing breathing masks known to those in the art, as well as those later developed. The sensor housings are intended to be able to attach to any such mask and thus provide any of the described sensors and their accompanying measurements to virtually any breathing mask system. One non-limiting example of an adaptable housing attachment mechanism is to provide a threaded ring which fits securely into the opening of a bear mask on either the inhaled or exhaled side, and to which the sensor housing also securely attaches. The sensor housing may then be secured into position with respect to the threaded ring by means of set screws. This allows for a different threaded ring to be used for the particular mask employed, while still using the same sensor housing. The set screws allow the sensor housing to be positioned in a particular orientation that is convenient to the subject and does not encumber his or her movements or comfort, while still ensuring the sensor housing's secure placement into the threaded ring and attachment to the breathing mask. Those skilled in the art will understand and appreciate other such adaptable attachment means which provide a secure attachment to multiple styles, forms, and types of masks.

Figure 5:
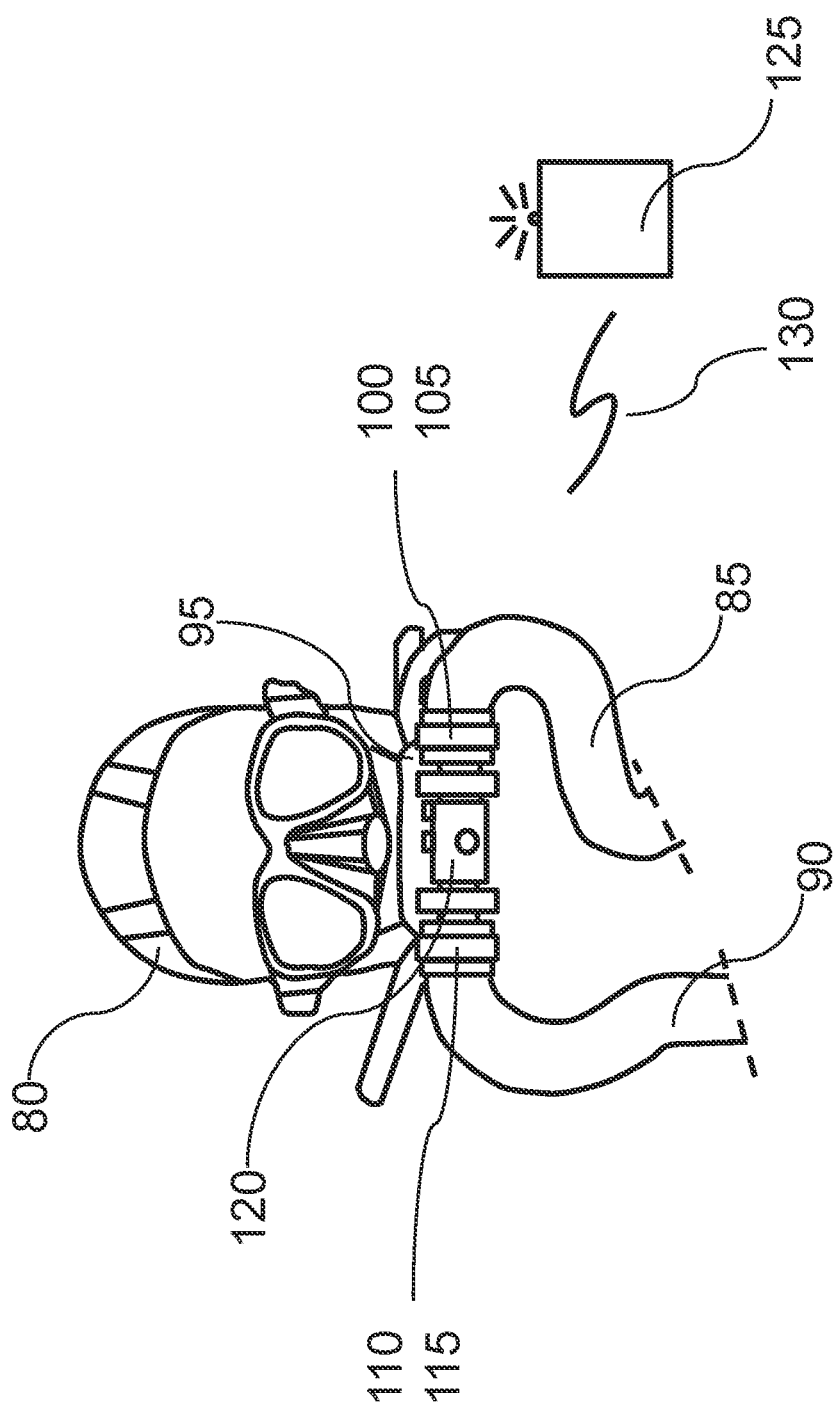
FIG. 5. Schematic depiction of one embodiment of the present invention of a recirculating diving mask with multiple sensors used for identification or prediction of dangerous breathing or other health conditions.

FIG. 5 depicts another embodiment of the present invention where the sensor suite is deployed in a diver's breathing system. This particular embodiment depicts a military combat diver, utilizing a completely enclosed, recirculated breathing system. However, the invention is contemplated for use with all types and styles of diver breathing systems, including military, commercial, and recreational divers.

In this embodiment, the diver 80 dons his or her diving suit (not shown) which includes a diving breathing mask 95. The diver's breathing system includes a tank (135, not shown in this figure) or several tanks, which provide the oxygen and other breathing gases (breathing mix) for the diver. Those gases are pressurized and travel from the tank(s) toward the diver's breathing mask 95 through a breathing delivery tube 85. This tube is similarly constructed to the breathing tube in the above described aircrew embodiments to be resilient and flexible, and to be able to withstand extreme pressures and conditions. In some embodiments, as the breathing mix passes through the delivery tube 85, it enters into the diver's breathing mask 95 by passing through an inhaled gas sensor housing 100 which is integrated into the breathing delivery tube attachment mechanism that connects the delivery tube 85 to the diver's breathing mask 95. In those embodiments, an inhaled gas sensor 105 is situated inside of attached to the inhaled gas sensor housing 100 similar to the aircrew embodiment above. As the breathing mix passes over the inhaled gas sensor 105, the sensor records its measurement and transmits to the processor 125.

The breathing mix then enters the diver's breathing mask 95 and the diver inhales said mix. At least one check valve 120 is used to prevent the exhaled breath from reentering the breathing delivery tube 85, and instead forces that exhaled breath to exit through the exhaled gas sensor housing 110, exhaled gas sensor 115 situated inside of or attached to the exhaled gas sensor housing 110, and into the breathing return tube 90. As the exhaled breath passes through or over the exhaled gas sensor 115, that sensor too records its measurement and transmits that measurement via a signal to the processor 125 for analysis. The exhaled breath then travels through the breathing return tube 90 and returns to the tank(s) (135, not shown in this figure) where it is remixed for recirculation.

The completely closed-loop recirculation system depicted in the present embodiment is typical of military combat diver systems where no exhaled breath is expelled in order to prevent the creation of gas bubbles in the water around the diver which may give away the diver's position. Such closed-loop recirculation systems may also be used commercially or recreationally as well. Alternatively, in a non-recirculating system, the exhaled breath, after it passes through the exhaled gas sensor 115 and housing 110, would not necessarily be returned through a breathing return tube 90, but could be expelled into the water.

Again, as in the previously described embodiments, the sensors record their measurements and transmit the measurements to the processor via a signal. The system may include sensors on the torso, face mask, and breathing tube, and electronics box and warning LED. Such sensors may include, but are not limited to oxygen sensors, temperature sensors, carbon dioxide sensors, volatile organic compound sensors, hydrocarbon sensors, pressure sensors, flow sensors, accelerometers, gyroscopes, microphones, electrodes, and the like. The sensors may communicate their signals to the processor via wired or wireless means 130. The processor 125 comprises an algorithm which receives the sensor signals, and uses the measured values to calculate a plethora of metrics related to the diver's biometric breathing conditions, health, environment, metabolic conditions, and the like. The algorithm then correlates the measured values and calculated values to determine whether the diver 80 is in a safe, healthy condition, undergoing a dangerous breathing condition (such as hypoxia), or to predict if the diver is likely to or about to experience such a dangerous breathing condition. If the diver 80 is experiencing, or is predicted to experience such a dangerous breathing condition, the processor 125 then transmits a warning signal or alert. This warning or alert may be transmitted to the diver 80, and may be in the form of a visual signal integrated into the diver's breathing mask 95 or equipment, an audio signal broadcast through the diver's communication system, or a mechanical signal such as a vibration. The warning or signal may also be transmitted to a third person, such as another diver or team member, a submerged vehicle in the vicinity (e.g., diver delivery vehicle or manned vessel), or to the surface such as to a dive master. In any of these events, the third person would be alerted that the diver 80 is in trouble and may be incapacitated, and thus can initiate a rescue procedure to recover the diver 80 before he or she becomes unable to recover and drowns. Alternatively, a closed-loop system may be provided whereby when a dangerous condition is identified or predicted, the system itself recalibrates the breathing mix of gases in order to try and counteract the condition or prevent it from occurring. The various types of warnings and alerts may also be used in conjunction with each other providing multiple levels of safety for the diver 80.

Figure 6:
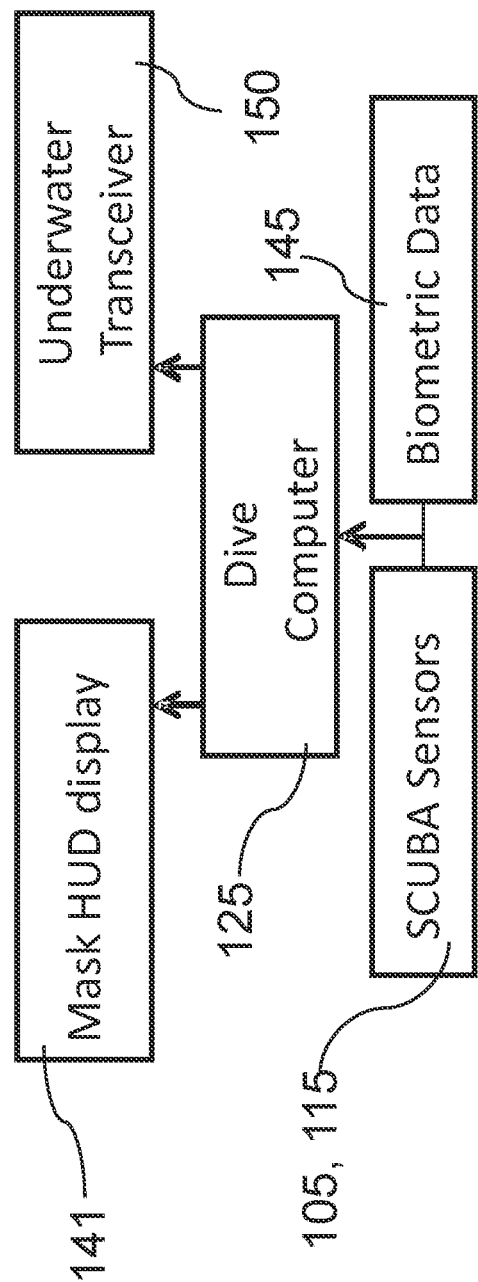
FIG. 6. Schematic representation of a diver wearing a mask with sensors used for identification or prediction of dangerous breathing or other health conditions, and a flow chart depicting the message, alert, or warning relay process.
Figure 6:
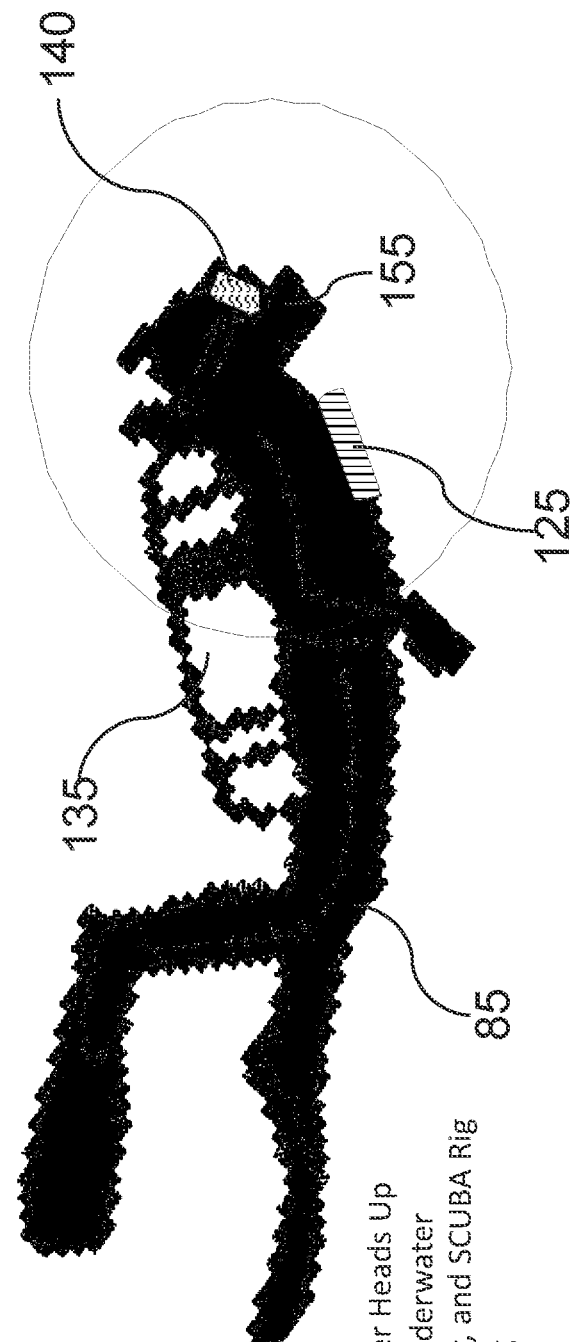

FIG. 6 depicts a diver 80 in action employing the system of the present invention. Here, the diver 80 can be seen as wearing an entire diving system comprising breathing gas tank(s) 135, diving mask 140, breathing mask 155, and the onboard processor 125. The breathing gas tanks mix and deliver breathing gases through the breathing delivery tube (85, not shown in this figure) to the diver's breathing mask 155 for the diver to breathe. The diver's breathing mask 155 comprises the exhaled gas sensor housing 110 and exhaled gas sensor 115, and in some embodiments the inhaled gas sensor housing 100 and inhaled gas sensor 105, all previously described. Further included in the present embodiment, the diver 80 is wearing a diver's mask with a heads up display 141. This mask with heads up display comprises visual indicators which may be used as part of the warning and alert system for identifying and predicting dangerous breathing or other health conditions such as hypoxia. The heads up display operates, by way of non-limiting example, as follows. The sensors record their measurements as the breathing mix or exhaled breath flows over or through the particular sensors employed in the embodiment. As above, these sensors may include, but are not limited to, oxygen sensors, temperature sensors, carbon dioxide sensors, volatile organic compound sensors, hydrocarbon sensors, pressure sensors, flow sensors, accelerometers, gyroscopes, microphones, electrodes, and the like. As the sensors record their measurements, they transmit a signal related to those measurements to the processor 125 by wired or wireless communication methods.

The processor 125, comprising an algorithm, receives the signals and records the measurements to which the signals relate, and uses those measurements to calculate still further biometric data 145 related to the diver's health, metabolic state, respiratory conditions, environment, and the like. When the measured values and the calculated metrics indicate that the diver 80 is experiencing a dangerous condition, or predicts such a condition, the processor 125 then communicates a signal to the diver's mask heads up display 141. The heads up display 141 then displays the warning to the diver 84 by any number of means, including, but not limited to flashing or blinking lights, preferably LEDs, an auditory signal or message, a scrolling textual alert, or the like. Additionally or alternatively, a warning signal or alert may be sent to an external underwater transceiver 150 which in turn relays the message to other divers or team members in the vicinity, to a manned or unmanned vehicle in the area which may try to extract the diver, or to a topside (out of water) vessel or person, such as a dive master who may help initiate preventative or rescue procedures to recover the afflicted diver.

Figure 7:
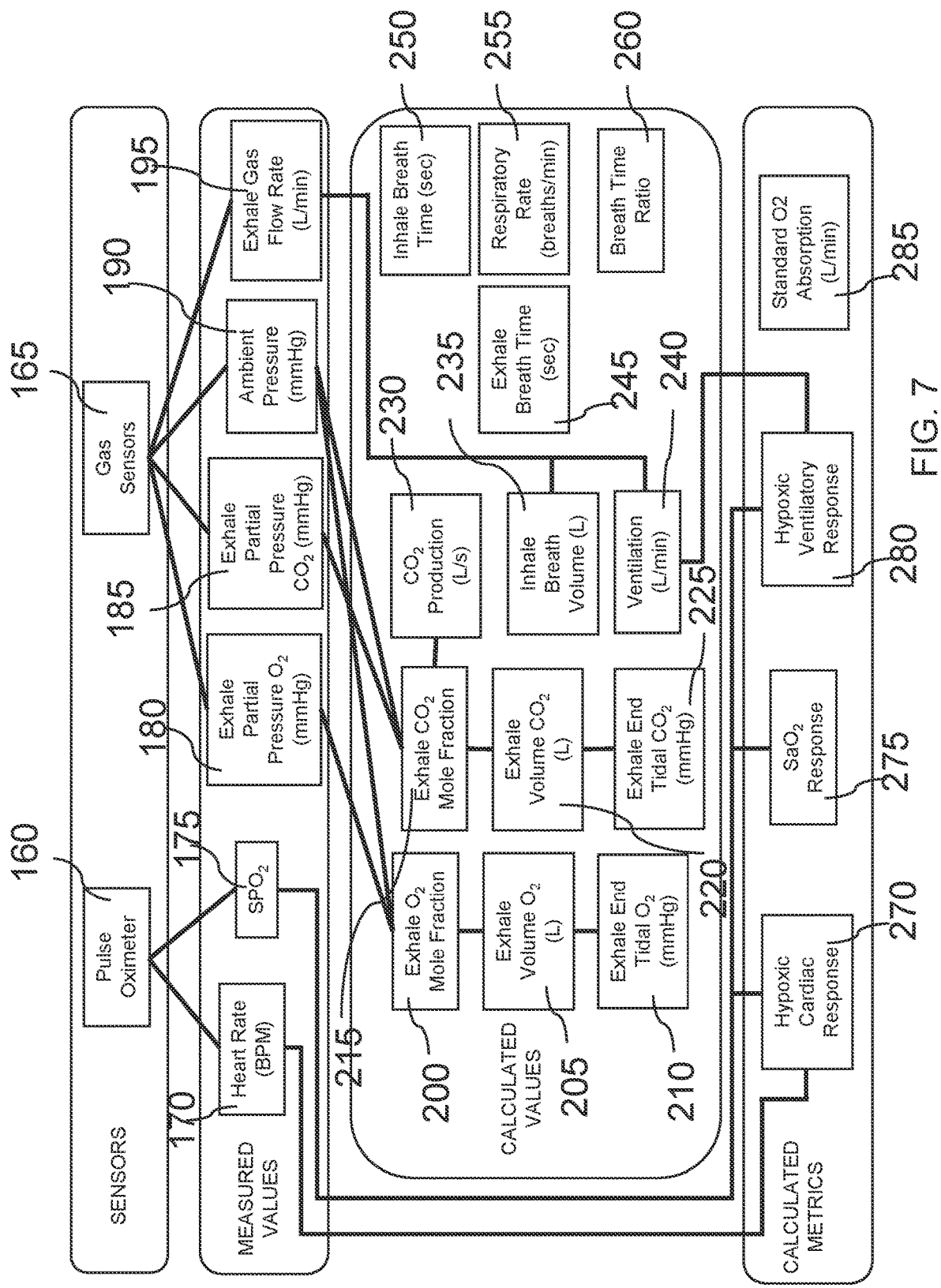
FIG. 7. Flow chart depicting the traditional sensors used and the metrics obtained from those sensors compared to the measured and calculated metrics obtained from the various embodiments of the present invention utilizing gas sensors.

FIG. 7 depicts a flow chart representing the inputs to the processor comprising an algorithm and the metrics that may be measured or calculated by the system and used for making a determination as to the subject's health status or danger, and in predicting the onset of dangerous conditions such as hypoxia.

Traditional systems for measuring and monitoring the status of a subject in the applications for which this invention is intended typically rely solely on pulse oximeters 160, which provide a non-invasive method for measurement of oxygenation, or oxygen saturation ($SpO_2$) 175 of a subject's blood. Pulse oximeters are generally optical sensors whereby two different wavelengths of light, typically red light and infrared light, are passed through a portion of the subject's body and received by a photodetector on the other side. Each of the different wavelengths of light has a different absorption rate for oxygenated or non-oxygenated blood. The subject's blood oxygen saturation is determined as a function of the absorbance of these wavelengths of light as indicating the ratio of oxygenated versus non-oxygenated hemoglobin. Pulse oximeters may be used to not only measure oxygen saturation, but also heart rate (in beats per minute, or BPM) 170.

These pulse oximeter measurements (oxygen saturation and heart rate) may then be used to calculate several other useful metrics as well. From a combination of saturation and heart rate, the subject's Hypoxic Cardiac Response 270 may be calculated. Hypoxic cardiac response 270 is essentially the effect that hypoxic conditions have on the subject's cardiac function. As oxygen saturation decreases, cardiac function tends to increase as well. The pulse oximeter's 160 oxygen saturation 175 measurement may also be used to calculate $SaO_2$ response 275 and Hypoxic Ventilatory Response 280. $SaO_2$ response 275 is a measure of the percentage of hemoglobin molecules in the blood that are oxygenated and is relevant to how that percentage changes under hypoxic conditions. Hypoxic ventilatory response (HVR) 280 is the effect whereby ventilation, or the rate at which gas enters and leaves the lungs, increases as a result of hypoxic conditions.

All of the above are common, standard measurements and calculations which are capable of being acquired through sole use of a pulse oximeter, and all of which are useful in detecting or measuring the subject's status. The present invention, however, goes beyond mere pulse oximeter measurements and calculations. The present invention may include a pulse oximeter as one of the sensors utilized in the system. Thus, the present invention may perform the standard measurements and calculations above. Additionally, the present invention employs at least one gas sensor 165, and in many embodiments several additional gas sensors 165 which allow the system to obtain more measurements, calculate many more biometrics, and overall provide a more robust and accurate system with predictive capabilities rather than just identification.

Once such gas sensor 165 is an exhaled breath oxygen sensor. Preferably, this exhaled breath oxygen sensor measures the partial pressure of oxygen 180 of an exhaled breath, typically measured in mmHg. In the figures described above, particularly FIG. 2 and FIG. 3, the exhaled gas oxygen sensor is depicted as reference 55. Some embodiments may utilize a pulse oximeter (not shown) which also measures oxygen saturation. The pulse oximeter may be a traditional such sensor clipped on to the subject's finger; however, such pulse oximeters may be troublesome as obstacles to the subject who is typically performing potentially dangerous activities (e.g., pilots, divers, first responders, etc.). Therefore, it is preferable that the system utilizes a pulse oximeter that is attached, affixed to, or applied in the subject's ear cup. Such systems allow the subject to use his or her hands in a free, unencumbered manner while still obtaining oxygen saturation measurements via pulse oximeter. Further, the pulse oximeter in such embodiments may be the sole or primary oxygen sensor used, but also may be a secondary or backup oxygen sensor.

Another gas sensor 165 which may be utilized with the present invention is an exhaled breath carbon dioxide sensor which is used to measure the partial pressure of carbon dioxide 185 in the subject's exhaled breath, typically measured in mmHg. The exhaled gas carbon dioxide sensor is depicted in FIG. 1 as reference 25

Additional sensors are also potentially included, such as to measure ambient pressure (in mmHg) 190 and exhaled gas flow rate (L/min) 195. Ambient pressure refers to the pressure immediately surrounding the subject. For example, with respect to most fixed wing aircraft (e.g., fighter jets), the ambient pressure would be cabin or cockpit pressure surrounding the pilot; for divers, ambient pressure would be the surrounding water Although these are the only measured values depicted in the figure, the invention is intended to use numerous other types of sensors, and combinations thereof, to measure many other values. For example, oxygen and carbon dioxide sensors may be included on the inhale end of the breathing mask in order to measure the respective partial pressures of those gases inhaled. Temperature sensors may be included on either the inhaled or exhaled breath side of the mask to determine temperature of the gases being breathed. Such temperature measures can be used to calculate or estimate the subject's core body temperature. Sensors may be included to detect and measure the presence of volatile organic compounds (e.g., jet fuel) which are chemicals with a high vapor pressure under ordinary conditions, and which can be harmful to the subject if his or her breathing mix becomes contaminated with such compounds. Hydrocarbon sensors may be included to detect and measure the presence of hydrocarbons which can also be harmful to the subject if they contaminate the breathing mix. Flow sensors may be included to measure the rate of gas flow, either inhaled or exhaled. This flow sensor is placed at the distal end of the breathing tube 40 and can be used to measure the rate of breathing mix flow as it enters the breathing tube 40. Accelerometers and gyroscopes may be included in order to detect and measure the subject's body position and orientation at a given time or during a particular event or stage. As noted above, microphones may be included not only for communication, but also for noise canceling functions. Electrodes may also be included to record physiological signals from the subject's body. Preferably, dry electrodes are used. Such electrodes may be used to record EEG, ECG, EMG, EOG signals, and the like. All of the above sensors may be included and provide valuable measurements which can be used to calculate further biometrics to help evaluate the subject's status and predict the onset of dangerous breathing or other health conditions such as hypoxia.

In the present embodiment, both the exhaled breath partial pressure of oxygen 180 and the ambient pressure 190 measurements are used to calculate further values including the exhaled oxygen mole fraction 200, the exhale volume of oxygen (L) 205, and the exhaled end tidal oxygen level (mmHg) 210. The exhaled oxygen mole fraction 200 and exhaled oxygen volume 205 values are essentially a conversion of the oxygen partial pressure 180 measurement and ambient pressure 190 into a volume or amount calculation of oxygen in the exhaled breath. Exhaled end tidal oxygen 210 is another value representing the partial pressure of oxygen, but at the end of the subject's tidal (normal) breath. Each of these values represent the amount of oxygen being expired from the subject in a different manner, and particularly when coupled with a known inspired amount of oxygen, due to a calculated breathing mix, can be used to determine and predict dangerous breathing or other health conditions for the subject.

Also in the present embodiment, both the exhaled partial pressure of carbon dioxide 185 and the ambient pressure 190 are used to calculate the exhaled carbon dioxide mole fraction 215, the exhaled carbon dioxide volume (L) 220, and the exhaled end tidal carbon dioxide level (mmHg) 225. Additionally, the exhaled carbon dioxide mole fraction can be used to calculate the subject's carbon dioxide production (L/s) 230. The exhaled carbon dioxide mole fraction 215 and exhaled carbon dioxide volume 220 values are essentially a conversion of the carbon dioxide partial pressure 185 measurement and ambient pressure 190 into a volume or amount calculation of carbon dioxide in the exhaled breath. Exhaled end tidal carbon dioxide 225 is another value representing the partial pressure of carbon dioxide, but at the end of the subject's tidal (normal) breath. Carbon dioxide production 230 is effectively a measurement of how much carbon dioxide the subject is exhaling as a result of his or her breathing process. Each of these values represent the amount of carbon dioxide being expired from the subject in a different manner, and particularly when coupled with a known inspired amount of carbon dioxide, due to a calculated breathing mix, can be used to determine and predict dangerous breathing or other health conditions for the subject.

Still in the present embodiment, the exhaled gas flow rate measurement is used to calculate the inhaled breath volume (L) 235, and the subject's ventilation (L/min) 240. The inhaled breath volume is a basic measure of the volume of gas (breathing mix) inhaled by the subject during each breath. Ventilation, as discussed above, is the rate at which gas enters and leaves the lungs. Ventilation, in turn, can also be used to calculate the subject's hypoxic ventilatory response, thus not requiring a pulse oximeter and its accompanying oxygen saturation measurement to calculate this metric.

Many other values may be calculated from the measured sensor values or from the other calculated values that are not directly tied to any one particular sensor, measurement, or calculated value. For example, inhaled breath time (sec) 250, exhaled breath time (sec) 245, respiratory rate (breaths per min) 255, and breath time ratio 260 can all be calculated by general metrics regarding the subject's breathing. This values in particular are useful in identifying or predicting hyperventilation. Additionally, these values may help determine when suffocation may be occurring. In this context, suffocation particularly refers to the instance where pressure and ambient forces (e.g., g-force or depth pressure) force the exhale valve of the breathing mask shut and thus prevent the subject from drawing a breath due to the check valve. One other, innovative metric that is calculated in the present embodiment is the standard oxygen absorption (L/min) 285. Oxygen absorption is a measure of the amount of oxygen the subject absorbs during a breath. However, standard oxygen absorption is a standardized, normalized measurement of the amount of oxygen absorbed in a breath for the subject based on the altitude (for pilots and aircrew) or depth (for divers). This is an important feature because this measurement allows the system to more accurately predict the subject's breathing conditions and to predict the onset of potentially dangerous conditions.

Figure 8:
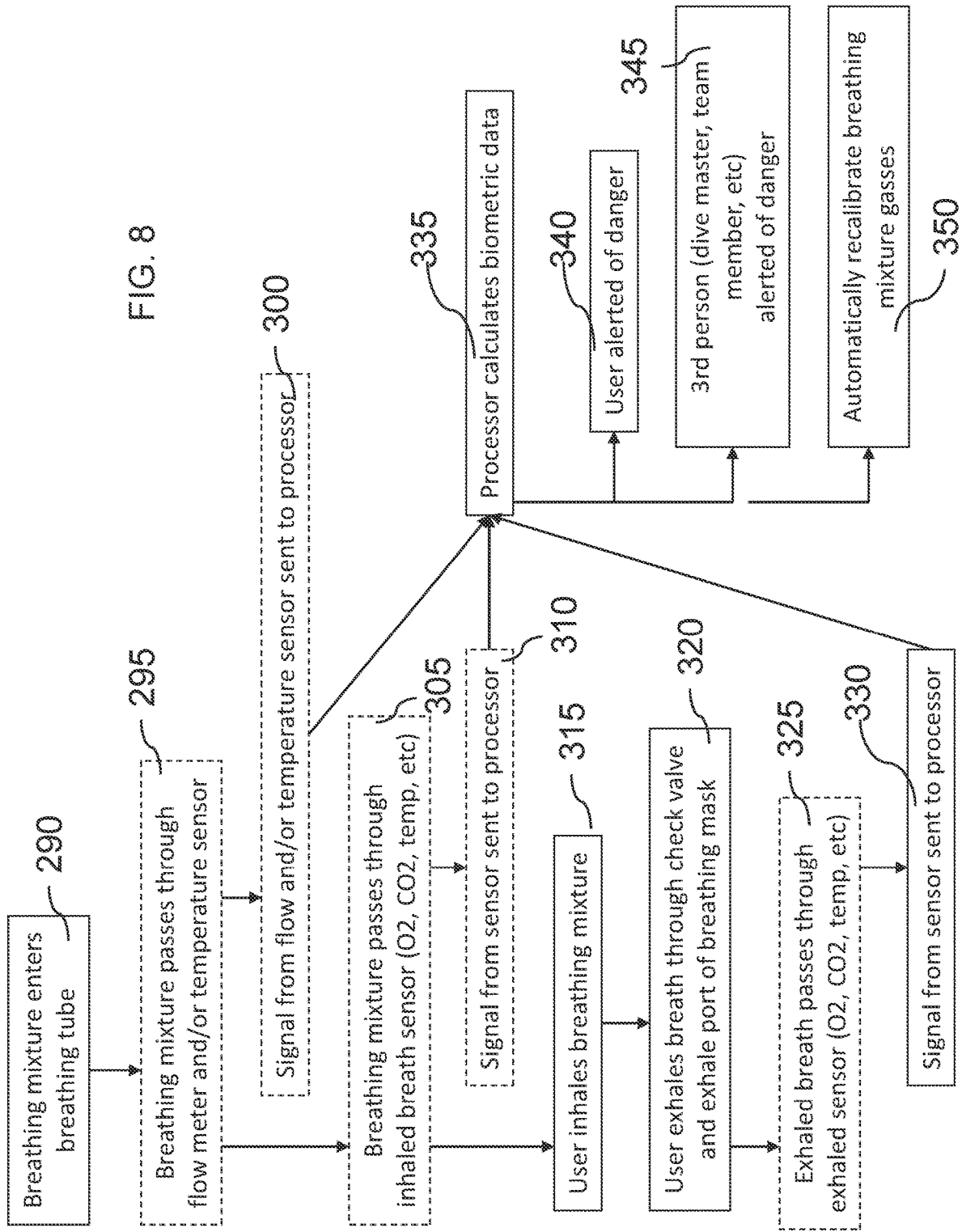
FIG. 8. Flow chart depicting the process of using the present invention from starting air flow, to measurement by one or more sensors, through transmission of a warning or other signal for alerting or treating dangerous breathing or other health conditions.

FIG. 8 is a flow chart depicting the process of sending a warning or alert based on the measured and calculated values. The figure generally follows the flow of the breathing mix of gases from generation by the OBOGS or other breathing mix generator to exhalation by the subject. Sensor measurements are split off in order as the measurements are taken and transmitted.

First, the OBOGS or other breathing mix generator system mixes and pressurizes the breathing mix, forcing the mix to enter the breathing tube 290. The breathing mix then travels through the breathing tube towards the subject's breathing mask. In some embodiments, a flow sensor is attached to the distal end of the breathing tube. In other embodiments, the flow sensor further contains other sensors, which may be any of those previously described. In the particular embodiment portrayed here, the flow sensor also contains a temperature sensor. Thus, the breathing mixture enters the flow meter and passes through 295. As the breathing mix passes through, the flow sensor and temperature sensors measure their respective values and transmit a signal 300 based on those measurements to the processor for analysis.

Once the breathing mix passes through the flow and temperature sensor, it continues through the breathing tube and toward the subject's breathing mask. In some embodiments, the breathing tube attaches to the breathing mask by means of a coupling inhaled gas sensor housing which contains at least one inhaled gas sensor. The inhaled gas sensor(s) may be of any type of variety previously described. The breathing mix exits the breathing tube, and passes through or over the inhaled gas sensor 305, and enters the breathing mask. Much like the flow sensor above, as the breathing mix passes through or over the inhaled gas sensor(s), the inhaled gas sensor(s) make the appropriate measurements and transmit a signal 310 based on those measurements to the processor for analysis.

Once the breathing mix passes into the breathing mask, the subject inhales the breathing mixture 315, and then subsequently exhales his or her breath 320. A check valve is generally employed to prevent reverse flow of breathed gases and to prevent an excess build-up of gases in the mask which could create difficulties in breathing for the subject. Further, the check valve helps force the exhaled breath out through the exhaled gas sensor housing which contains at least one exhaled gas sensor. Again, the exhaled gas sensor may be any of the type previously described, or a combination thereof. The exhaled breath passes over or through the exhaled gas sensor 325 and the exhaled gas sensor makes its respective measurement. Once the measurement is made, the sensor transmits a signal based on the measured value 330 to the processor for analysis.

The processor receives each of the sensor signals and correlates those signals to the measured values on which they are based. The processor comprises an algorithm which takes the sensor measured values and calculates a number of additional metrics (see FIG. 7). The measured values and calculated metrics are then combined and correlated by the algorithm. The resulting calculated biometric data 335 represents the subject's health status, breathing information, environmental data, and the like, all depending on the number and combination of sensors used. The algorithm then determines, based on the resultant biometric data, whether the subject is experiencing a dangerous condition, such as hypoxia, suffocation, hyperventilation, etc., or if the data predicts that such a dangerous condition is about to or soon to occur to the subject. In the event of an identified or predicted dangerous condition, the processor, further comprising a transmitter, sends out a warning or alert to send help to the subject who may be unable to respond, or to help prevent the dangerous condition from occurring. One type of warning or alert that may be sent out is to the subject himself or herself 340. Alternatively, the warning or alert may be sent to a third person 345, such as a team member, remote monitor, or an overseer (e.g., a divemaster) who can then try to give aid to the subject. Still another type of warning or alert might be to a closed-loop system which then automatically recalibrates 350 the breathing mix of the subject's air supply in order to counteract the existing dangerous condition or prevent the predicted dangerous condition from occurring.

In some closed-loop embodiments, systems may be employed which, upon receiving an alert or warning from the biometric monitoring system, automatically take control of the subject's vessel or equipment. Such systems are particularly useful for the fighter pilot embodiments where dangerous conditions may render the subject incapacitated and in severe danger of crashing and death. Such a closed loop system would allow an auto-pilot feature to keep the aircraft aloft while the subject is restored to capacity. A similar system may be employed where the alert or warning is sent to a third party, thus giving the third party control of the subject's vessel or equipment (e.g., remote control flight). In underwater embodiments, particularly in military, commercial, and recreational embodiments, the alert or warning may activate an automatic safety mechanism which may not only help locate the subject, but may also engage a mechanism to bring the subject to the surface for easier extraction and rescue. Many such applications are contemplated in the various embodiments of the present invention.

Figure 9:
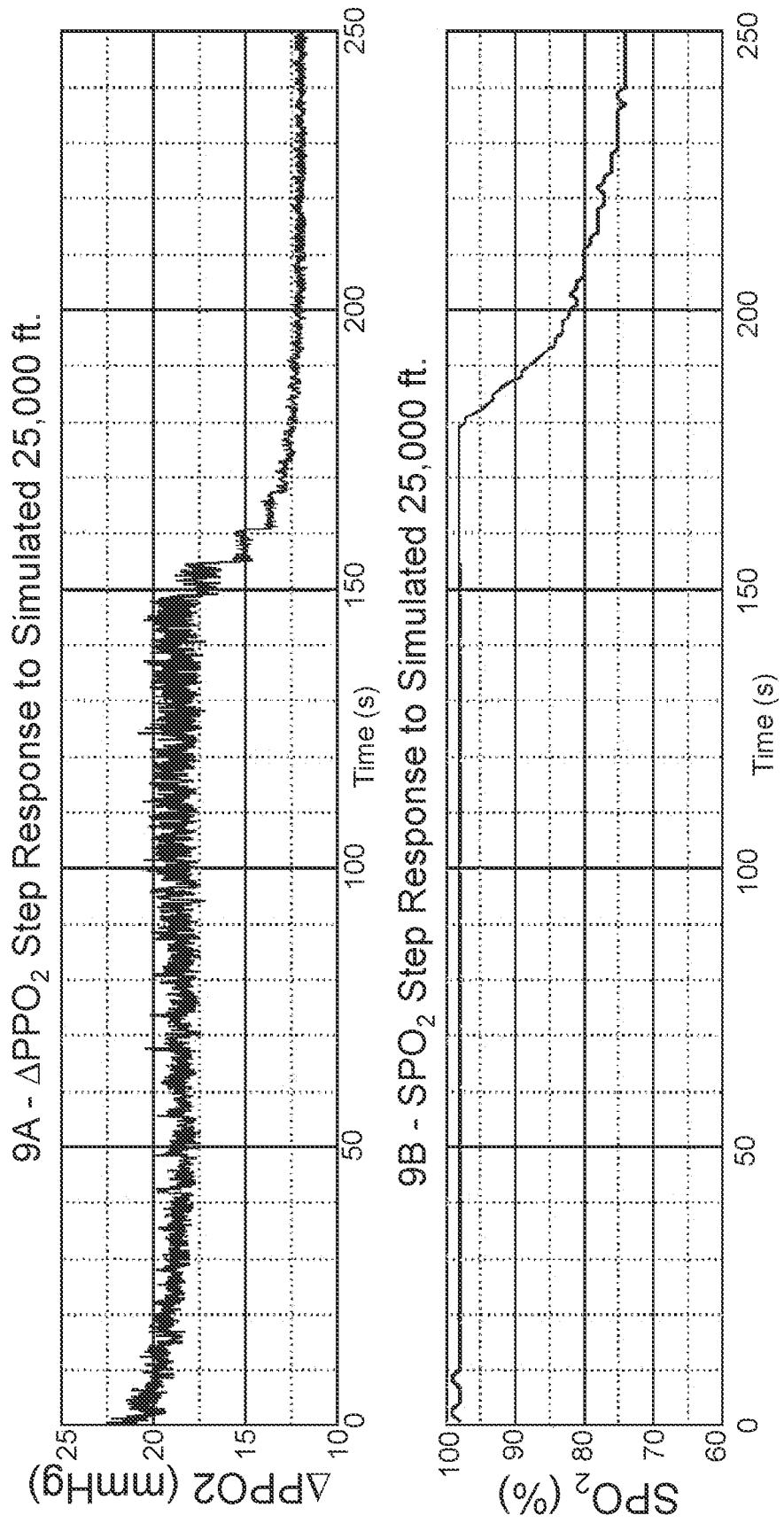
FIG. 9. Graphs comparing step response of present invention to traditional pulse oximeter in recognizing hypoxia at simulated 25,000 feet.

FIG. 9 is a graph representing hypoxia detection response of the present invention (9a—$\Delta PPO_2$) versus that of a traditional pulse oximeter (9b—$SPO_2$) system. As can be seen from the graphs, the present invention was able to detect and identify the onset of hypoxia in this particular patient thirty seconds earlier than the traditional pulse oximeter-only system. In the applications envisioned for this invention, to improve safety, thirty seconds is a vast window of time. The faster response of the present invention over traditional systems represents the ability to not only more rapidly identify and respond to existing hypoxic conditions, but also presents the opportunity to predict and prevent dangerous conditions before they occur.

Figure 10A:
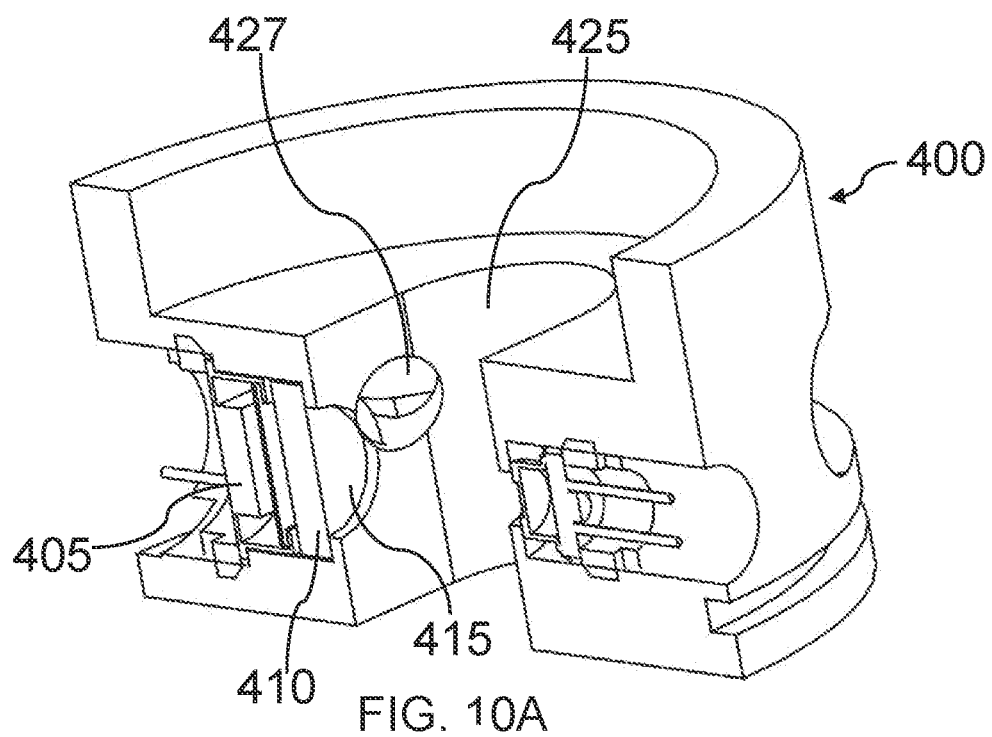
FIG. 10A. Cross-sectional view of one embodiment of each of the oxygen sensor.

FIG. 10 depicts cross-sectional views containing greater detail of (A) one embodiment of an oxygen sensor used with the present inventions, and (B) one embodiment of a carbon dioxide sensor used with the present invention. FIG. 10A depicts an embodiment of an oxygen sensor 400. The particular oxygen sensor 400 comprises a photodiode 405 which may be of any type currently known to those of skill in the art, such as a PIN photodiode, or later developed. This photodiode 405 emits a light source, preferably in the visible blue spectrum, through a ruthenium-based dye 415 and thus excites the ruthenium dye. The photodiode's 405 emitted light is first passed through an optical long-pass filter 410 designed to attenuate shorter wavelengths and allow the longer wavelengths to pass through the filter and then into and through the ruthenium-based dye. The optical filter 410 may also be of any type presently known to those of skill in the art, or a type later developed, but in the particular embodiment is a colored glass filter. The now-excited light exits the dye 415 and enters the flow channel 425, and is in the orange spectrum rather than blue. While in the flow chamber, the light collides and interacts with the air, and more specifically the oxygen contained in the flow chamber 425. Oxygen interferes with the excitation of the ruthenium-based dye and effectively acts to quench the intensity of the light emission while simultaneously increasing the fluorescence lifetime. These characteristics, intensity and fluorescence lifetime, are indicative of the rate at which oxygen collides with the ruthenium-based dye, and this collision rate is then used to calculate and determine the partial pressure of oxygen in the air or breath in the flow chamber 425. The light passes through the chamber 425 and is detected by another diode on the other side of the flow chamber. This diode may again be of any type or variety currently known or later developed, but in this particular embodiment depicted, it is a laser diode. Additionally, the oxygen sensor 400 comprises a port 427 for installation of a thermistor (not shown). The thermistor is used to measure the temperature of the air or breath in the flow chamber 425, and to thus allow the system to provide temperature compensation which further allows for the calculation and determination of the partial pressure of oxygen, which is a function of both the rate of collision between oxygen and the ruthenium dye, and temperature.

Figure 10B:
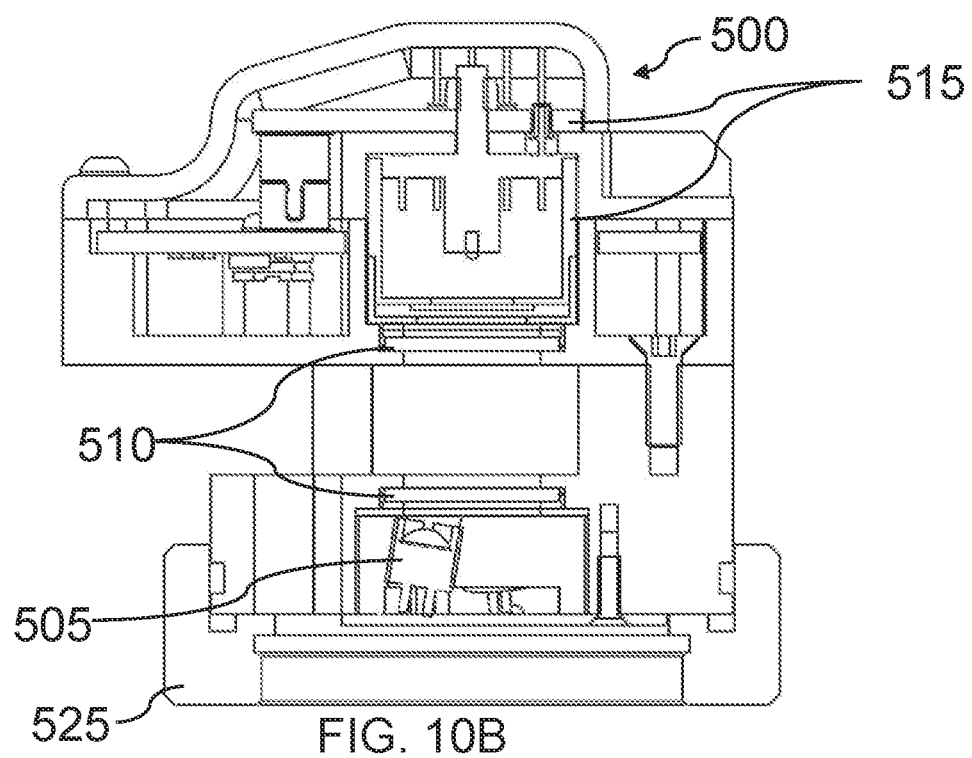
FIG. 10B. Cross-sectional view of one embodiment of each of the carbon dioxide sensor.

FIG. 10B depicts one embodiment of a carbon dioxide sensor 500. The carbon dioxide sensor 500 comprises an array of infrared LEDs 505 which emit infrared light of a known wavelength and amplitude, preferably in a square wave, that is focused on a detector, in this case an infrared photovoltaic detector 520. As the array of infrared LEDs 505 emits the infrared light, the light passes through at least one coated lens 510, travels through the air or breath flow where the light collides with carbon dioxide molecules in the breath, and is collected by an infrared detector 515. The light signal, altered by the absorption of some light by the carbon dioxide molecules, is collected and measured such that the change in the amplitude of the waveform is corresponds to the concentration of carbon dioxide in the breath or air. Preferably, the infrared detector(s) 515 is temperature controlled in order to prevent condensation on the sensor components and pressure drift of the sensor, and to maintain proper calibration of the measurements.

Figure 11:
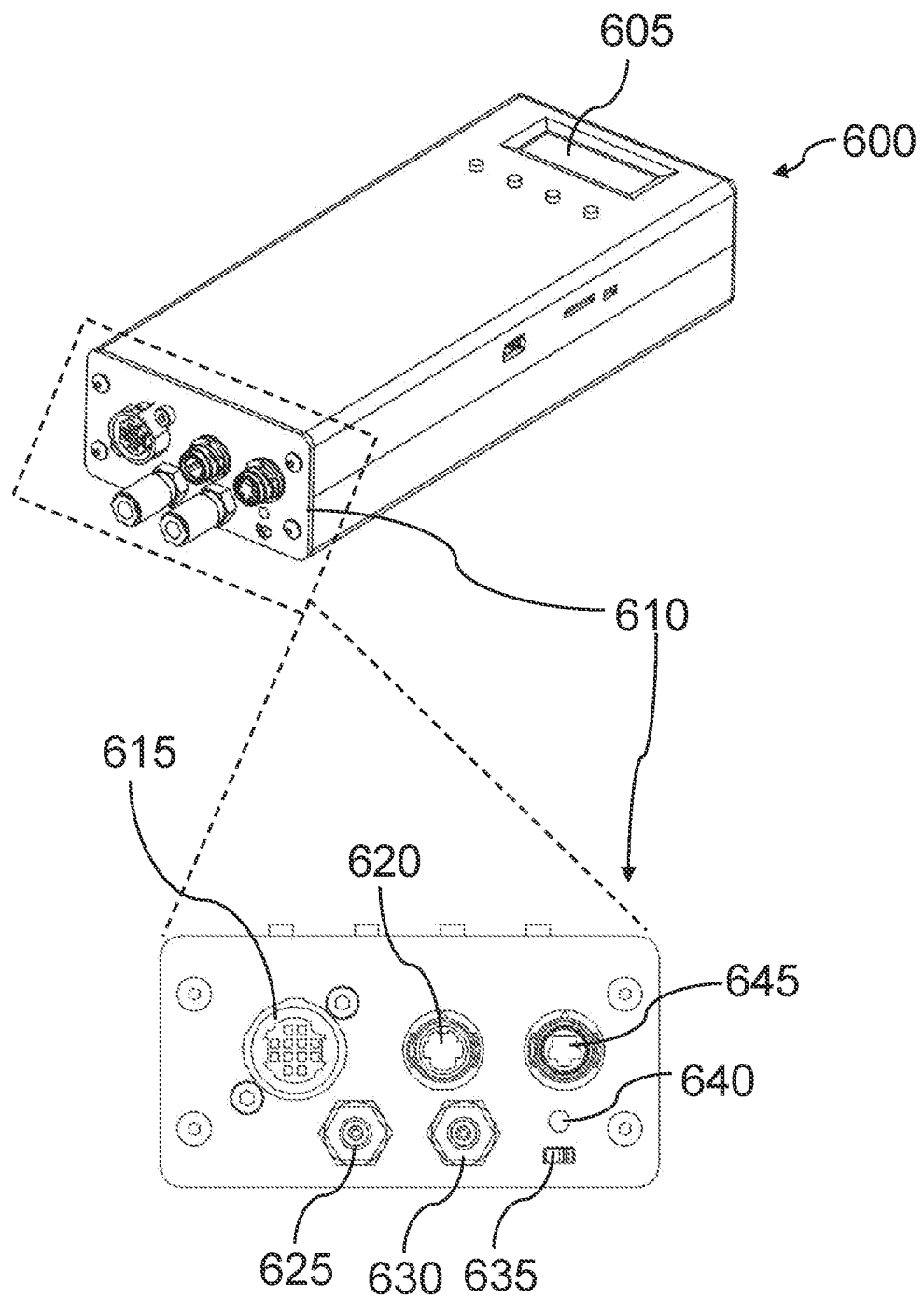
FIG. 11. Perspective view of one embodiment of the data acquisition and/or processing circuitry (sometimes referred to as a Portable Digital Analysis Unit or PDAU) in a singular enclosure with a callout view to the connection panel of the enclosure.

FIG. 11 depicts one embodiment of a Portable Digital Analysis Unit (PDAU) for processing sensor data and performing the system's monitoring, prediction, mitigation and alert functions. The Portable Digital Analysis Unit 600 is preferably constructed to be small, relatively lightweight, and thus easily and readily able to be carried by subject or stowed in his or her equipment, gear, clothing, or elsewhere one or in immediate proximity to the subject. Preferably, the PDAU 600 is stored in a pocket or compartment in the subject's clothing such that the subject does not have to actively carry or maintain the PDAU's 600 presence, and the PDAU 600 can remain with the subject performing the continual analysis of his or her breathing conditions. The PDAU 600 may comprise a visual indicator such as a screen 605 for displaying information (such as physiological measurements and calculations, battery status, and the like) or providing a visual alert or warning regarding dangerous breathing and other physiological conditions. The PDAU 600 also comprises a connection panel 610, portrayed in the callout in greater detail, which allows the various sensors to be connected to the PDAU 600 for signal input. In the particularly depicted embodiment, the connection panel 610 comprises connection points for sensors including one carbon dioxide ($CO_2$) sensor 615, a flow sensor 620, and two pressure sensors 625 and 630. The connection panel 610 further comprises a power switch 635 for turning the unit on and off, a status light 640 for providing a visual indicator of whether the unit is on or off, and optionally if the unit is functioning properly (e.g., by displaying different colored lights to indicate status, mode or operation); and an analog out port 645 for allowing the PDAU to be connected to an external device (not shown) for transferring physiological measured and calculated data for separate analysis and review, or to other devices for display (e.g., an external monitor). This image merely depicts one embodiment of the present invention where the PDAU and system are specifically designed to only measure carbon dioxide, flow, and two pressures either all together, or in some combination. Many other embodiments existing allowing for measurement with all of the sensors described herein, in numerous combinations.

As noted above, preferably the electronic components contained within the PDA are miniaturized in order to decrease the size and weight of the system, and thus make it less cumbersome to the user. Miniaturized components allow for a much smaller enclosure to be used where the components are consolidated together. The PDAU can also be formed into different shapes as opposed to the depicted rectangular box, and can be adapted to be integrated into other components of the system. For example, in at least one embodiment, the electronics components can be sufficiently miniaturized and adapted to be integrated into the CRU module or other inhaled regulator fitting, thus eliminating the need for a completely separate PDAU. Or, more preferably, the centralized PDAU can be eliminated, and instead the electronic and processing components can be separated and integrated into the sensor housings, either on the inhaled- or exhaled-sides, or both. For example, various embodiments may utilize sufficiently miniaturized electronics components, integrated into the sensor housing on either or both sides, wherein a separate processing component receives the signal solely from the sensor(s) with which it is integrated, is powered by either a local, similarly integrated power source or by connection to the vehicle power system, and performs all necessary data collection and processing functions for the given sensors, then transmits and/or stores that data accordingly, while an entirely separate miniaturized set of electronic components performs the same functions for the sensor(s) on the other side. Preferably, the electronics in most embodiments are sufficiently miniaturized to be portable, and perhaps modular. Another optional advantage to the integration of electronics components into the in-line CRU module or other inhaled regulator is that the electronic components can receive power from the on-board, or vehicle mounted, power supply system, rather that requiring a battery. Removal of the battery allows for significant reduction in size and weight of the system.

Figure 12:
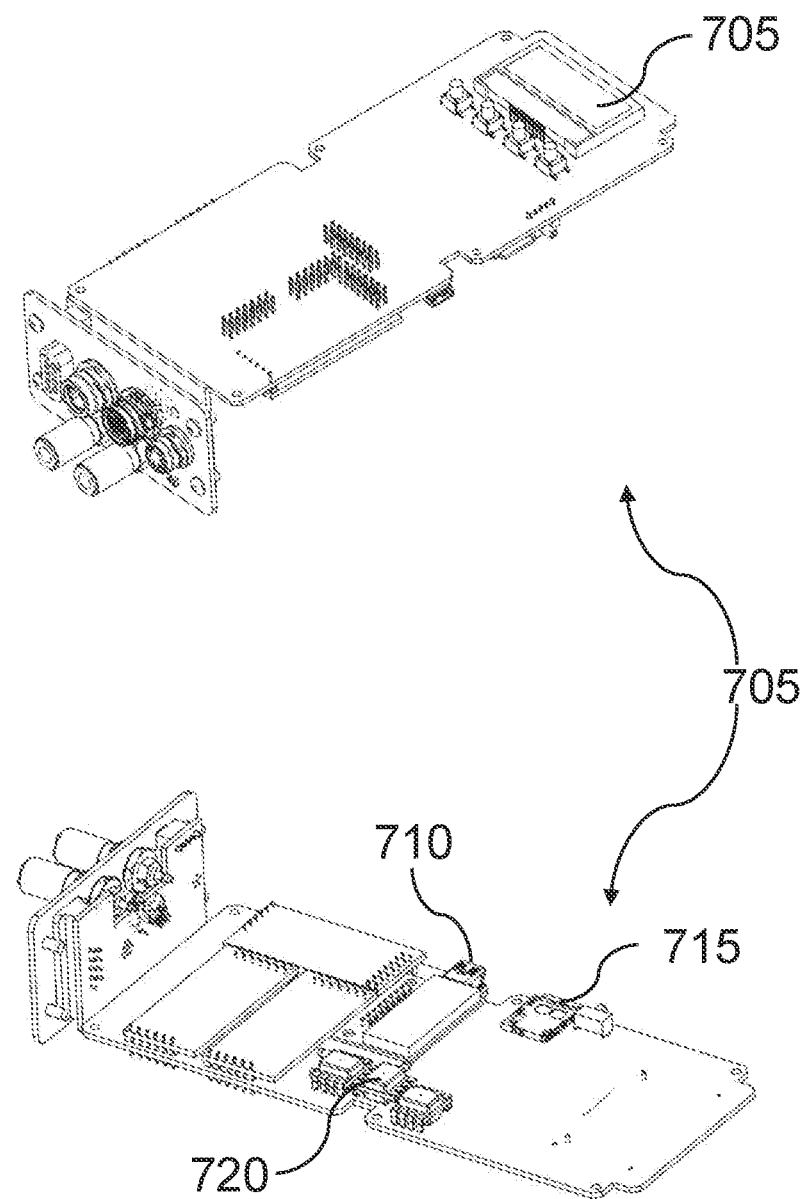
FIG. 12. Depiction of one embodiment of the data acquisition and/or processing circuitry that can be contained in a PDAU.

FIG. 12 depicts one embodiment of the electronics board for the Portable Digital Analysis Unit. The PDAU electronics board 700 comprises the electrical components for receiving signals from the various sensors (not shown) of the system, and using those sensor signals that correspond to physiological conditions of the subject to monitor, predict, mitigate, and warn of occurring or impending dangerous breathing or other physiological conditions. Many embodiments of the PDAU electronics board 700 comprise a visual display 705 for displaying information (such as physiological measurements and calculations, battery status, and the like) or providing a visual alert or warning regarding dangerous breathing and other physiological conditions. In the particularly depicted embodiment, the display comprises an LCD screen for providing messages which may be in the form of text, blinking or flashing lights or colors, or any other variety of message or indicator which may be conveyed by such displays. The depicted embodiment further contains a connection point for a thermistor 710 by which said thermistor may be connected to the board 700, thus allowing the system to take temperature measurements in accordance with the description of various temperature recordings herein. The board 700 further comprises a connection for an air flow sensor 715 for connecting and receiving signals from an air flow sensor. An analog to digital (A/D) converter 720 is also included for converting the analog signals received directly from the sensors into a digital format which can be used by the system's algorithm(s) to perform the necessary calculations. The system is preferably capable of being both self-powered by means of a battery and/or externally powered for tethered or more permanent applications.

Figure 13:
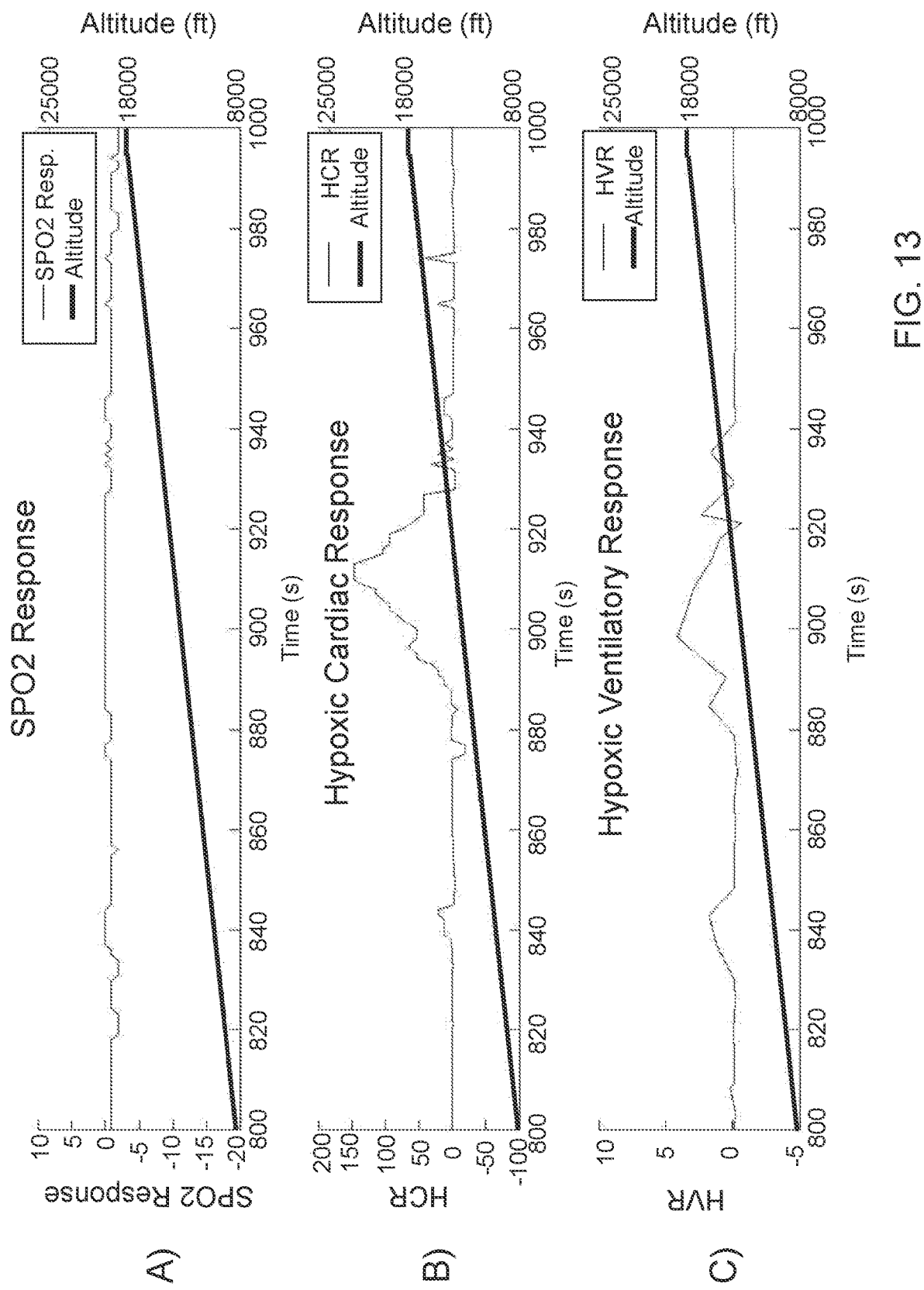
FIG. 13. Graphical representations of experimental data depicting the change, over time, based on a simulated steady increase in altitude of various physiological metrics including: 13A) $SPO_2$; 13B) Hypoxic Cardiac Response; and 13C) Hypoxic Ventilatory Response.

FIG. 13 presents data from an experiment simulating a steady, gradual increase in altitude wherein blood oxygen concentration response ($SPO_2$ Response) (13A), Hypoxic Cardiac Response (HCR) (13B), and Hypoxic Ventilatory Response (HVR) (13C) were all calculated on a continual basis to determine the response to simulated altitude.

Figure 14:
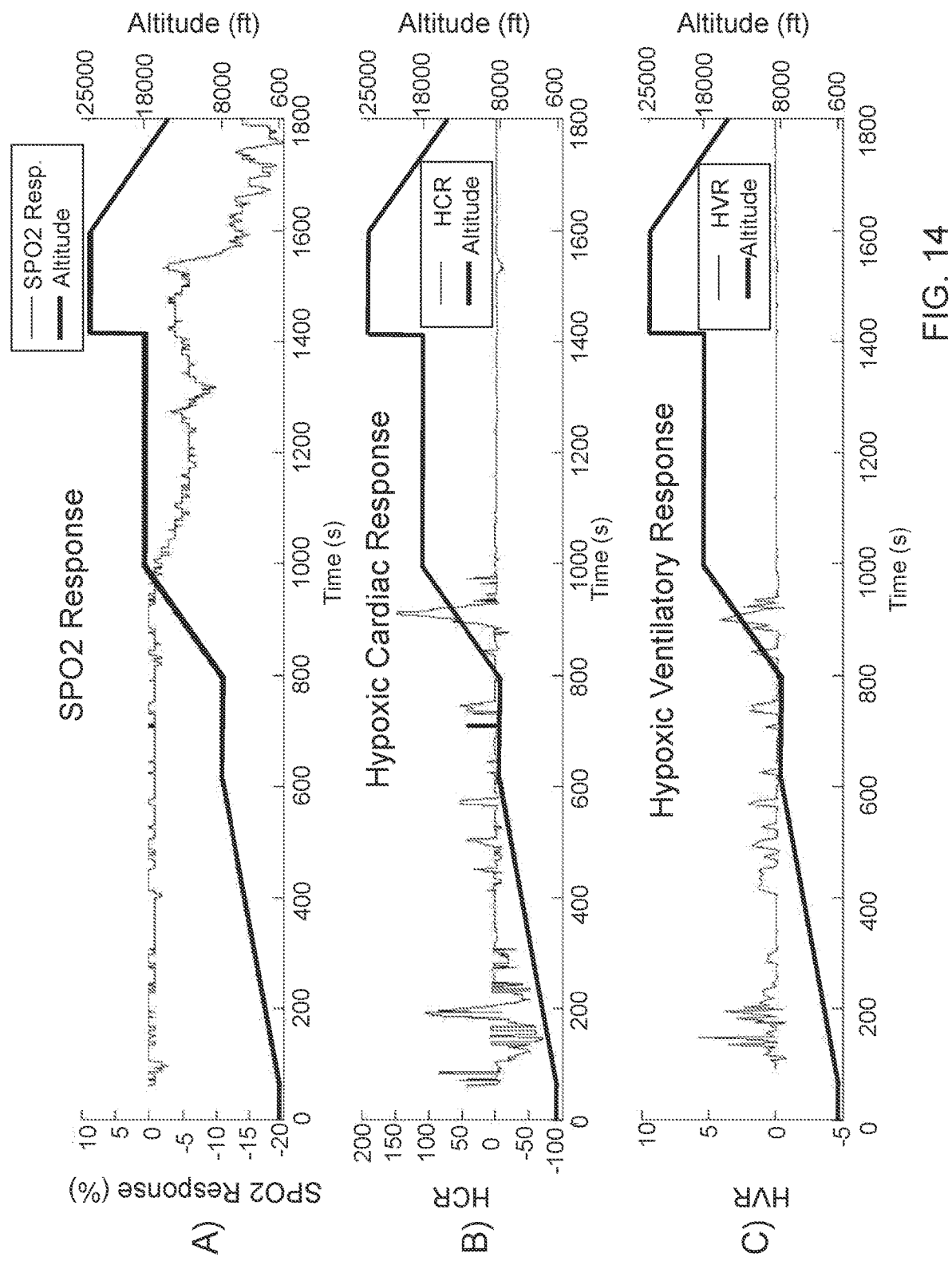
FIG. 14. Graphical representations of experimental data depicting the change, over time, based on various simulated changes in altitude of various physiological metrics including: 14A) $SPO_2$; 14B) Hypoxic Cardiac Response; and 14C) Hypoxic Ventilatory Response.

FIG. 14 presents data from an experiment simulating both gradual and more drastic, or near immediate changes in altitude wherein blood oxygen concentration response ($SPO_2$ Response))14A), Hypoxic Cardiac Response (HCR) (14B), and Hypoxic Ventilatory Response (HVR) (14C) were all calculated on a continual basis to determine the response to simulated altitude.

Figure 15:
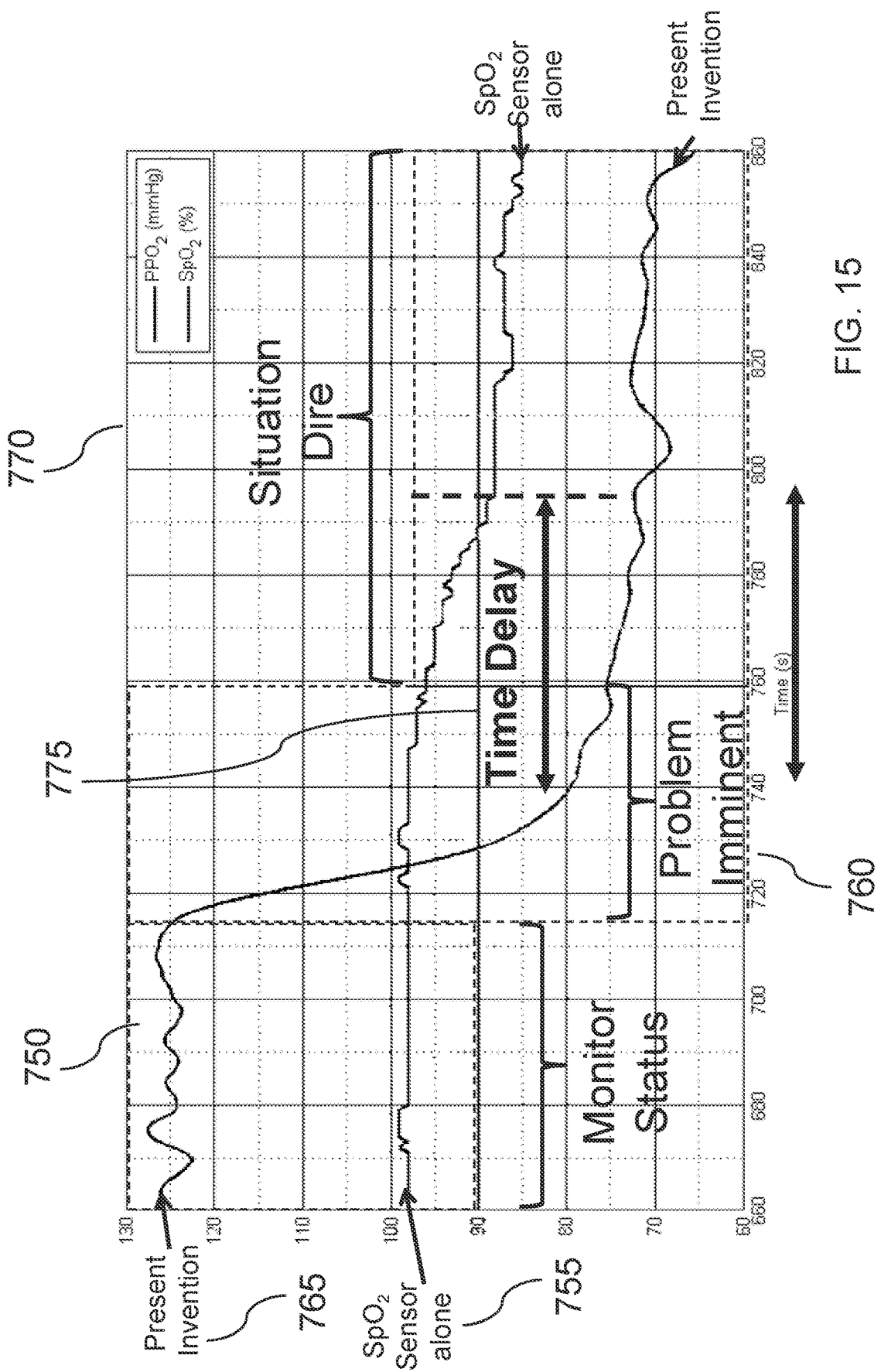
FIG. 15. Graphical depiction of data showing the improved response time of the present invention with labels with labels indicating the wearer's physiological response and the points at which changes are meaningfully detected.

FIG. 15 depicts a comparison of data collected from a typical blood oxygen concentration ($SpO_2$, measured in %) sensor alone and the present invention's suite of measurements used for calculating a subject's partial pressure of oxygen ($PPO_2$, measured in mmHg). As a general overview, the graph depicts the time delay between the times when each measurement method detects that a dangerous breathing or other physiological condition is occurring. The first phase 750 of the experiment involved taking measurements and monitoring the subject's status while increasing, or simulating an increase in altitude. Both the traditional blood oxygen concentration 755 and the present invention's partial pressure of oxygen measurements and calculations 765 are substantially steady indicating a stable subject status. After a certain altitude, or simulated altitude is reached, however, the two measurements systems begin to diverge when a dangerous breathing or other physiological condition becomes imminent 760. At approximately 713 seconds into the experiment, the present invention's partial pressure of oxygen 765 metric begins to rapidly decrease indicating a drastic drop-off in the subject's $PPO_2$. The PPO2 metric 765, according to the programmed algorithms indicates at around 735 seconds that a dangerous breathing or other physiological condition is, in fact, beginning to occur. It is not until approximately 794 seconds that the blood oxygen concentration metric 755 actually indicates that such a condition is occurring. The subject's condition becomes very dire and potentially life threatening 770 at approximately 760 seconds into the experiment. Thus, it can be seen from this data that a traditional blood oxygen concentration measurement 755 does not adequately detect a dangerous breathing or other physiological condition, until significantly later in time than when the condition becomes dire (approximately 34 seconds in this particular data set). Conversely, the present invention's partial pressure of oxygen metric 765 begins to indicate that the subject may experience a dangerous breathing or other physiological condition significantly early compared to when the condition becomes dire (in the depicted data set, approximately 25 seconds prior to the condition becoming dangerous, and perhaps as early as about 47 seconds in advance). In other words, the present invention's partial pressure of oxygen metric 765 can provide an accurate detection of such a dangerous condition, but more importantly may be able to predict the onset of such a condition, and allow the subject or the system to mitigate the severity and/or prevent the condition from occurring at all. To complete the comparison, there is a substantial and significant time delay 775 between the present invention's partial pressure of oxygen metric 765, and the traditional blood oxygen concentration measurement's detections of a dangerous breathing or other physiological condition—blood oxygen concentration was between 60 to 80 seconds slower than the partial pressure of oxygen metric. Therefore, the present invention presents a significant improvement over traditional methods for detecting such dangerous conditions, and further provides the ability to potentially predict and mitigate and/or prevent such conditions from occurring altogether.

Figure 16:
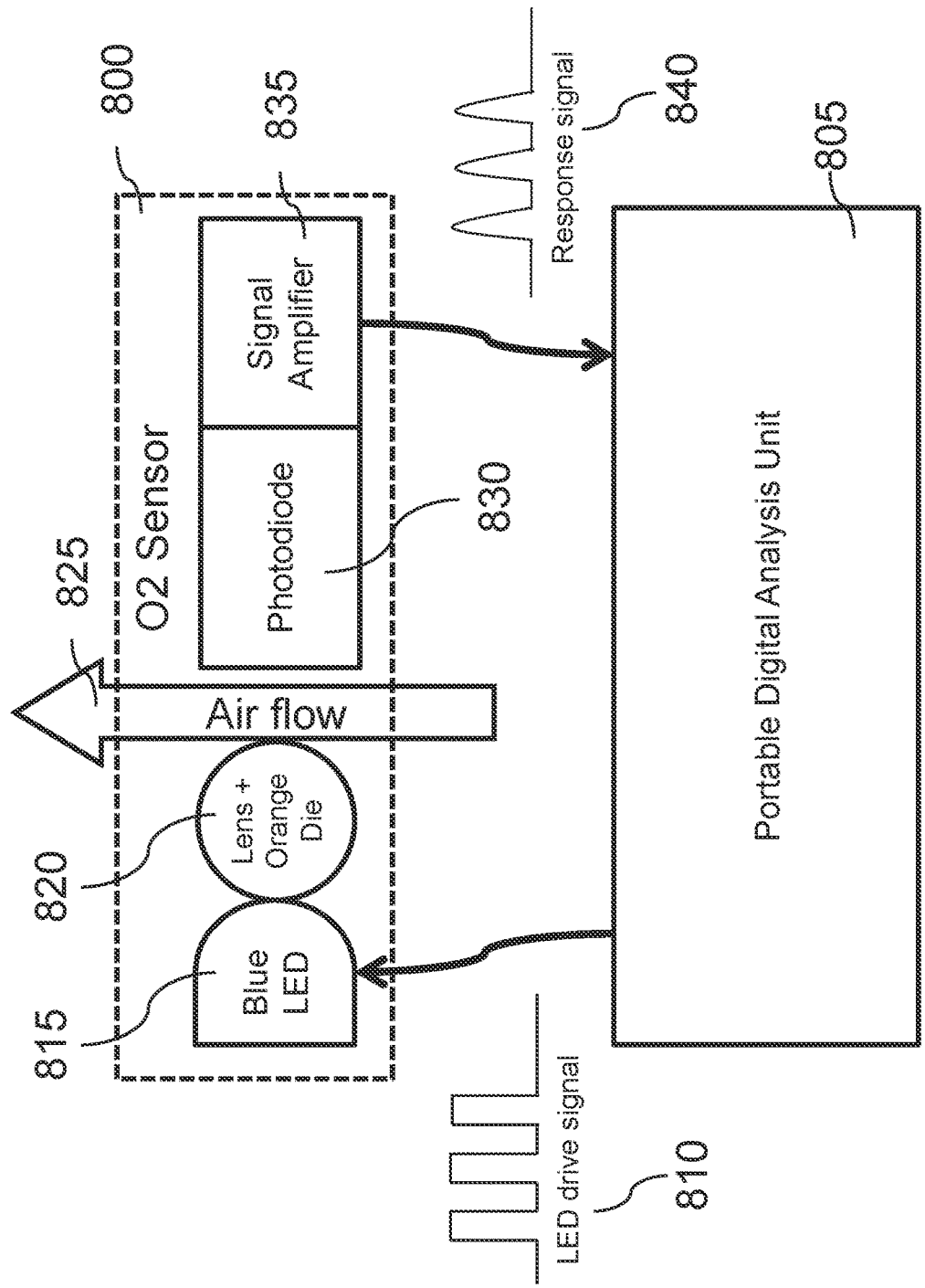
FIG. 16. Graphical representation of the measurement process and data flow of the present invention utilizing an oxygen sensor.

FIG. 16 depicts the measurement and data flow of an embodiment of the present invention utilizing at least one depicted oxygen sensor. In this particular embodiment, the Portable Digital Analysis Unit (PDAU) 805 outputs a signal 810 that drives the LED emitter 815 of the oxygen sensor 800. The LED drive signal 810 of the depicted embodiment is output as a square whereby the LED emitter 815 is caused to emit a measurement light pulse with known attributes. The blue light emitted from the LED 815 passes through a lens coated with ruthenium dye which is excited by the blue light and passes light through in the orange spectrum, which then passes through the air flow 825, on either inhaled or exhaled side depending on where the oxygen sensor 800 is mounted. As the orange light passes through the air flow, it collides with oxygen molecules in the airflow, which interferes with the excitation of the ruthenium dye and quenches the intensity of the light. After passing through the airflow, the light that passes through is collected by the photodiode 830 and this measurement signal is amplified by a signal amplifier 835. This amplified measurement signal is then transmitted back to the PDAU 805 in the form of a response signal 840 that represents the changed intensity of the excited light as a result of the concentration of oxygen molecules in the air flow. The response signal 840 is then processed by the electronic components of the PDAU 805 in order to translate the signal 840 into an actual measurement for the concentration of oxygen.

Figure 17:
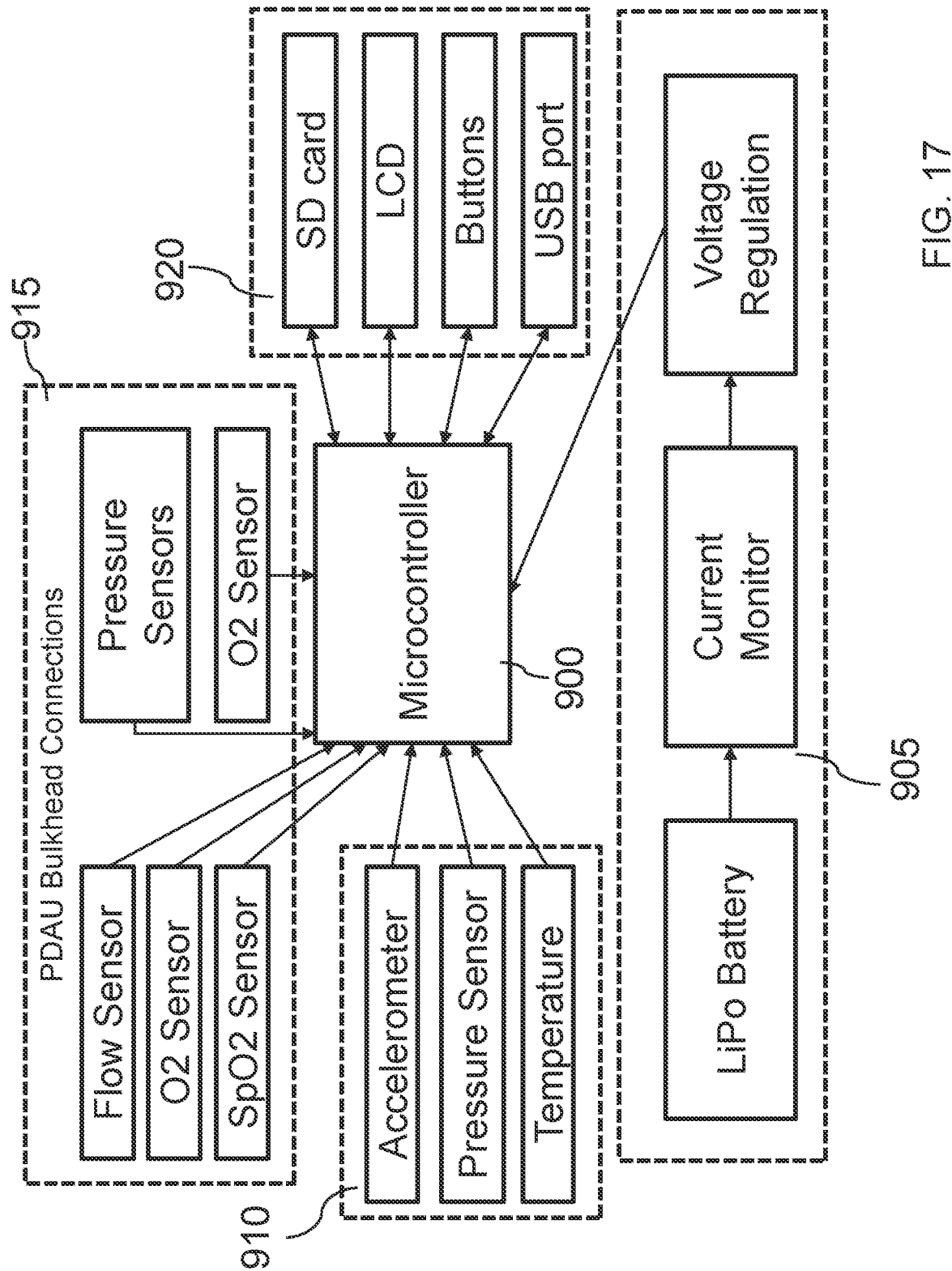
FIG. 17. Flow chart depicting various components and subsystems of the processing and control circuitry, which may be comprised in a Portable Digital Analysis Unit.

FIG. 17 is a flow chart depicting various components and subsystems of one embodiment of the processing circuitry and/or Portable Digital Analysis Unit (PDAU) present invention and the interaction and information flow between the components. The figure depicts several main groupings of PDAU components or subsystems including a microcontroller 900, a power management system 905, an internal sensor suite 910, a connections system 915, and an input and user interface section 920. The microcontroller 900, as described herein, can be any type or variety of microcontroller, processor or other processing component that is capable of receiving various input signals and implementing algorithms to process the data as desired. The power management system 905 comprises the power source (for example a rechargeable battery), a monitor to track the power currents within the system, and a regulator to control the power provided to the various components of the system, and in particular the microprocessor 900 PDAU components. The power management system outputs the power and command signals to the microprocessor 900 to control the operation of the PDAU. The internal sensor suite 910 can comprise any sensors that might be included in the PDAU as described herein, including, as depicted, accelerometers, pressure sensors and temperature sensors. The internal sensor suite for the PDAU provides data corresponding to the condition and environment of the PDAU and its components, and allows for coordination between various data streams (e.g., between the PDAU and vehicle data systems), as described above. The connections system 915 allows and provides a point for the processing circuitry/PDAU of the subject-worn monitoring system to be connected to and interface with a vehicle (e.g., aircraft, submarine, helicopter, etc.). Through the connections system 915, the many sensors and data streams of the vehicle-based measurement systems can input data into the PDAU and those measurements can be taken into account in the processing of subject data to give a more complete picture of the subject's condition based on all environmental factors. The user interface section 920 provides the interaction points for the subject or another user to interact with the PDAU, whether to input data or commands, to view outputs, or other forms of interaction with the unit. Also, through the user interface section, a user may install or remove removable memory for data transfer, or connect the unit to an external system for data transfer.

It will be apparent to those skilled in the art that various modifications and variations can be made to the present invention without departing from the spirit and scope of the invention. Thus, it is intended that the present invention cover the modifications and variations of this invention provided they come within the scope of the appended claims and their equivalents.

The invention claimed is:

1. A system for monitoring breathing or health conditions related to a subject's breathing comprising:
    a breathing mask;
    a subject-mounted sensor unit comprising at least one oxygen sensor having a signal related to an in-breath partial pressure of oxygen within the breathing mask during the subject's breathing, the at least one sensor being in fluid communication with the breathing mask, and the at least one oxygen sensor being adapted to obtain a first measurement corresponding to the partial pressure of oxygen during inhalation and a second measurement corresponding to the partial pressure of oxygen during exhalation;
    at least one flow sensor adapted to measure air flow rates during the subject's breathing and having a signal related to the flow rate of breath of the subject;
    at least one blood oxygenation sensor adapted to measure blood oxygenation levels of the subject;
    at least one electronic component, including at least a processor, the at least one electronic component adapted to receive the signals from the sensors, and the processor is adapted to calculate a standard oxygen absorption value based at least in part on the first and second measurements and the signal of the at least one flow sensor, and further to calculate one or more metabolic metrics selected from the group consisting of inspiratory volume, expiratory volume, carbon dioxide ($CO_2$) produced, the ($O_2$) consumed, respiration rate, breath duration, peak negative mask pressure, and peak positive mask pressure; and
    at least one machine learning algorithm comprised in the processor, the at least one machine learning algorithm adapted to predict a blood oxygen concentration trend based at least in part on the calculated standard oxygen absorption value;

wherein the at least one machine learning algorithm is adapted to compare respiratory and gas exchange patterns of the subject with measured blood oxygenation levels of the subject, and the system is adapted create a unique algorithm for the particular subject adapted to improve classification accuracy with continued use.

2. The system of claim 1, wherein the sensor unit further comprises one or more of the sensors from the group consisting of altitude sensors adapted to measure altitude of the subject, accelerometers adapted to measure the subject's body position, orientation, and/or g-forces on the subject's body, ambient pressure sensors adapted to measure the ambient pressure surrounding the subject, flow sensors adapted to measure air flow rates of inhaled breathing gas, temperature sensors adapted to measure the temperature of breathing gas supplied from the oxygen source, inhaled breath, exhaled breath, and/or ambient temperature surrounding the subject.

3. The system of claim 2, wherein the sensor unit comprises at least one temperature sensor adapted to measure the temperature of exhaled breath of the subject and/or the temperature of the oxygen sensor and/or carbon dioxide sensors.

4. The system of claim 3, wherein the system is further adapted to decrease condensation and thermal drift of at least one of the sensors based at least in part on the measured temperature of the exhaled breath of the subject, the temperature of the oxygen sensor, and/or the temperature of the carbon dioxide sensor by cooling the sensor(s) when oxygen concentration of breathing gas is above a predetermined threshold and warming the sensor(s) when oxygen concentration of breathing gas is below a predetermined threshold to adapt the sensor(s) to be tolerant to varying pressure, temperature and humidity environments.

5. The system of claim 2, wherein each of the sensors are miniaturized and adapted to fit within a single enclosure attached to or integrated into the breathing mask.

6. The system of claim 5, wherein the at least one machine learning algorithm or a second algorithm comprised on the processor, or a second processer, and being adapted to determine or predict an onset of at least one dangerous breathing or other health condition of the subject based at least in part on both the calculated standard oxygen absorption value and the predicted blood oxygen concentration trend.

7. The system of claim 6, wherein the at least one machine learning algorithm, the second algorithm or a third algorithm also comprised on the processor, the second processor, or a third processor, is adapted to compare the calculated standard oxygen absorption value with the predicted blood oxygen concentration trend based on demographic information of the subject and the determination or prediction of the onset of at least one breathing or other health condition is further based at least in part on the comparison.

8. The system of claim 7, wherein the system is further adapted to predict onset of G-force induced loss of consciousness (G-LOC), to differentiate between G-LOC and hyperventilation, and to monitor and detect occurrence of atelectasis.

9. The system of claim 8, wherein the system is adapted to, upon the prediction of imminent G-LOC or the detection of atelectasis, provide warnings and instructions to the subject to perform specific breathing patterns or techniques to prevent or counteract the G-LOC or atelectasis.

10. The system of claim 2, wherein the oxygen sensor is further adapted to obtain a calibrated measurement of the partial pressure of oxygen by performing three separate functions comprising a first function of acquiring an oxygen measurement signal via fluorescence, a second function of acquiring a background signal using no light, and a third function of acquiring a reference signal using a known wavelength of light, and calculating a ratio of the oxygen measurement signal minus the background signal to the reference signal minus the background signal.

11. A system for monitoring breathing or health conditions related to a subject's breathing comprising:
   a breathing mask;
   a breathing gas delivery system adapted to provide breathing gas comprising at least in part a known volume or partial pressure of oxygen to the breathing mask;
   a subject-mounted sensor unit comprising at least two sensors, the at least two sensors being at least one oxygen sensor having a signal related to an in-breath partial pressure of oxygen within the breathing mask during the subject's breathing, and at least one flow sensor adapted to measure air flow rates during the subject's breathing and having a signal related to the flow rate of breath of the subject, the at least two sensors being in fluid communication with the breathing mask;
   at least one blood oxygenation sensor adapted to measure blood oxygenation levels of the subject;
   at least one electronic component, including at least a processor, the at least one electronic component adapted to receive the signals from the sensors, and the processor is adapted to calculate a standard oxygen absorption value based at least in part on the signals from the at least two sensors, and at least in part on the known volume or partial pressure of oxygen of the breathing gas, and further to calculate one or more metabolic metrics selected from the group consisting of inspiratory volume, expiratory volume, carbon dioxide ($CO_2$) produced, the ($O_2$) consumed, respiration rate, breath duration, peak negative mask pressure, and peak positive mask pressure; and
   at least one machine learning algorithm comprised in the processor, the at least one machine learning algorithm adapted to predict a blood oxygen concentration trend based at least in part on the calculated standard oxygen absorption value;
   wherein the machine learning algorithm is adapted to compare respiratory and gas exchange patterns of the subject with the measured blood oxygenation levels of the subject, and the system creates a unique algorithm for the particular subject adapted to improve classification accuracy with continued use.

12. The system of claim 11, wherein the sensor unit further comprises one or more of the sensors from the group consisting of altitude sensors adapted to measure altitude of the subject, accelerometers adapted to measure the subject's body position, orientation, and/or g-forces on the subject's body, ambient pressure sensors adapted to measure the ambient pressure surrounding the subject, flow sensors adapted to measure air flow rates of inhaled breathing gas, temperature sensors adapted to measure the temperature of breathing gas supplied from the oxygen source, inhaled breath, exhaled breath, and/or ambient temperature surrounding the subject.

13. The system of claim 12, wherein the sensor unit comprises at least one temperature sensor adapted to measure the temperature of exhaled breath of the subject and/or the temperature of the oxygen sensor.

14. The system of claim 13, wherein the system is further adapted to decrease condensation and thermal drift of at least one of the sensors based at least in part on the measured temperature of the exhaled breath of the subject and/or the temperature of the oxygen sensor by cooling the sensor(s) when oxygen concentration of breathing gas is above a predetermined threshold and warming the sensor(s) when oxygen concentration of breathing gas is below a predetermined threshold to adapt the sensor(s) to be tolerant to varying pressure, temperature and humidity environments.

15. The system of claim 12, wherein each of the sensors are miniaturized and adapted to fit within a single enclosure attached to or integrated into the breathing mask.

16. The system of claim 15, wherein the at least one machine learning algorithm or a second algorithm comprised on the processor, or a second processer, and being adapted to determine or predict an onset of at least one dangerous breathing or other health condition of the subject based at least in part on both the calculated standard oxygen absorption value and the predicted blood oxygen concentration trend.

17. The system of claim 16, wherein the at least one machine learning algorithm, the second algorithm or a third algorithm also comprised on the processor, the second processor, or a third processor, is adapted to compare the calculated standard oxygen absorption value with the predicted blood oxygen concentration trend based on demographic information of the subject and the determination or prediction of the onset of at least one breathing or other health condition is further based at least in part on the comparison.

18. The system of claim 17, wherein the system is further adapted to predict onset of G-force induced loss of consciousness (G-LOC), to differentiate between G-LOC and hyperventilation, and to monitor and detect occurrence of atelectasis.

19. The system of claim 18, wherein the system is adapted to, upon the prediction of imminent G-LOC or the detection of atelectasis, provide warnings and instructions to the subject to perform specific breathing patterns or techniques to prevent or counteract the G-LOC or atelectasis.

20. The system of claim 12, wherein the oxygen sensor is further adapted to obtain a calibrated measurement of the partial pressure of oxygen by performing three separate functions comprising a first function of acquiring an oxygen measurement signal via fluorescence, a second function of acquiring a background signal using no light, and a third function of acquiring a reference signal using a known wavelength of light, and calculating a ratio of the oxygen measurement signal minus the background signal to the reference signal minus the background signal.

* * * * *